(12) United States Patent
Keith et al.

(10) Patent No.: US 6,805,695 B2
(45) Date of Patent: Oct. 19, 2004

(54) DEVICES AND METHODS FOR ANNULAR REPAIR OF INTERVERTEBRAL DISCS

(75) Inventors: Peter T. Keith, St. Paul, MN (US); Robert E. Atkinson, Stillwater, MN (US)

(73) Assignee: Spinalabs, LLC, White Bear Lake, MN (US)

( * ) Notice: Subject to any disclaimer, the term of this patent is extended or adjusted under 35 U.S.C. 154(b) by 0 days.

(21) Appl. No.: 10/390,970

(22) Filed: Mar. 18, 2003

(65) Prior Publication Data

US 2003/0187445 A1 Oct. 2, 2003

Related U.S. Application Data

(63) Continuation-in-part of application No. 10/093,990, filed on Mar. 7, 2002, and a continuation-in-part of application No. 10/055,780, filed on Jan. 22, 2002, now Pat. No. 6,689,125, and a continuation-in-part of application No. 09/685,401, filed on Oct. 10, 2000, now Pat. No. 6,579,291, which is a continuation-in-part of application No. 09/542,972, filed on Apr. 4, 2000, now Pat. No. 6,402,750.
(60) Provisional application No. 60/368,108, filed on Mar. 26, 2002, and provisional application No. 60/263,343, filed on Jan. 21, 2001.

(51) Int. Cl.[7] .............................................. A61B 17/56
(52) U.S. Cl. ..................................... 606/61; 623/17.11
(58) Field of Search ........................... 623/17.11, 17.13, 623/17.16; 606/61; 128/898; 600/60

(56) References Cited

U.S. PATENT DOCUMENTS

| | | | |
|---|---|---|---|
| 4,494,261 A | 1/1985 | Morrow | |
| 4,743,260 A | 5/1988 | Burton | |
| 4,772,287 A | 9/1988 | Ray | |
| 4,904,260 A | 2/1990 | Ray | |
| 4,961,740 A | 10/1990 | Ray | |
| 5,047,055 A | 9/1991 | Bao et al. | |
| 5,055,104 A | 10/1991 | Ray | |
| 5,092,866 A | 3/1992 | Breard et al. | |
| 5,123,926 A | 6/1992 | Pisharodi | |
| 5,171,280 A | 12/1992 | Baumgartner | |
| 5,180,393 A | 1/1993 | Commarmond | |
| 5,192,326 A | 3/1993 | Bao et al. | |
| 5,201,729 A | 4/1993 | Hertzmann et al. | |
| 5,306,310 A | 4/1994 | Siebels | |
| 5,375,823 A | 12/1994 | Navas | |
| 5,415,661 A | 5/1995 | Holmes | |
| 5,433,739 A | 7/1995 | Sluijter | |
| 5,480,401 A | 1/1996 | Navas | |
| 5,496,318 A | 3/1996 | Howland et al. | |
| 5,514,130 A | 5/1996 | Baker | |
| 5,534,028 A | 7/1996 | Bao et al. | |
| 5,549,679 A | 8/1996 | Kuslich | |
| 5,562,736 A | 10/1996 | Ray | |
| 5,562,737 A | 10/1996 | Graf | |
| 5,645,597 A | 7/1997 | Krapiva | |

(List continued on next page.)

FOREIGN PATENT DOCUMENTS

| | | |
|---|---|---|
| WO | Wo 99/61084 | 12/1999 |
| WO | WO 00/62832 | 10/2000 |
| WO | WO 01/10316 | 2/2001 |
| WO | WO 01/12107 | 2/2001 |

\* cited by examiner

Primary Examiner—Corrine McDermott
Assistant Examiner—Thomas Sweet

(57) ABSTRACT

Devices and methods for treating a damaged intervertebral disc to reduce or eliminate associated back pain. The present invention provides disc reinforcement therapy (DRT) which involves implanting one or more reinforcement members in and preferably around the annulus of the disc. The reinforcement members may be used to stabilize the annulus and/or compresses a portion of the annulus so as to reduce a bulge and/or close a fissure. The implantable devices and associated delivery tools may incorporate heating capabilities to thermally treat the annular tissue. Alternatively or in combination, other devices may be specifically employed for such thermal treatment.

12 Claims, 66 Drawing Sheets

| | | | | | | |
|---|---|---|---|---|---|---|
| 5,645,599 A | 7/1997 | Samani | 6,126,682 A | 10/2000 | Sharkey et al. | |
| 5,672,175 A | 9/1997 | Martin | 6,132,465 A | 10/2000 | Ray et al. | |
| 5,674,295 A | 10/1997 | Ray | 6,135,999 A | 10/2000 | Fanton et al. | |
| 5,674,296 A | 10/1997 | Bryan | 6,162,217 A | 12/2000 | Kannenberg et al. | |
| 5,716,416 A | 2/1998 | Lin | 6,168,593 B1 | 1/2001 | Sharkey et al. | |
| 5,728,097 A | 3/1998 | Mathews | 6,187,043 B1 | 2/2001 | Ledergerber | |
| 5,755,797 A | 5/1998 | Baumgartner | 6,224,630 B1 | 5/2001 | Bao et al. | |
| 5,785,705 A | 7/1998 | Baker | 6,231,615 B1 | 5/2001 | Preissman | |
| 5,823,994 A | 10/1998 | Sharkey et al. | 6,245,107 B1 | 6/2001 | Ferree | |
| 5,824,093 A | 10/1998 | Ray et al. | 6,264,650 B1 | 7/2001 | Hovda et al. | |
| 5,876,404 A | 3/1999 | Zucherman et al. | 6,264,695 B1 | 7/2001 | Stoy | |
| 5,919,235 A | 7/1999 | Husson et al. | 6,277,112 B1 | 8/2001 | Underwood et al. | |
| 5,951,555 A | 9/1999 | Rehak et al. | 6,280,475 B1 | 8/2001 | Bao et al. | |
| 5,954,716 A | 9/1999 | Sharkey et al. | 6,402,750 B1 | 6/2002 | Atkinson et al. | |
| 5,976,186 A | 11/1999 | Apgar | 6,425,919 B1 | 7/2002 | Lambrecht | |
| 5,980,504 A | 11/1999 | Sharkey et al. | 6,428,576 B1 | 8/2002 | Haldimann | |
| 5,984,925 A | 11/1999 | Bao et al. | 6,540,741 B1 | 4/2003 | Underwood et al. | |
| 5,989,291 A | 11/1999 | Ralph et al. | 6,579,291 B1 | 6/2003 | Keith et al. | |
| 6,004,320 A | 12/1999 | Casscells et al. | 6,626,916 B1 * | 9/2003 | Yeung et al. | 606/139 |
| 6,007,533 A | 12/1999 | Casscells et al. | 6,712,853 B2 * | 3/2004 | Kuslich | 623/17.16 |
| 6,007,570 A | 12/1999 | Sharkey et al. | 6,736,815 B2 * | 5/2004 | Ginn | 606/60 |
| 6,022,376 A | 2/2000 | Assell et al. | 2002/0095154 A1 | 7/2002 | Atkinson | |
| 6,068,628 A | 5/2000 | Fanton et al. | 2002/0111688 A1 | 8/2002 | Cauthen | |
| 6,073,051 A | 6/2000 | Sharkey et al. | 2002/0120037 A1 | 8/2002 | Cauthen | |
| 6,095,149 A | 8/2000 | Sharkey et al. | 2002/0123807 A1 | 9/2002 | Cauthen | |
| 6,099,514 A | 8/2000 | Sharkey et al. | 2002/0151980 A1 | 10/2002 | Cauthen | |
| 6,110,210 A | 8/2000 | Norton et al. | 2002/0188291 A1 * | 12/2002 | Uchida et al. | 606/41 |
| 6,122,549 A | 9/2000 | Sharkey et al. | 2003/0045937 A1 * | 3/2003 | Ginn | 623/17.11 |

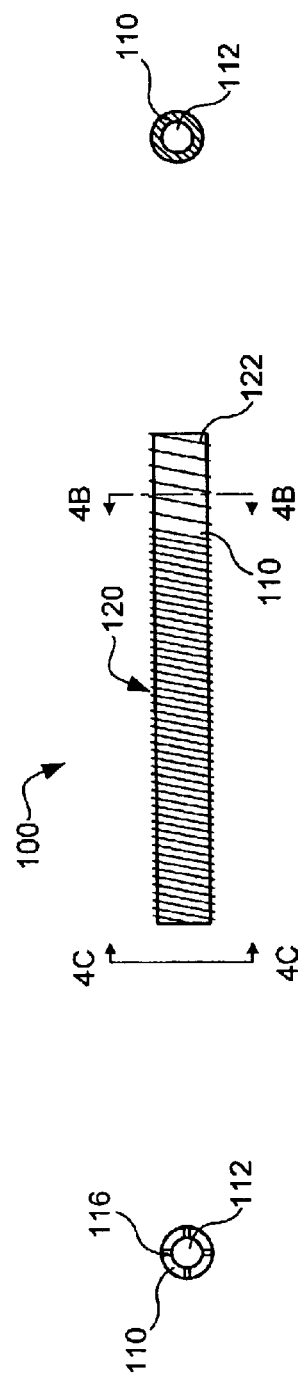

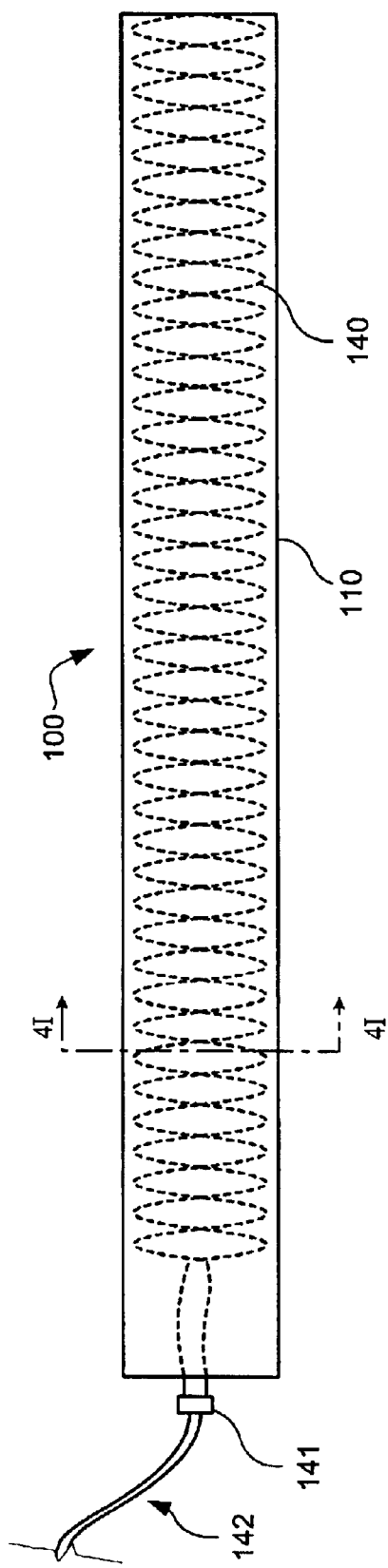
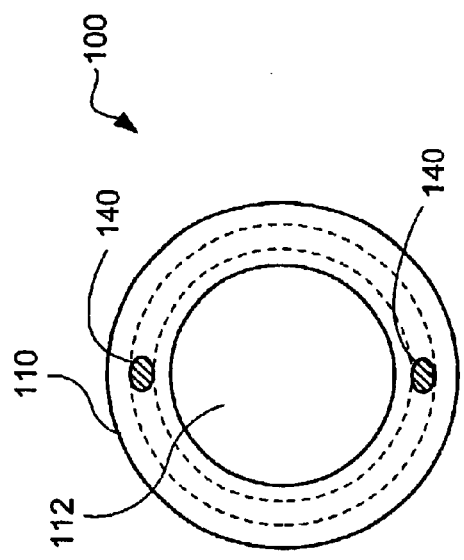
FIG. 4H
FIG. 4I

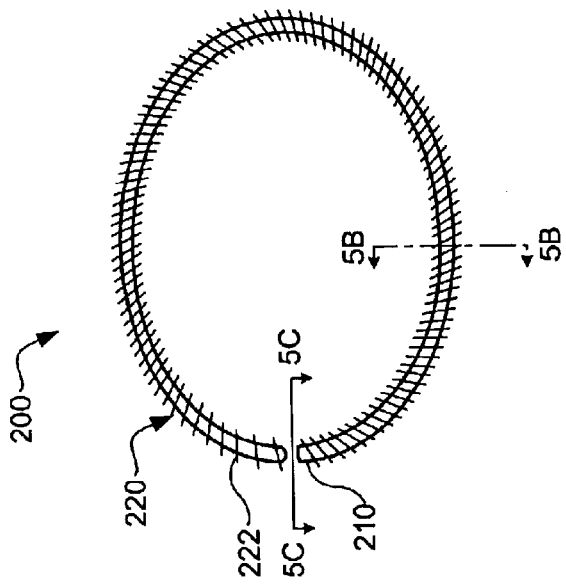

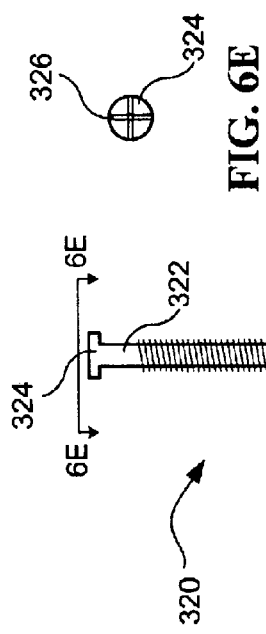
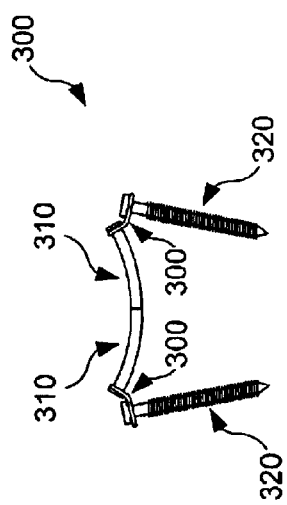
FIG. 6E
FIG. 6D
FIG. 6H
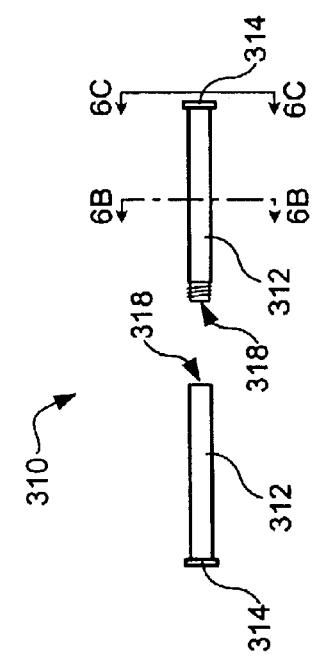
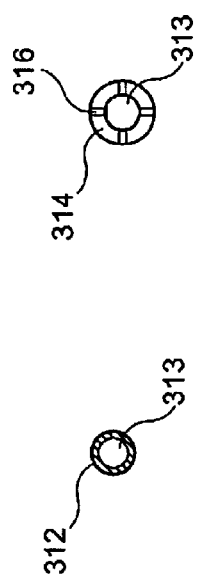
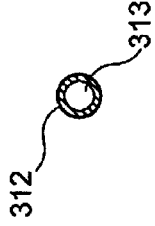
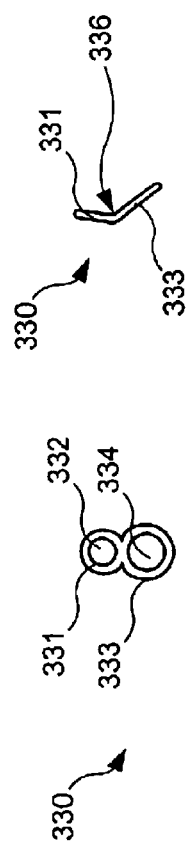
FIG. 6A
FIG. 6C
FIG. 6G
FIG. 6B
FIG. 6F

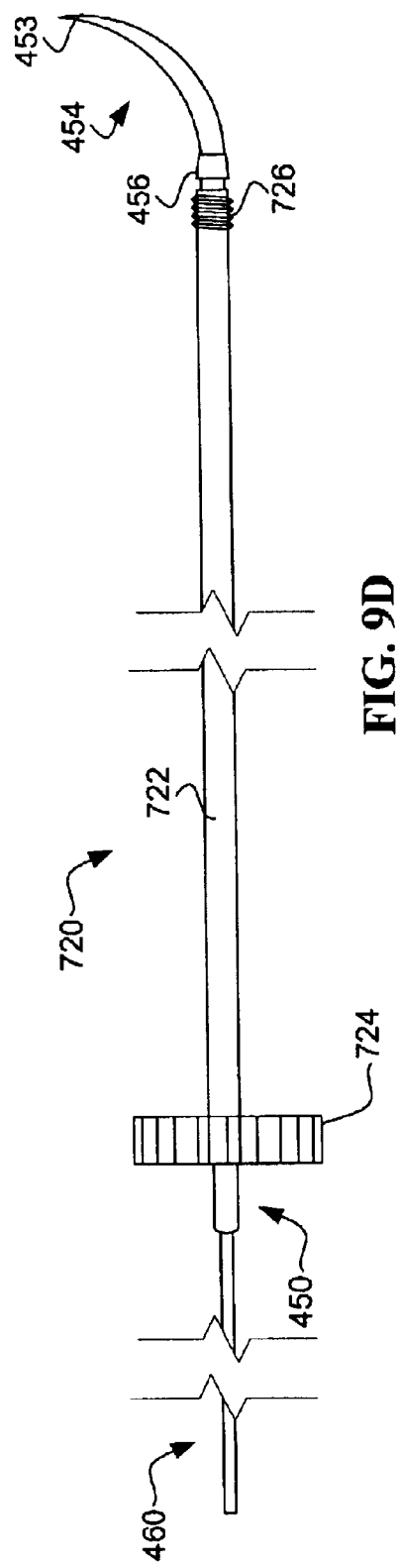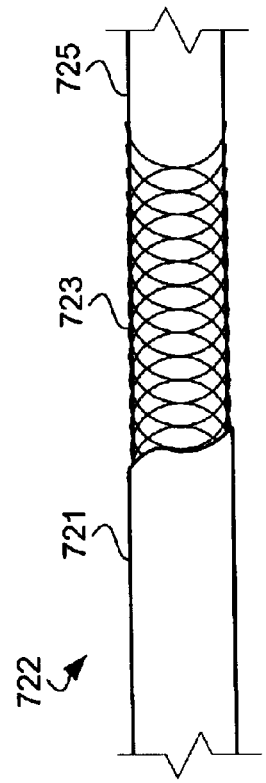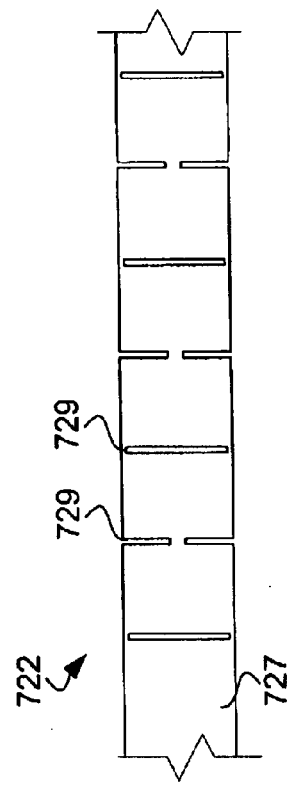
FIG. 9D
FIG. 9E
FIG. 9F

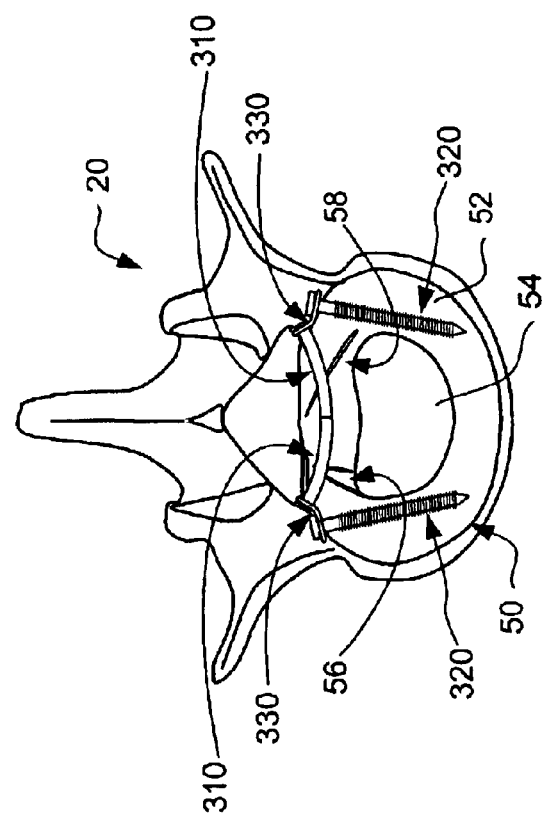
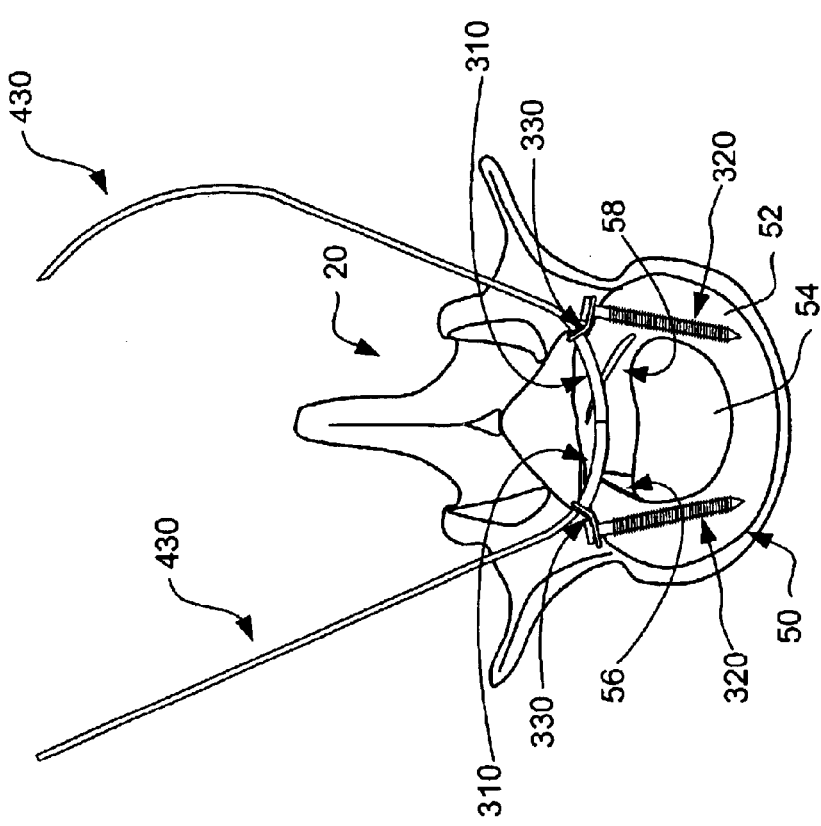
FIG. 11H
FIG. 11G

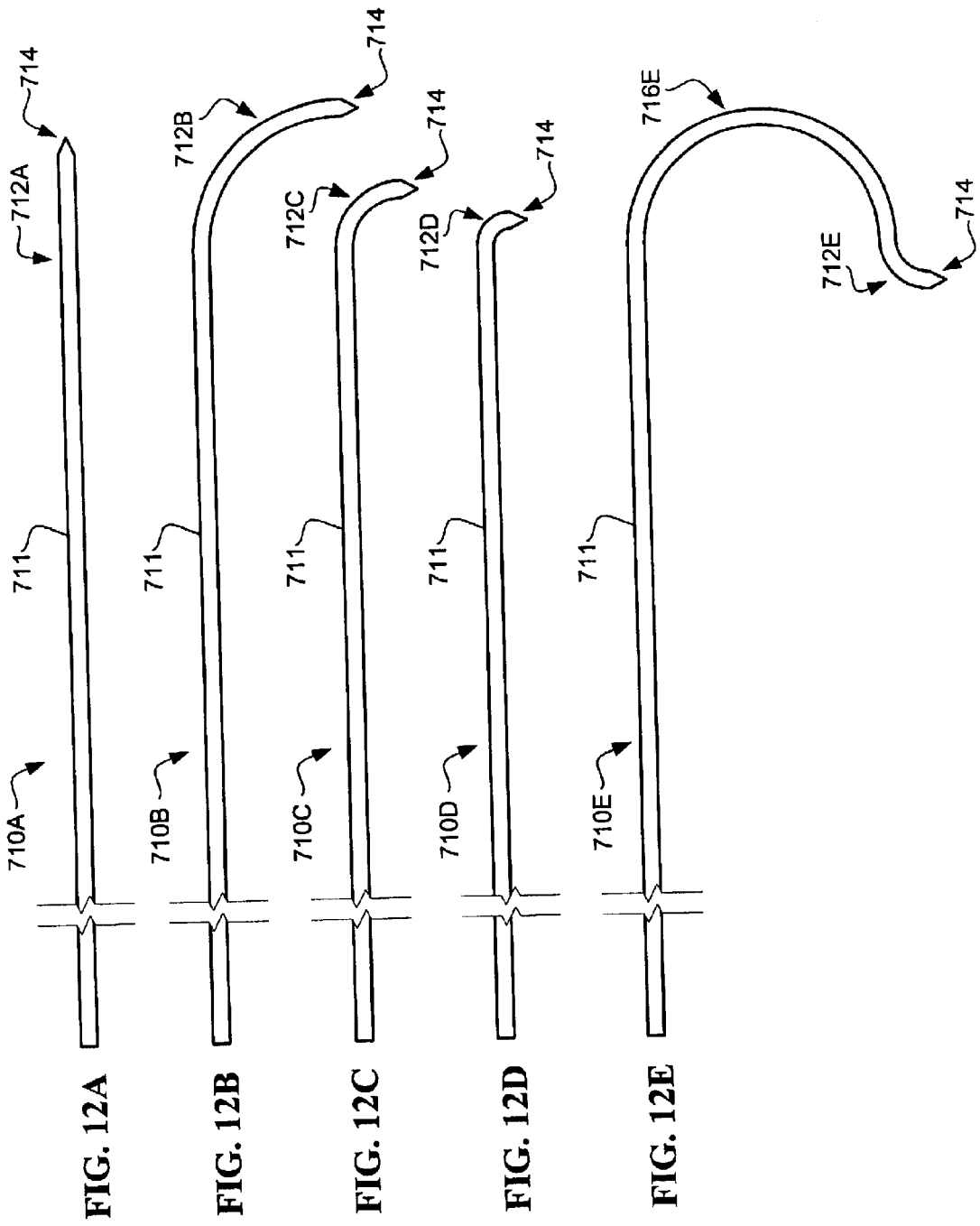

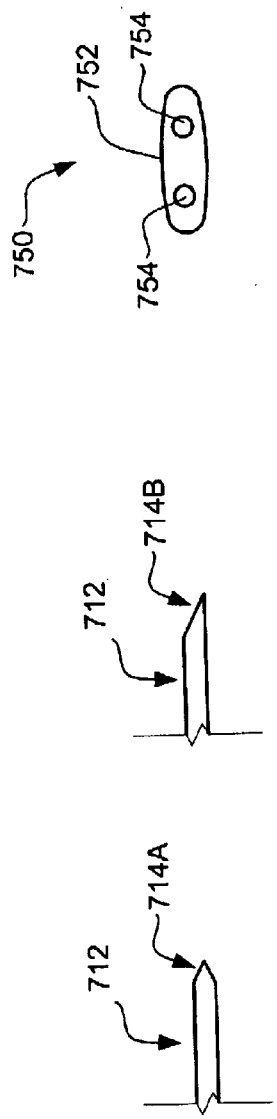
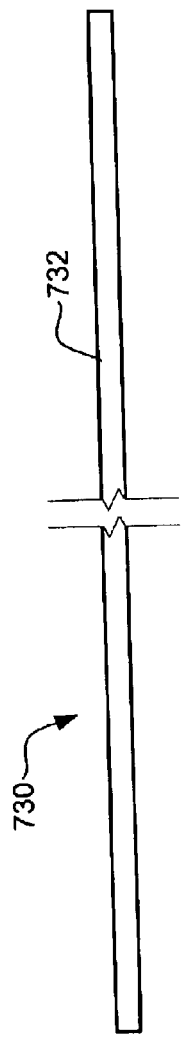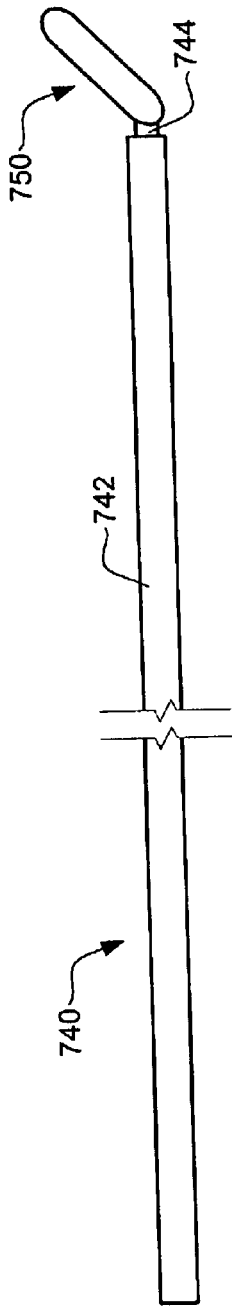
FIG. 12F FIG. 12G FIG. 13 FIG. 14 FIG. 15

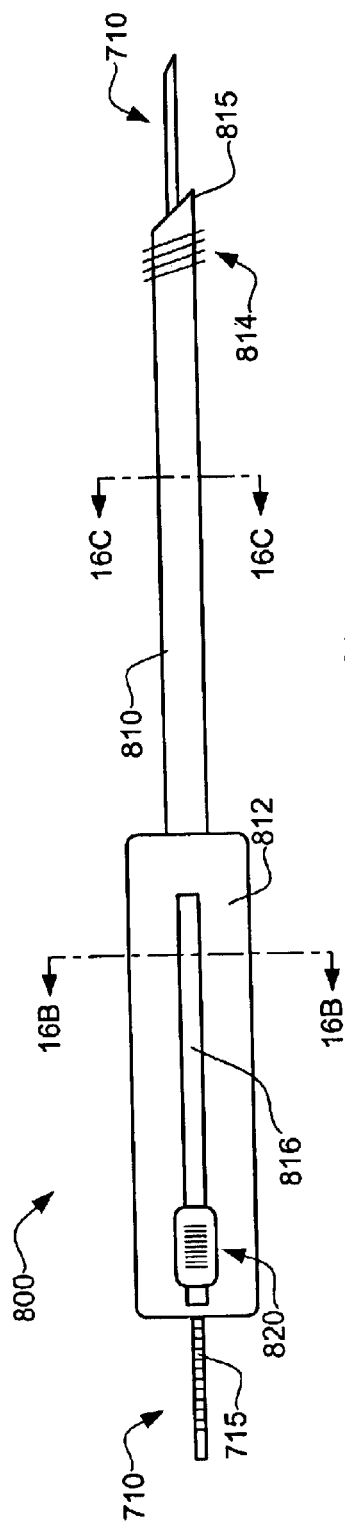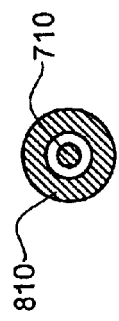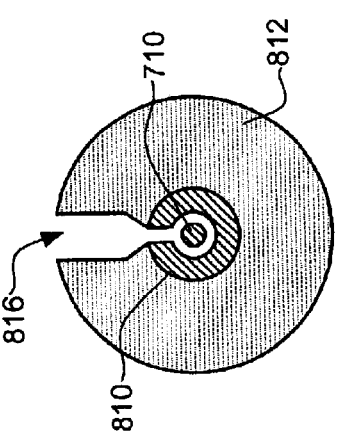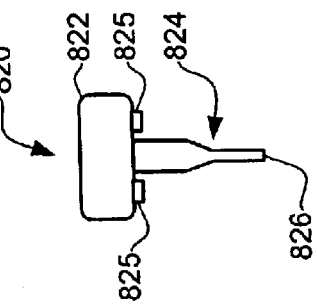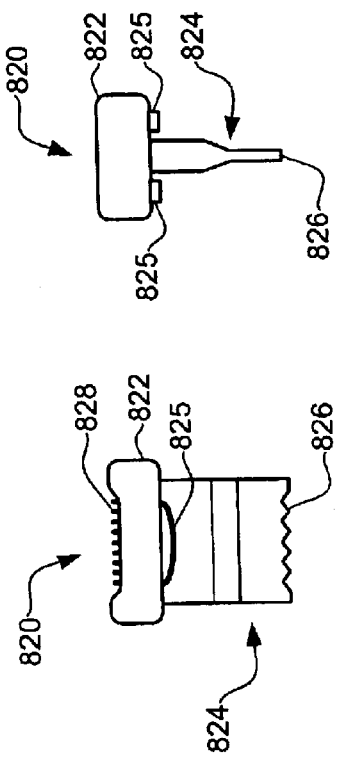
FIG. 16A
FIG. 16B
FIG. 16C
FIG. 16D
FIG. 16E

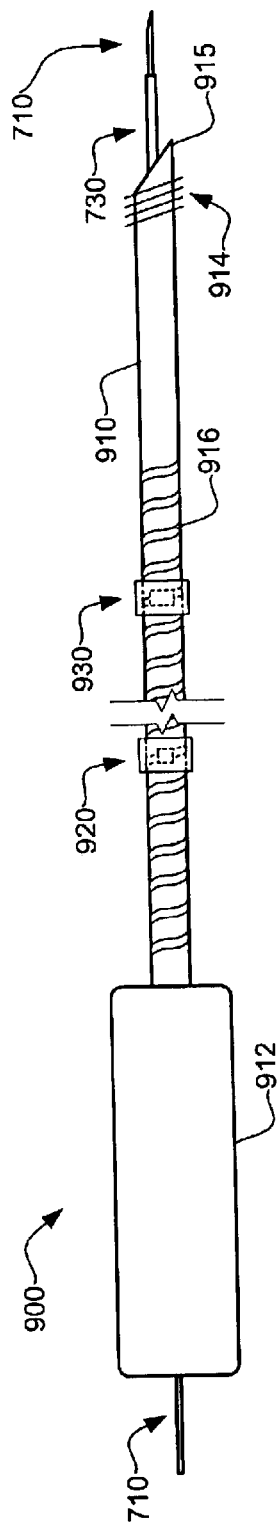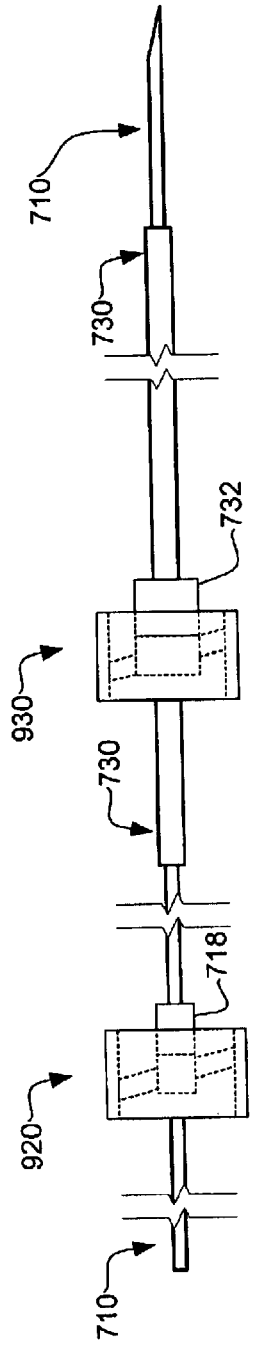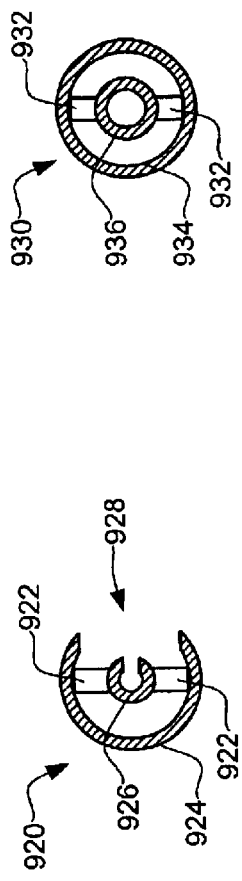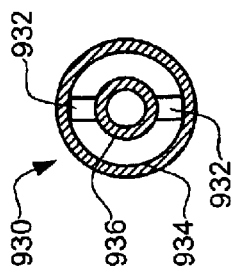
FIG. 17A
FIG. 17B
FIG. 17C
FIG. 17D

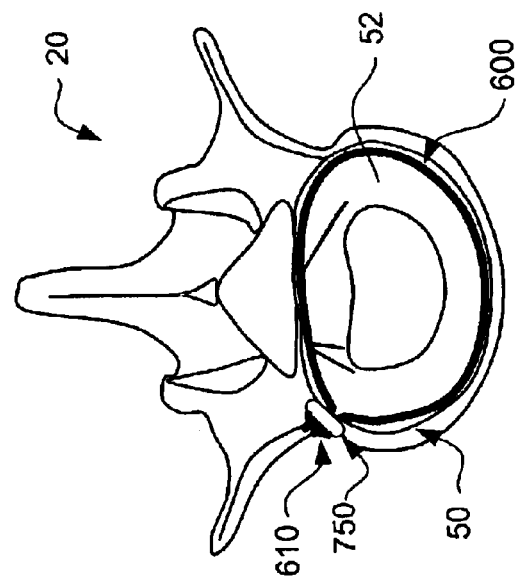
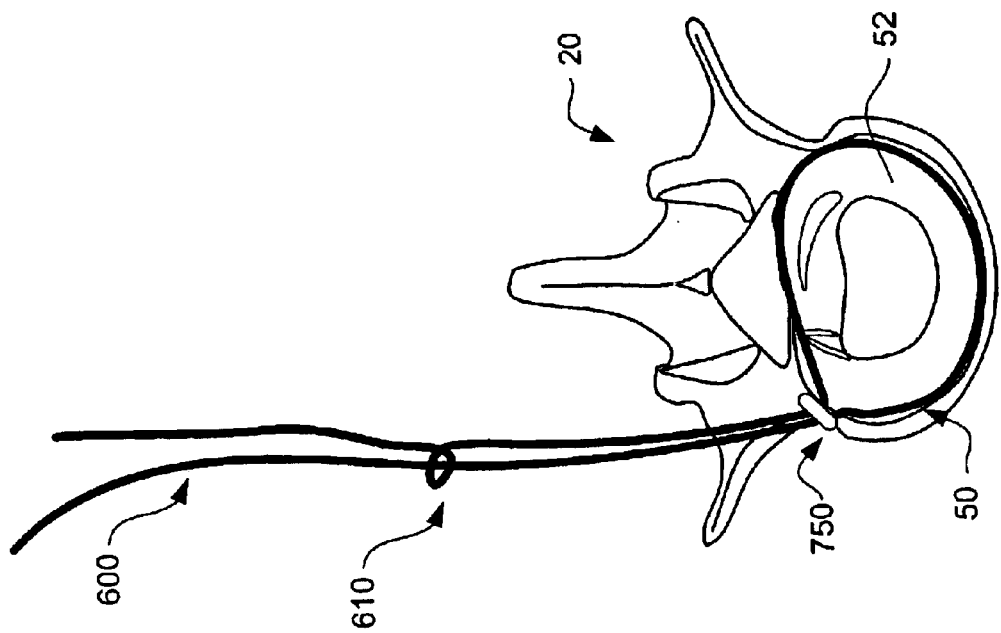
FIG. 18J
FIG. 18I

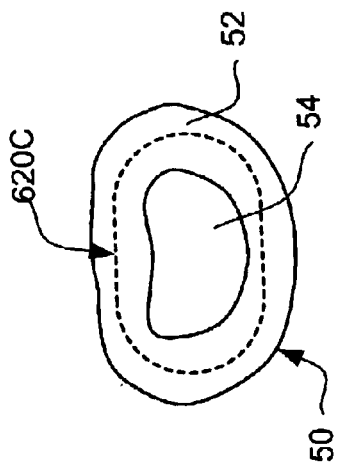
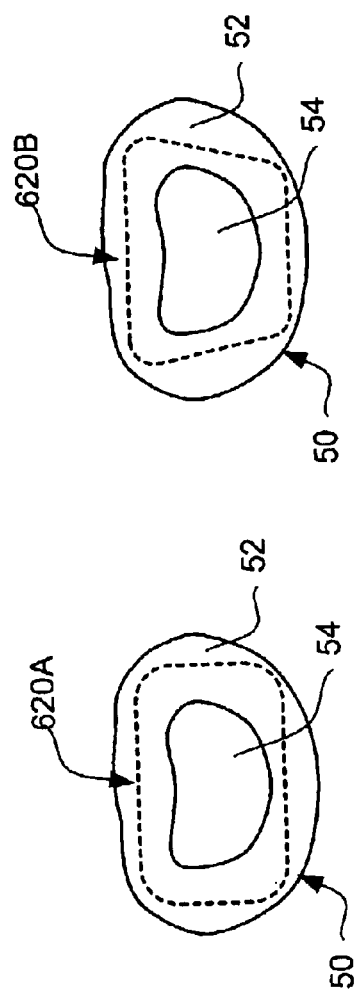
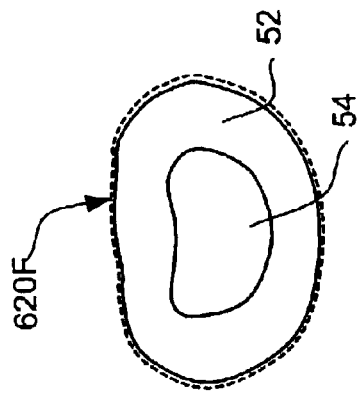
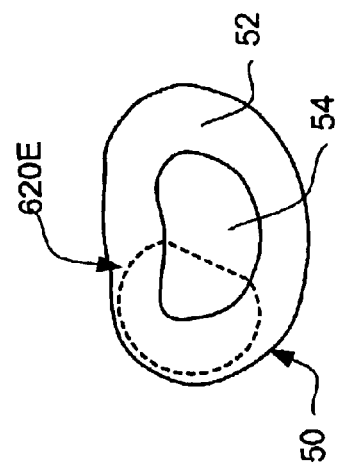
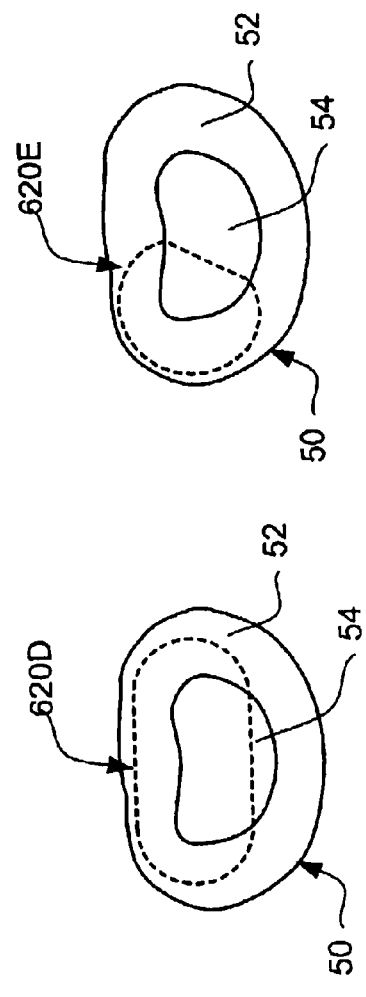

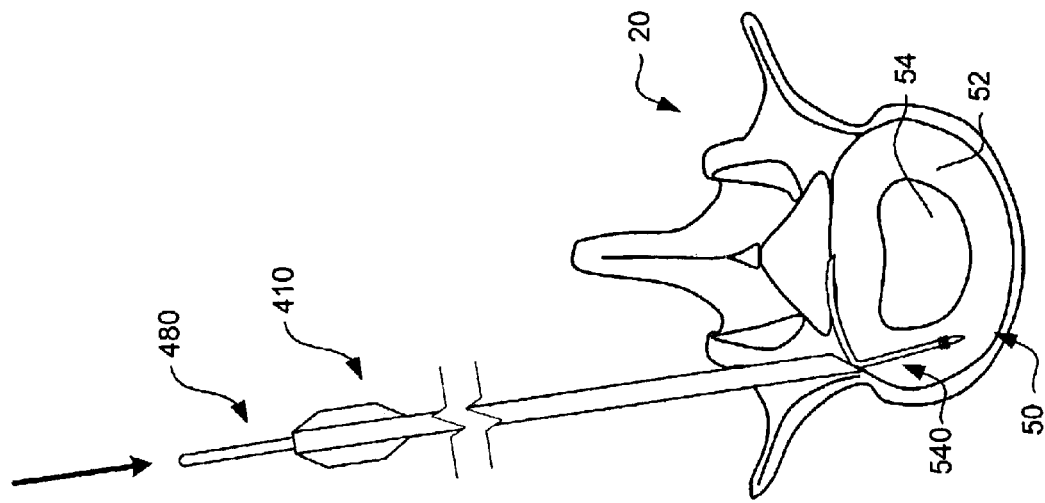
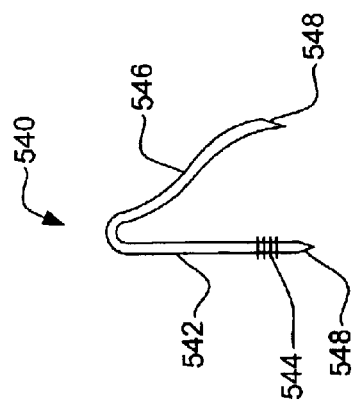
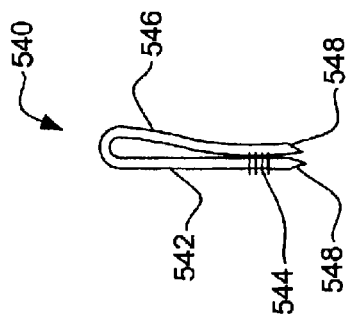

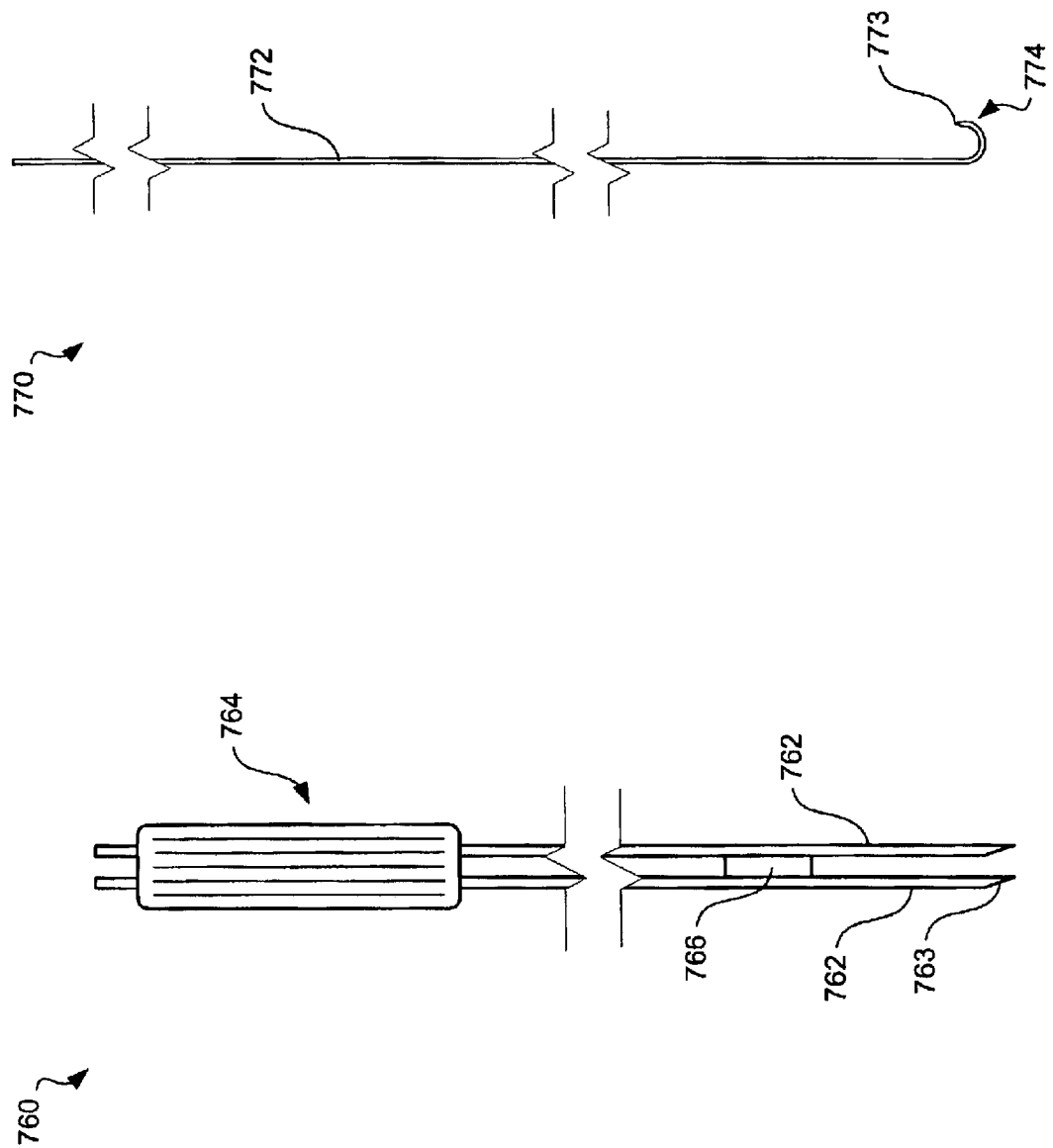

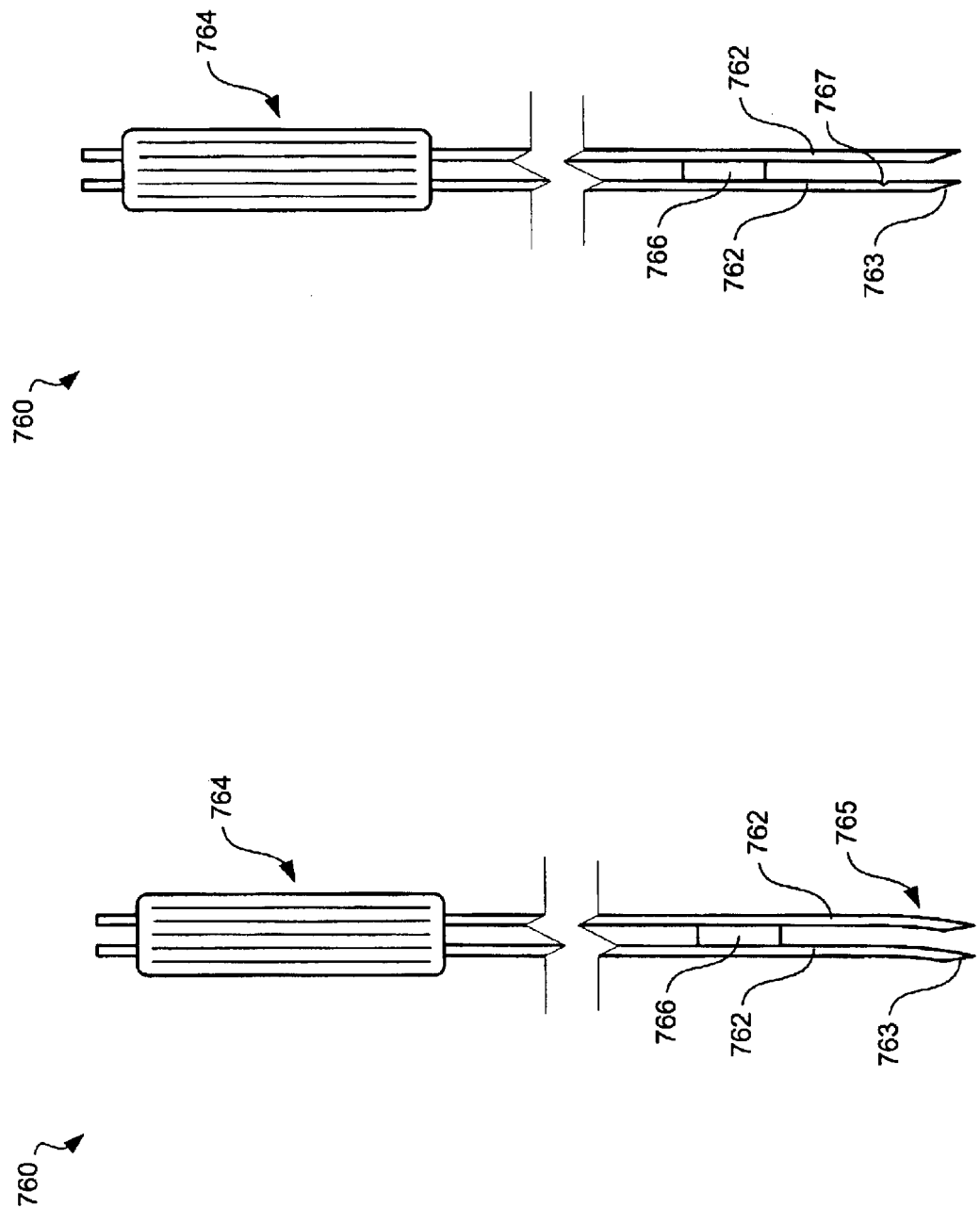

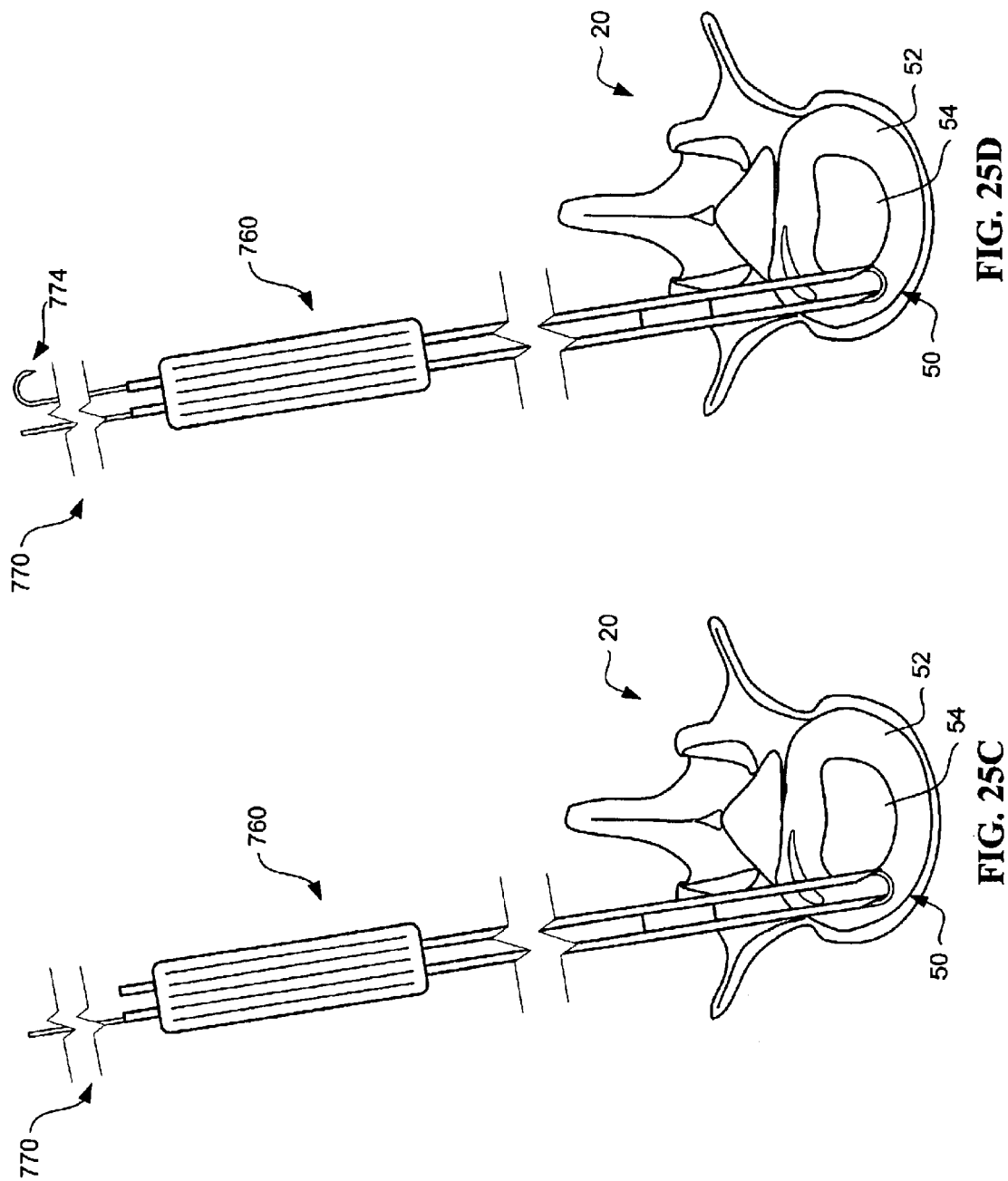

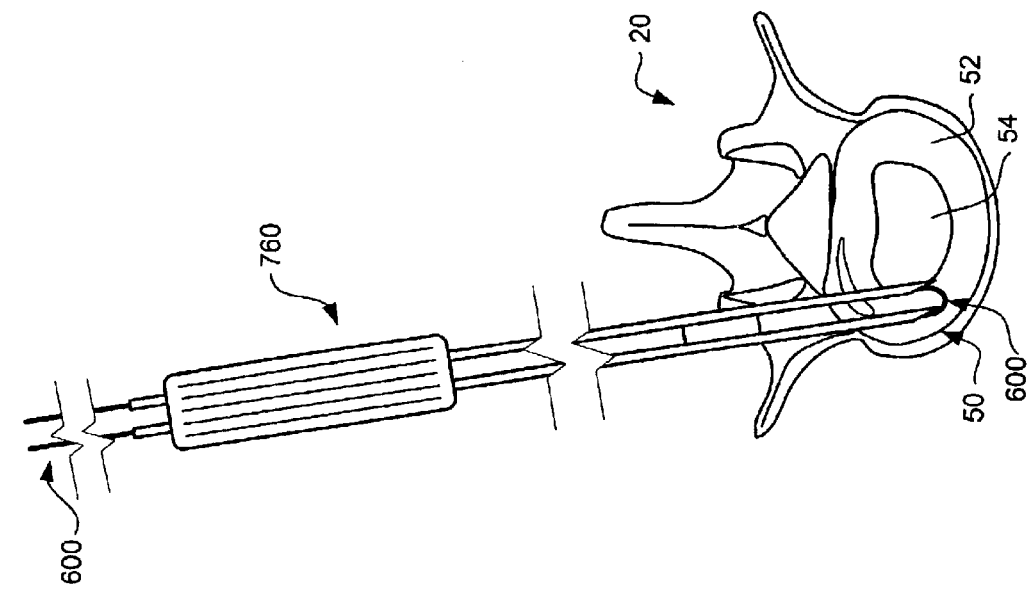
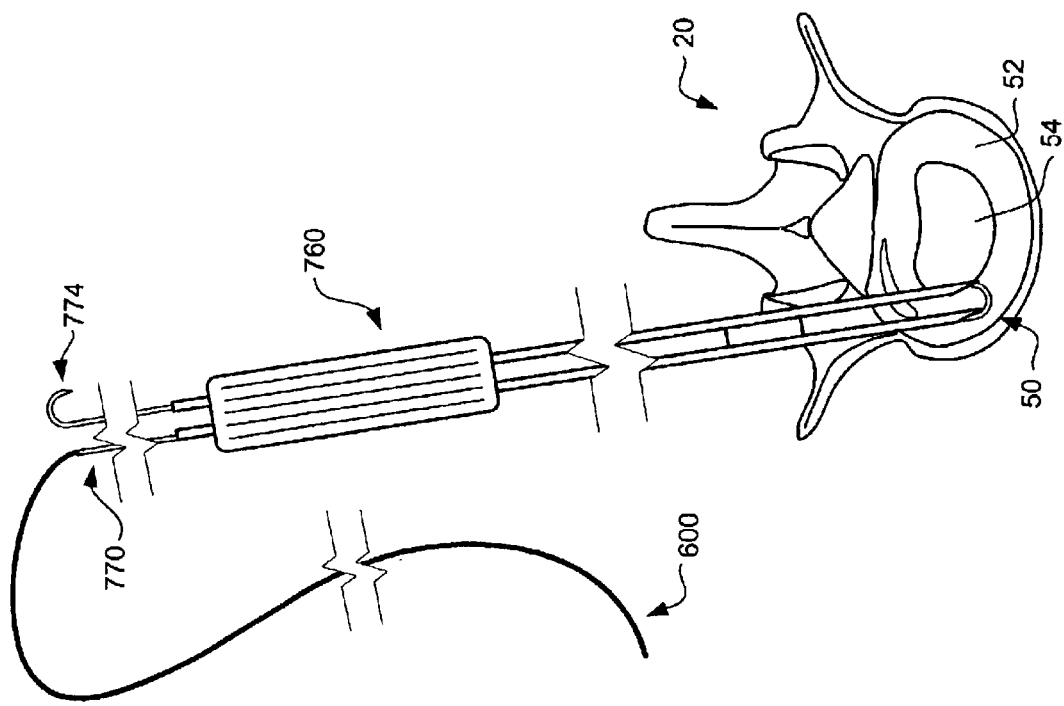

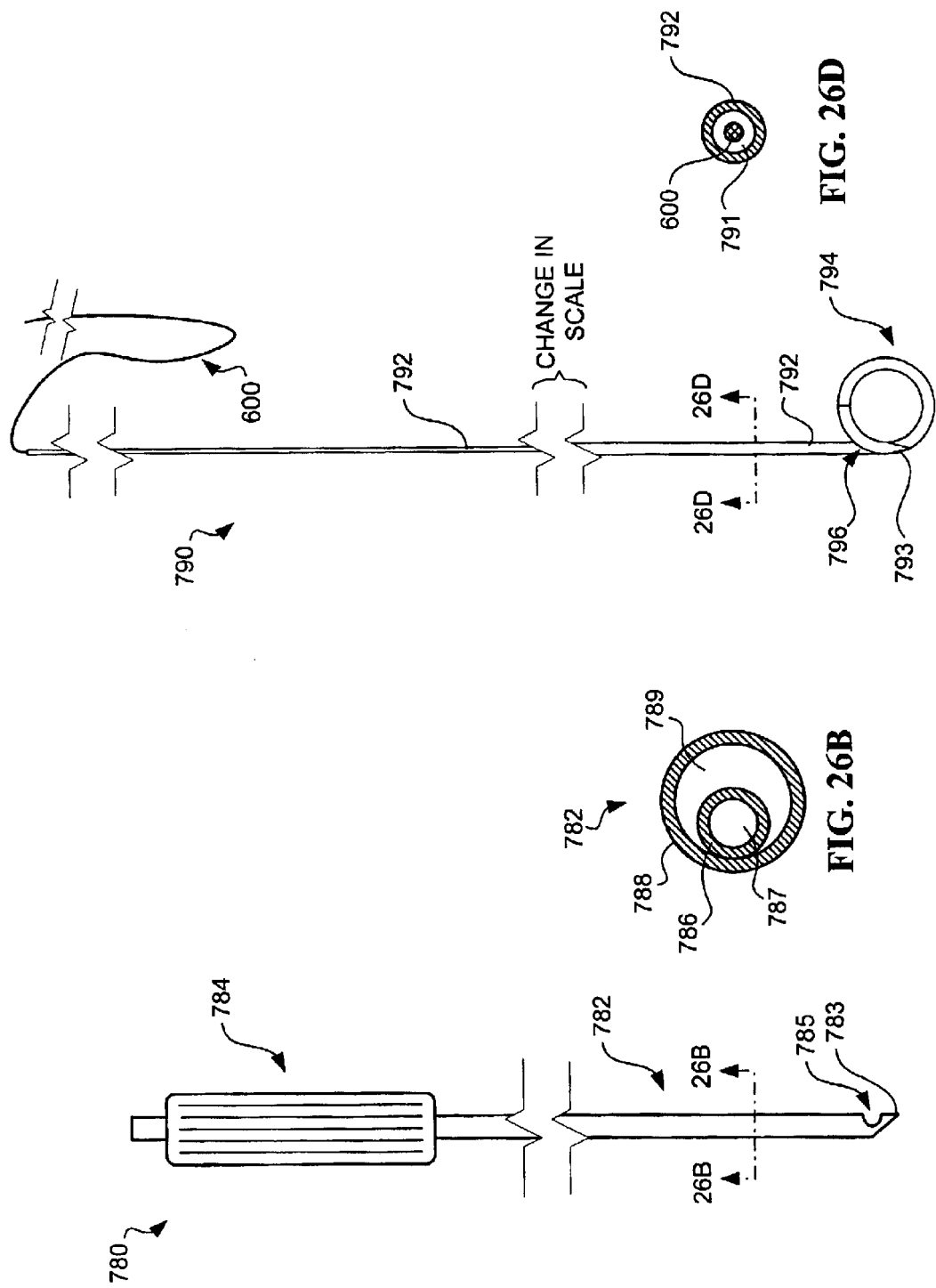

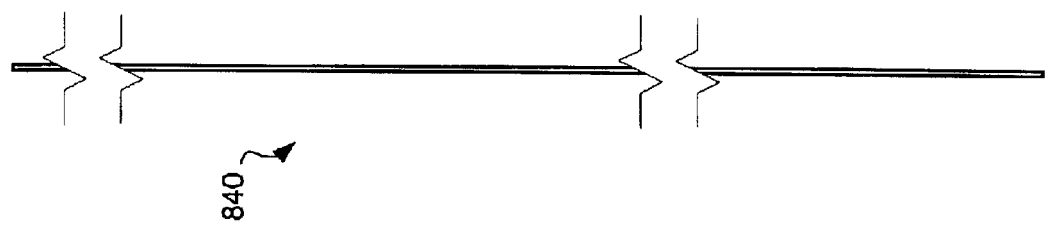
FIG. 26G
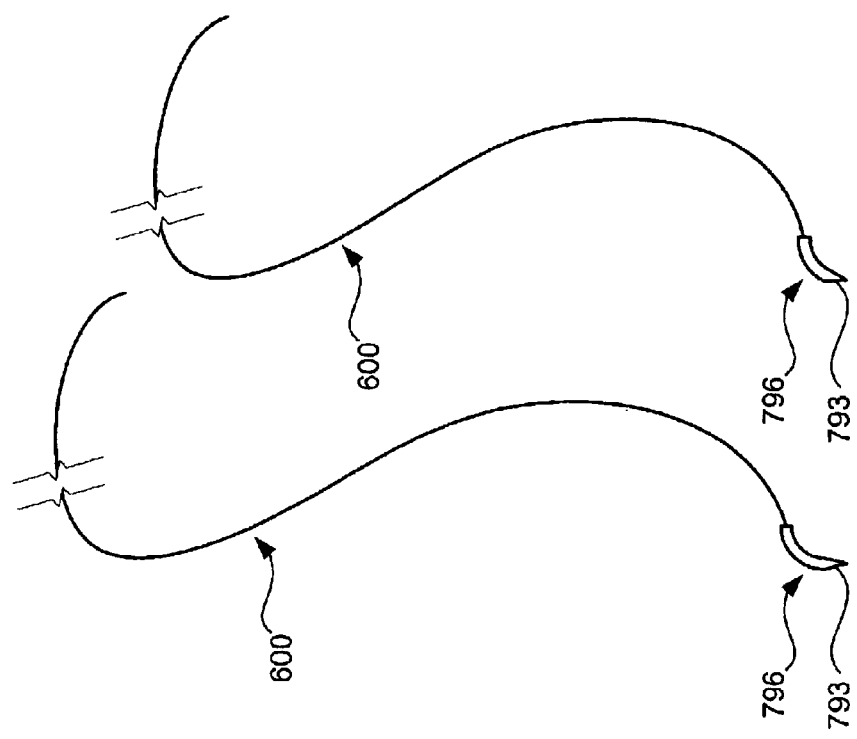
FIG. 26F
FIG. 26E

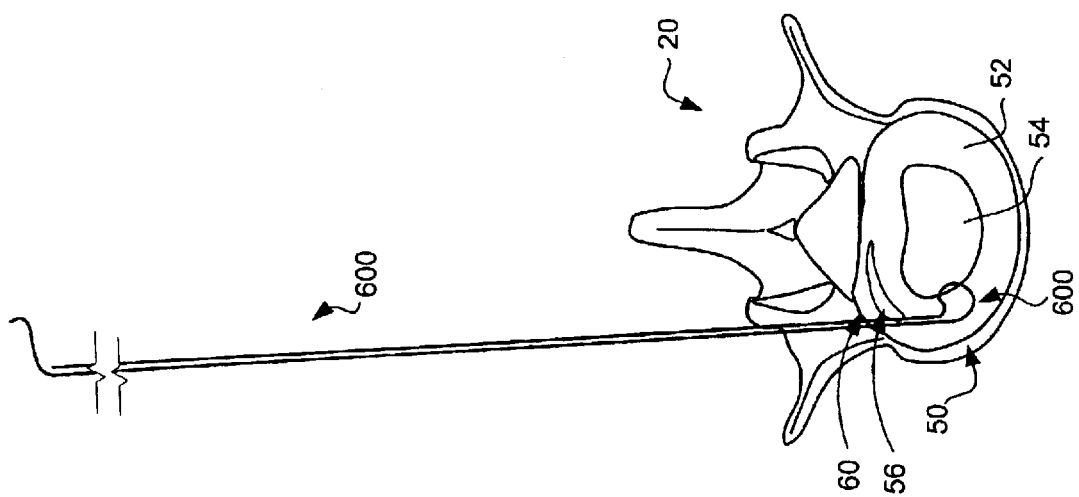
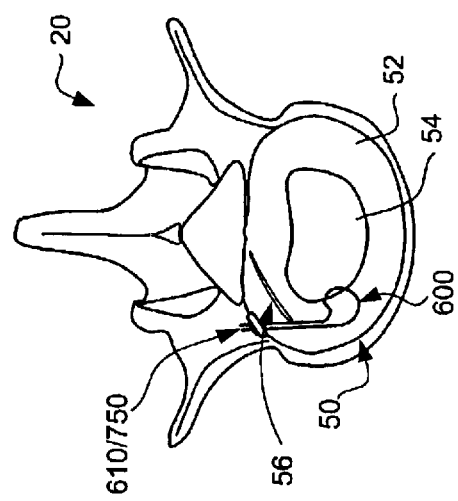
FIG. 27E
FIG. 27F

DEVICES AND METHODS FOR ANNULAR REPAIR OF INTERVERTEBRAL DISCS

CROSS REFERENCE TO RELATED APPLICATIONS

The present application claims the benefit of U.S. Provisional Application No. 60/368,108 filed Mar. 26, 2002 entitled DEVICES AND METHODS FOR THE TREATMENT OF SPINAL DISORDERS, the entire disclosure of which is incorporated herein by reference. The present application is a continuation-in-part of and claims priority to the following U.S. patent applications: U.S. patent application Ser. No. 10/055780, filed Jan. 22, 2002, now U.S. Pat. No. 6,689,125 entitled DEVICES AND METHODS FOR THE TREATMENT OF SPINAL DISORDERS, which claims the benefit of U.S. Provisional Application No. 60/263,343 filed Jan. 22, 2001, entitled DEVICES AND METHODS FOR THE TREATMENT OF SPINAL DISORDERS; U.S. patent application Ser. No. 09/685,401, filed Oct. 10, 2000, now U.S. Pat. No. 6,579,291 entitled DEVICES AND METHODS FOR THE TREATMENT OF SPINAL DISORDERS: and U.S. patent application Ser. No. 10/093,990, filed Mar. 7, 2002, entitled DEVICES AND METHODS FOR THE TREATMENT OF SPINAL DISORDERS, which is a continuation of U.S. patent application Ser. No. 09/542,972, filed Apr. 4, 2000, entitled DEVICES AND METHODS FOR THE TREATMENT OF SPINAL DISORDERS, now issued as U.S. Pat. No. 6,402,750.

FIELD OF THE INVENTION

The present invention generally relates to devices and methods for the repair of intervertebral discs. Specifically, the present invention relates to devices and methods for the treatment of spinal disorders associated with the annulus of an intervertebral disc.

BACKGROUND OF THE INVENTION

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Some forms of back pain are muscular in nature and may be simply treated by rest, posture adjustments and painkillers. For example, some forms of lower back pain (LBP) are very common and may be caused by unusual exertion or injury. Unusual exertion such has heavy lifting or strenuous exercise may result in back strain such as a pulled muscle, sprained muscle, sprained ligament, muscle spasm, or a combination thereof. An injury caused by falling down or a blow to the back may cause bruising. These forms of back pain are typically non-chronic and may be self-treated and cured in a few days or weeks.

Other types of non-chronic back pain may be treated by improvements in physical condition, posture and/or work conditions. For example, being pregnant, obese or otherwise significantly overweight may cause LBP. A mattress that does not provide adequate support may cause back pain in the morning. Working in an environment lacking good ergonomic design may also cause back pain. In these instances, the back pain may be cured by eliminating the culprit cause. Whether it is excess body weight, a bad mattress, or a bad office chair, these forms of back pain are readily treated.

However, some forms of back pain are the result of disorders directly related to the spinal column, which are not readily treated. While some pain-causing spinal disorders may be due to facet joint degradation or degradation of individual vertebral masses, disorders associated with the intervertebral discs are predominantly affiliated with chronic back pain (referred to as disc related pain). The exact origin of disc related pain is often uncertain, and although some episodes of disc related pain may be eased with conservative treatments such as bed-rest and physical therapy, future episodes of disc related pain are likely to occur periodically.

There are a number of suspected causes of disc related pain, and in any given patient, one or more of these causes may be present. However, the ability to accurately diagnose a specific cause or locus of pain is currently difficult. Because of this uncertainty, many of the causes of disc related pain are often lumped together and referred to as degenerative disc disease (DDD).

A commonly suspected source of disc related pain is physical impingement of the nerve roots emanating from the spinal cord. Such nerve root impingement may have a number of different underlying causes, but nerve root impingement generally results from either a disc protrusion or a narrowing of the intervertebral foramina (which surround the nerve roots).

As a person ages, their intervertebral discs become progressively dehydrated and malnourished. Together with continued stressing, the disc begins to degenerate. With continued degeneration, or an excessive stressing event, the annulus fibrosus of the disc may tear, forming one or more fissures (also referred to as fractures). Such fissures may progress to larger tears which allow the gelatinous material of the nucleus pulposus to flow out of the nucleus and into the outer aspects of the annulus. The flow of the nucleus pulposus to the outer aspects of the annulus may cause a localized bulge.

When bulging of the annulus occurs in the posterior portions of the disc, the nerve roots may be directly and physically impinged by the bulge. In more extreme or progressed instances of annular tears, the nuclear material may escape, additionally causing chemical irritation of the nerve roots. Depending on the cause and nature of the disc protrusion, the condition may be referred to as a disc stenosis, a disc bulge, a herniated disc, a prolapsed disc, a ruptured disc, or, if the protrusion separates from the disc, a sequestered disc.

Dehydration and progressive degeneration of the disc also leads to thinning of the disc. As the height of the disc reduces, the intervertebral foraminae become narrow. Because the nerve roots pass through the intervertebral foraminae, such narrowing may mechanically entrap the nerve roots. This entrapment can cause direct mechanical compression, or may tether the roots, allowing them to be excessively tensioned during body movements.

Nerve root impingement most often occurs in the lumbar region of the spinal column since the lumbar discs bear significant vertical loads relative to discs in other regions of the spine. In addition, disc protrusions in the lumbar region typically occur posteriorly because the annulus fibrosus is radially thinner on the posterior side than on the anterior side and because normal posture places more compression on the posterior side. Posterior protrusions are particularly problematic since the nerve roots are posteriorly positioned relative to the intervertebral discs. Lower back pain due to nerve root irritation not only results in strong pain in the region of the back adjacent the disc, but may also cause sciatica, or pain radiating down one or both legs. Such pain may also be aggravated by such subtle movements as coughing, bending over, or remaining in a sitting position for an extended period of time.

Another suspected source of disc related back pain is damage and irritation to the small nerve endings which lie in close proximity to or just within the outer aspects of the annulus of the discs. Again, as the disc degenerates and is subjected to stressing events, the annulus fibrosus may be damaged forming fissures. While these fissures can lead to pain via the mechanisms described above, they may also lead to pain emanating from the small nerve endings in or near the annulus, due to mechanical or chemical irritation at the sites of the fissures. The fissures may continue to irritate the small nerve endings, as their presence cause the disc to become structurally weaker, allowing for more localized straining around the fissures. This results in more relative motion of edges of the fissures, increasing mechanical irritation. Because it is believed that these fissures have only limited healing ability once formed, such irritation may only become progressively worse.

A common treatment for a disc protrusion is discectomy, a procedure wherein the protruding portion of the disc is surgically removed. However, discectomy procedures have an inherent risk since the portion of the disc to be removed is immediately adjacent the nerve root and any damage to the nerve root is clearly undesirable. Furthermore, discectomy procedures are not always successful long term because scar tissue may form and/or additional disc material may subsequently protrude from the disc space as the disc deteriorates further. The recurrence of a disc protrusion may necessitate a repeat discectomy procedure, along with its inherent clinical risks and less than perfect long term success rate. Thus, a discectomy procedure, at least as a stand-alone procedure, is clearly not an optimal solution.

Discectomy is also not a viable solution for DDD when no disc protrusion is involved. As mentioned above, DDD causes the entire disc to degenerate, narrowing of the intervertebral space, and shifting of the load to the facet joints. If the facet joints carry a substantial load, the joints may degrade over time and be a different cause of back pain. Furthermore, the narrowed disc space can result in the intervertebral foramina surrounding the nerve roots to directly impinge on one or more nerve roots. Such nerve impingement is very painful and cannot be corrected by a discectomy procedure. Still furthermore, discectomy does not address pain caused by the fissures which may cause direct mechanical irritation to the small nerve endings near or just within the outer aspect of the annulus of a damaged disc.

As a result, spinal fusion, particularly with the assistance of interbody fusion cages, has become a preferred secondary procedure, and in some instances, a preferred primary procedure. Spinal fusion involves permanently fusing or fixing adjacent vertebrae. Hardware in the form of bars, plates, screws and cages may be utilized in combination with bone graft material to fuse adjacent vertebrae. Spinal fusion may be performed as a stand-alone procedure or may be performed in combination with a discectomy procedure. By placing the adjacent vertebrae in their nominal position and fixing them in place, relative movement therebetween may be significantly reduced and the disc space may be restored to its normal condition. Thus, theoretically, aggravation caused by relative movement between adjacent vertebrae may be reduced if not eliminated.

However, the success rate of spinal fusion procedures is certainly less than perfect for a number of different reasons, none of which are well understood. In addition, even if spinal fusion procedures are initially successful, they may cause accelerated degeneration of adjacent discs since the adjacent discs must accommodate a greater degree of motion. The degeneration of adjacent discs simply leads to the same problem at a different anatomical location, which is clearly not an optimal solution. Furthermore, spinal fusion procedures are invasive to the disc, risk nerve damage and, depending on the procedural approach, either technically complicated (endoscopic anterior approach), invasive to the bowel (surgical anterior approach), or invasive to the musculature of the back (surgical posterior approach).

Another procedure that has been less than clinically successful is total disc replacement with a prosthetic disc. This procedure is also very invasive to the disc and, depending on the procedural approach, either invasive to the bowel (surgical anterior approach) or invasive to the musculature of the back (surgical posterior approach). In addition, the procedure may actually complicate matters by creating instability in the spine, and the long term mechanical reliability of prosthetic discs has yet to be demonstrated.

Many other medical procedures have been proposed to solve the problems associated with disc protrusions. However, many of the proposed procedures have not been clinically proven and some of the allegedly beneficial procedures have controversial clinical data. From the foregoing, it should be apparent that there is a substantial need for improvements in the treatment of spinal disorders, particularly in the treatment of disc related pain associated with a damaged or otherwise unhealthy disc.

SUMMARY OF THE INVENTION

The present invention addresses this need by providing improved devices and methods for the treatment of spinal disorders. The improved devices and methods of the present invention specifically address disc related pain, particularly in the lumbar region, but may have other significant applications not specifically mentioned herein. For purposes of illustration only, and without limitation, the present invention is discussed in detail with reference to the treatment of damaged discs in the lumbar region of the adult human spinal column.

As will become apparent from the following detailed description, the improved devices and methods of the present invention may reduce if not eliminate back pain while maintaining near normal anatomical motion. Specifically, the present invention provides disc reinforcement devices to reinforce a damaged disc, while permitting relative movement of the vertebrae adjacent the damaged disc. The devices of the present invention are particularly well suited for minimally invasive methods of implantation.

The reinforcement devices of the present invention may provide three distinct functions. Firstly, the reinforcement devices may mechanically stabilize and strengthen the disc to minimize if not eliminate chronic irritation of nerve roots and nerves around the periphery of the disc annulus. Secondly, the reinforcement devices may radially and/or circumferentially compress the disc to close fissures, fractures and tears, thereby preventing the ingress of nerves as well as potentially facilitating healing. Thirdly, the reinforcement devices may be used to stabilize the posterior disc after a discectomy procedure in order to reduce the need for re-operation.

In an exemplary embodiment, the present invention provides disc reinforcement therapy (DRT) in which a reinforcement member is implanted in the annulus of an intervertebral disc. The implantation method may be performed by a percutaneous procedure or by a minimally invasive surgical procedure. The present invention provides a number or tools to facilitate percutaneous implantation. One or more reinforcement members may be implanted, for example, posteriorly, anteriorly, and/or laterally, and may be oriented circumferentially or radially. As such, the reinforcement members may be used to stabilize the annulus and/or compresses a portion of the annulus so as to reduce a bulge and/or close a fissure.

In other embodiments, the implantable devices and associated delivery tools may incorporate heating capabilities to thermally treat the annular tissue. Alternatively or in combination, other devices may be specifically employed for such thermal treatment, and such thermal treatment may be applied by a device that is temporarily inserted into the annulus, or the thermal treatment may be applied by a chronically implanted device, either acutely or chronically.

BRIEF DESCRIPTION OF THE DRAWINGS

FIGS. 4A–4M schematically illustrate various features that may be incorporated into a straight or curved reinforcement member in accordance with an embodiment of the present invention;

FIGS. 5A–5C schematically illustrate a circumferential reinforcement member in accordance with an embodiment of the present invention;

FIGS. 6A–6H schematically illustrate components of a reinforcement member in accordance with an embodiment of the present invention;

FIGS. 9A–9F illustrate tools of the present invention for implanting the reinforcement member shown in FIG. 3C in accordance with the method illustrated in FIGS. 10A–10H;

FIGS. 11A–11H illustrate a method for implanting the reinforcement member shown in FIG. 3D in accordance with an embodiment of the present invention;

FIGS. 12A–12G and 13–15 illustrate various tools of the present invention for implanting the reinforcement member shown in FIGS. 3E and 3F in accordance with the method illustrated in FIGS. 18A–18L;

FIGS. 16A–16E illustrate a column support and advancement device for use with the tools illustrated in FIGS. 12A–12G and 13;

FIGS. 17A–17D illustrate an alternative column support and advancement device for use with the tools illustrated in FIGS. 12A–12G and 13;

FIGS. 18A–18L illustrate a method for implanting the reinforcement member shown in FIGS. 3E and 3F in accordance with an embodiment of the present invention;

FIGS. 19A–19F illustrate various possible implant orientations of the reinforcement member shown in FIGS. 3E and 3F;

FIGS. 21A–21C illustrate a reinforcement member in accordance with an alternative embodiment of the present invention;

FIGS. 24A–24E illustrate various tools of the present invention for implanting a reinforcement member in accordance with the method illustrated in FIGS. 25A–25J;

FIGS. 25A–25J illustrate an alternative method for implanting a reinforcement member in accordance with an embodiment of the present invention;

FIGS. 26A–26G illustrate various tools of the present invention for implanting a reinforcement member in accordance with the method illustrated in FIGS. 27A–27H;

FIGS. 27A–27H illustrate an alternative method for implanting a reinforcement member in accordance with an embodiment of the present invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1B:
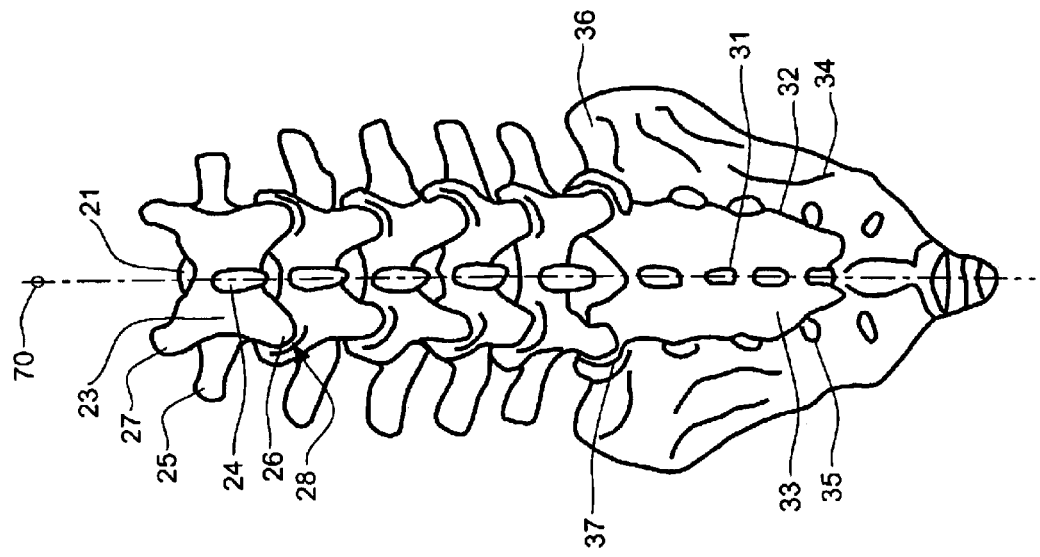
FIGS. 1A and 1B illustrate left lateral and posterior views, respectively, of a portion of the adult human vertebral (spinal) column.
Figure 1A:
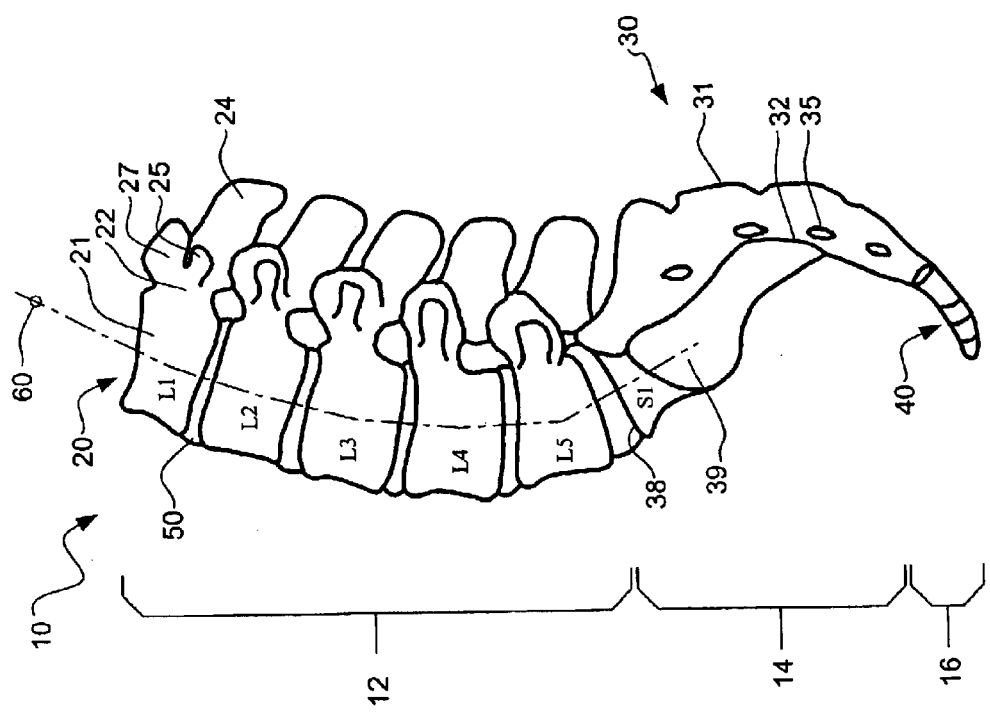

With reference to FIGS. 1A and 1B, the lower portion of an adult human vertebral column 10 is illustrated in left lateral and posterior views, respectively. The upper portion of the vertebral column 10 includes the thoracic region and the cervical region, which are not shown for purposes of simplified illustration only. The lower portion of the vertebral column 10 includes the lumbar region 12, the sacrum 14 and the coccyx 16. The sacrum 14 and the coccyx 16 are sometimes collectively referred to as the pelvic curvature.

The vertebral column 10 includes an axis of curvature 60 which generally forms a double-S shape when viewed laterally. The vertebral column 10 also includes a median plane 70 which is a sagittal plane bisecting the vertebral column 10 into symmetrical left lateral and right lateral portions. In posterior views, the median plane 70 appears as a line.

The lumbar region 12 of the vertebral column 10 includes five (5) vertebrae 20 (labeled L1, L2, L3, L4 and L5) separated by intervertebral discs 50. The sacrum 14, which includes five (5) fused vertebrae 30 (superior vertebra 30 labeled S1), is separated by a single disc 50 from the coccyx 16, which includes four (4) fused vertebrae 40. Although not labeled, the intervertebral discs 50 may be referenced by their respective adjacent vertebrae. For example, the disc 50 between the L4 and L5 lumbar vertebrae 20 may be referred to as the L4L5 disc. Similarly, the disc 50 between the L5 lumbar vertebra 20 and the S1 sacral vertebra 30 may be referred to as the L5S1 disc.

Although each vertebra 20/30/40 is a unique and irregular bone structure, the vertebrae 20 of the lumbar region 12 (in addition to the thoracic and cervical regions) have common structures. Each vertebra 20 of the lumbar region 12 generally includes a body portion 21 and a vertebral arch portion 22/23 which encloses the vertebral foramen (not visible) in which the spinal cord is disposed. The vertebral arch 22/23 includes two pedicles 22 and two laminae 23. A spinous process 24 extends posteriorly from the juncture of the two laminae 23, and two transverse processes 25 extend laterally from each lamina 23. Four articular processes 26/27 extend inferiorly 26 and superiorly 27 from the laminae 23. The inferior articular process 26 rests in the superior articular process 27 of the adjacent vertebra to form a facet joint 28.

The five (5) vertebrae 30 of the sacrum 14 are fused together to form a single rigid structure. The sacrum 14 includes a median sacral crest 31 which roughly corresponds to the spinous processes of the vertebrae 30, and two intermediate sacral crests 32 which roughly correspond to the articular processes of the vertebrae 30. The sacral laminae 33 are disposed between the median 31 and intermediate 32 sacral crests. Two lateral sacral crests 34 are disposed on either side of the sacral foraminae 35. The sacrum 14 also includes a pair of sacral wings 36 which define auricular surfaces 39. The superior (S1) sacral vertebra 30 includes two superior articular processes 37 which engage the inferior articular processes 26 of the L5 lumbar vertebra 20 to form a facet joint, and the base 38 of the superior sacral vertebra S1 is joined to the L5S1 disc 50.

Figure 2B:
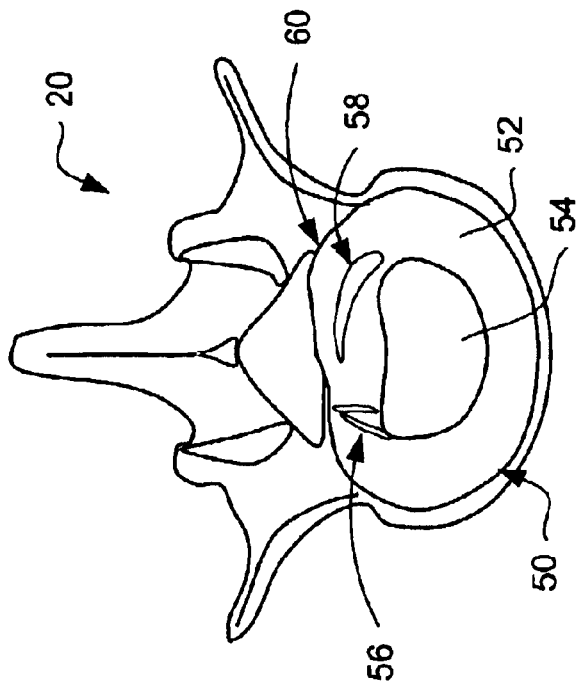
FIGS. 2A and 2B illustrate superior (top) views of a healthy disc and a degenerated disc, respectively, and an adjacent vertebral body.
Figure 2A:
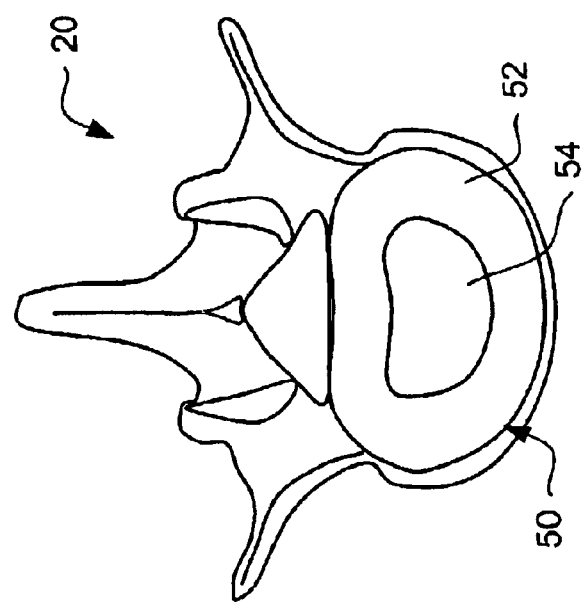

With reference to FIG. 2A, each intervertebral disc 50 includes an annulus fibrosus 52 surrounding a nucleus pulposus 54. The posterior annulus 52 is generally thinner than the anterior annulus 52, which may account for the higher incidence of posterior disc protrusions. The annulus fibrosus 52 comprises about 60% of the total disc 50 cross-sectional area, and the nucleus pulposus 54 only comprises about 40% of the total disc 50 cross-sectional area. The annulus fibrosus 52 comprises 40–60% organized collagen in the form of a laminated structure. The nucleus pulposus 54 comprises 18–30% collagen in the form of a relatively homogenous gel.

A common theory is that each intervertebral disc 50 forms one support point and the facet joints 28 form two support points of what may be characterized as a three point support structure between adjacent vertebrae 20. However, in the lumbar region 12, the facet joints 28 are substantially vertical, leaving the disc 50 to carry the vast majority of the load. As between the annulus fibrosus 52 and the nucleus pulposus 54 of the disc 50, it is commonly believed that the nucleus 54 bears the majority of the load. This belief is based on the theory that the disc 50 behaves much like a balloon or tire, wherein the annulus 22 merely serves to contain the pressurized nucleus 54, and the nucleus 54 bears all the load. However, this theory is questionable since the annulus fibrosus 52 comprises 60% of the total disc 50 cross-sectional area and is made of 40–60% organized collagen in the form of a laminated structure. By contrast, the nucleus pulposus 54 only comprises 40% of the total disc 50 cross-section and is made of 18–30% collagen in the form of a relatively homogenous gel. Thus, a more plausible theory is that the annulus fibrosus 52 is the primary load bearing portion of the disc 50.

With reference to FIG. 2B, the intervertebral discs 50 become progressively dehydrated and malnourished with age. When combined with continued stressing, the disc begins to degenerate. With continued degeneration, or an excessive stressing event, the annulus fibrosus of the disc may tear, forming one or more radial fissures 56 or circumferential fissures 58, which may progress to larger tears. Larger tears may allow the gelatinous material of the nucleus pulposus 54 to flow out of the nucleus and into the outer aspects of the annulus 52. The flow of the nucleus pulposus 54 to the outer aspects of the annulus 52 may cause a localized bulge 60. A posterior bulge 60 may result in direct impingement of a nerve root (not shown). Nuclear material that escapes through an advanced tear may cause further mechanical irritation and additionally cause chemical irritation of a nerve root. A nerve root may also be compressed or tethered by a narrowing of the intervertebral foraminae, resulting from a loss in disc height caused by sustained degeneration of the disc 50. Small nerve endings (not shown) in or near the perimeter of the annulus 52 may also be mechanically or chemically irritated at the sites of the fissures 56/58. In all cases, degeneration of the disc eventually leads to disc related pain of some origin.

FIGS. 3A–3F schematically illustrate reinforcement members 100/200/300/600 implanted in a degenerated disc 50. In all instances, the reinforcement members 100/200/300/600 mechanically stabilize and strengthen the disc 50 to minimize if not eliminate chronic irritation of nerve roots and nerves around the periphery of the disc annulus 52. As can be seen in FIGS. 3A–3F, the reinforcement members 100/200/300/600 also radially and/or circumferentially compress the disc 50 to close fissures 56/58, thereby preventing the ingress of nerves and potentially facilitating healing. The reinforcement members 100/200/300/600 may further be used to stabilize the posterior portion of the disc 50 after a discectomy procedure in order to reduce the need for re-operation.

Figure 3A:
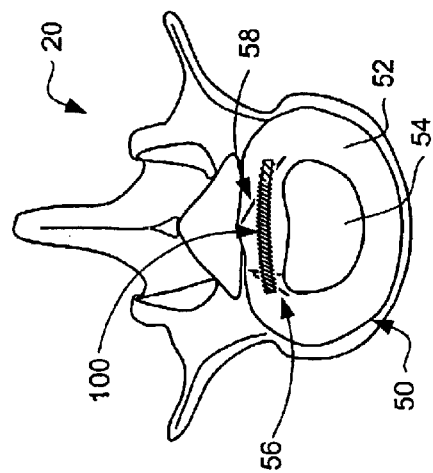
FIGS. 3A–3F schematically illustrate superior (top) views of reinforcement members disposed in degenerated discs.
Figure 3B:
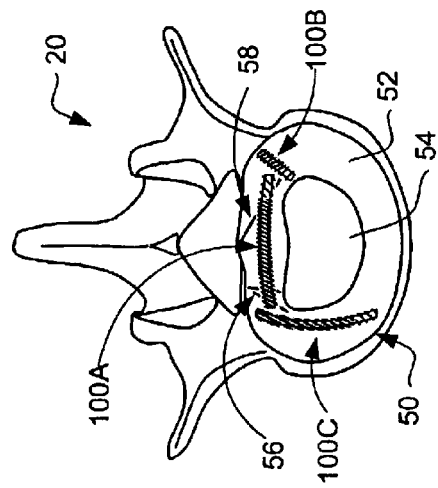
Figure 3C:
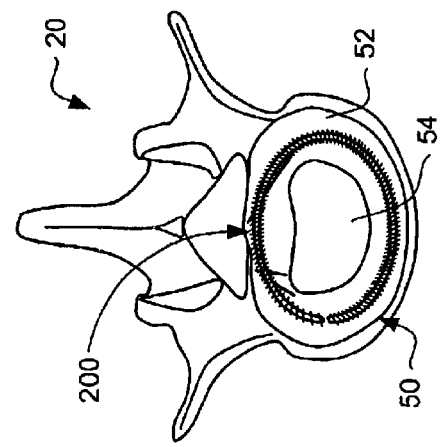
Figure 3D:
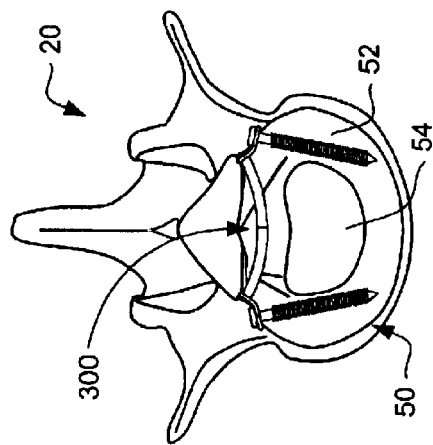

FIGS. 3A–3F show examples of where the reinforcement members 100/200/300/600 may be implanted in the annulus 52. However, the reinforcement members 100/200/300/600 may be implanted in any portion of the annulus 52 including, without limitation, the posterior, anterior or lateral portions thereof. Because most disc related pain is associated with damage to the posterior portion of the disc 50, the reinforcement members 100/200/300/600 preferably provide support to the posterior portion of the annulus 52 and establish anchor points in the lateral and anterior portions of the annulus 52, or completely encircle the annulus 52. The reinforcement members 100/200/300/600 may be used individually as shown in FIGS. 3A and 3C–3F, or in combination as shown in FIG. 3B. Although not shown, any combination of the different types of reinforcement members 100/200/300/600 may be utilized.

The reinforcement members 100/200/300/600 may be oriented generally parallel to the periphery of the annulus 52

(e.g., reinforcement members 100A, 100C, 200, 300, 600), generally radial to the annulus 52 (e.g., reinforcement member 100B), or any other orientation suitable for stabilizing and/or compressing the desired portion(s) of the annulus 52. Generally, the closer the reinforcement members 100/200/300/600 are to the periphery of the annulus 52, the greater the amount of support and stabilization provided to the disc 50. As such, the reinforcement members 100/200/300/600 preferably have a curvature conforming to the periphery of the annulus 52 such that they may be implanted as close to the periphery of the annulus 52 as possible. The reinforcement members 100/200/300/600 may have such a curvature in the relaxed (zero stress) state, or the curvature may be imparted by the insertion path or defined by the insertion tools used.

The reinforcement members 100/200/300/600 may extend across and close fissures 56/58 as shown, or any other portion of the annulus 52 to provide compression and stabilization of the disc 50. Although not shown, the reinforcement members 100/200/300/600 may extend across or into the nucleus 54. In such a case, it is preferred that the reinforcement members 100/200/300/600 do not extend outside the periphery of the annulus 52 in order to reduce the probability of nuclear material escaping from the outer aspects of the annulus 52.

The reinforcement members 100/200/300/600 are sized to fit within the annulus 52 of a human disc 50. Thus, the collective diameter and length of the reinforcement members 100/200/300/600 implanted preferably does not exceed the height and circumference/diameter, respectively, of the annulus 52, depending on the number and orientation of the reinforcement members 100/200/300/600 implanted. The reinforcement members 100/200/300/600 may be made of a biocompatible material or coated with a biocompatible material. Suitable structural materials for the reinforcement members 100/200/300/600 include stainless steel and super elastic alloys such as nickel titanium. All or a portion of the reinforcement members 100/200/300/600 may be made of biodegradable or bioabsorbable material such as resorbable collagen, LPLA (poly(1-lactide)), DLPLA (poly(dl-lactide)), LPLA-DLPLA, PGA (polyglycolide), PGA-LPLA or PGA-DLPLA. Other metals, alloys, polymers, and composites having suitable tensile, compression and fatigue strength and elasticity may also be used. The reinforcement members 100/200/300/600 may further include growth factors to facilitate healing, agents which render nuclear matter inert or otherwise reduce chemical irritation thereof, and/or anesthetic agents to reduce nerve signal transmission (i.e., pain).

Figure 3F:
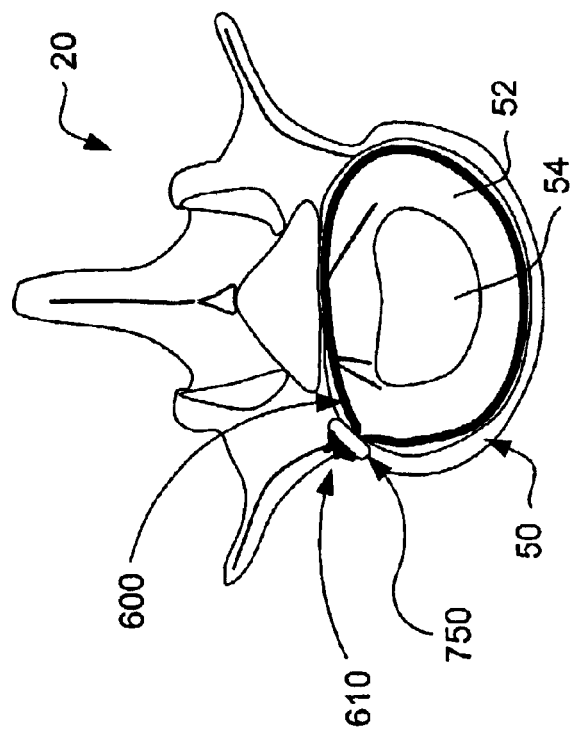
Figure 3E:
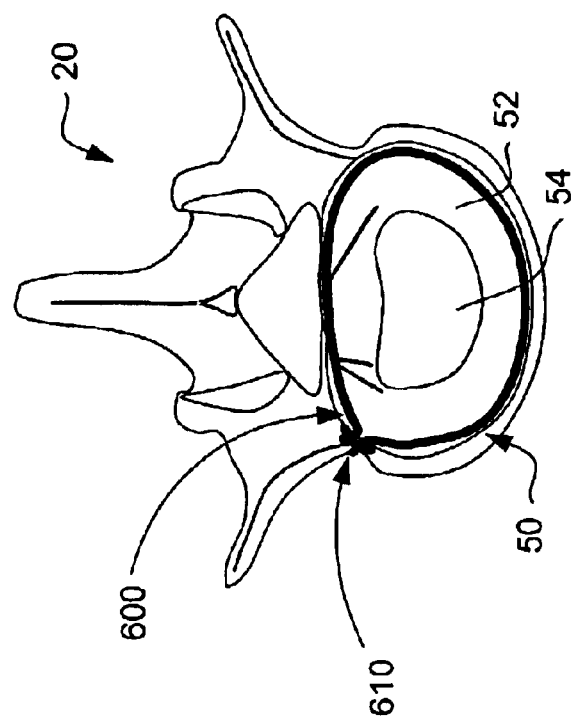

Reinforcement member 600, as illustrated in FIGS. 3E and 3F, is adapted to completely encircle the annulus 52 to thereby apply uniform compressive forces about the periphery of the annulus 52. The reinforcement member 600 has opposing ends which are secured together by a permanent connection 610 such as a knot as seen in FIG. 3E. Optionally, a pledget 750 may be employed as illustrated in FIG. 3F and as discussed in more detail hereinafter. Reinforcement member 600 may substantially reside within the confines of the annulus 52, with the connection 610 and optional pledget 750 residing within or immediately outside the confines of the annulus 52. While reinforcement member 600 is shown within the outer aspect of the annulus 52, it is also contemplated that all or portions of reinforcement member 600 may be implanted outside the annulus 52. For example, reinforcement member 600 may be placed in the tissue plane between the outside of the annulus 52 and external connective tissues (not shown).

The reinforcement member 600 may comprise a monofilament or multifilament structure that resists elongation in tension, but is otherwise very flexible. For example, the reinforcement member 600 may comprise a polymeric or metallic fiber, cable, thread, suture, wire, ribbon, or the like. Suitable materials for the circumferential reinforcement member 600 include, but are not limited to, commercially available suture materials used in a variety of surgical procedures. Such exemplary suture materials include biodegradable suture made from polylactic acid and polyglycolic acid, and non-degradable materials such as monofilament and braided polypropylene and polyester (PET). Another suitable non-degradable suture material is made from expanded polytetrafluoroethylene (ePTFE). Other materials which are suitable for the circumferential reinforcement member 600 include braided ultra-high molecular weight fibers of polyethylene (UHMWPE), commercially available as Spectra™ or Dyneema™, as well as other high tensile strength materials such as Vectran™, Kevlar™, and natural or artificially produced silk.

As an alternative, the reinforcement member 100/200/300/600 may be designed for temporary heating (post-implantation) to cause thermal changes to the annulus. Because the annulus is comprised of overlapping bands of oriented collagen which tend to shrink in the direction of orientation when heated to temperatures of 50 to 90 degrees centigrade, temporarily heating the reinforcement member 100/200/300/600 causes thermal reformation of the annulus. In addition, annular defects such as fissures and tears can refuse, particularly if the edges are brought into apposition prior to or during the heating step. Such annular defects may be closed (i.e., edges brought into apposition) by compression imparted by the reinforcement member 100/200/300/600 during implantation or by collagen shrinkage imparted by heating the reinforcement member 100/200/300/600.

The reinforcement member 100/200/300/600 may be heated by inducing heat in the material of the reinforcement member 100/200/300/600 or by incorporating one or more heating elements into the reinforcement member 100/200/300/600. In both cases, a source of electric or magnetic power (e.g., electric power supply, magnetic field generator, RF transmitter, etc.) is used to provide energy to the reinforcement member 100/200/300/600 which converts the electric/magnetic energy to thermal energy. Such a power source may be directly or remotely connected to the reinforcement member 100/200/300/600.

For example, the reinforcement members 100/200/300/600 may include resistive heating elements directly connected to an internal (implanted) power supply or directly connected (transdermal) to an external electric power supply. Alternatively, the resistive heating elements may be connected to an implanted receiving antenna which receives a power signal from a remote external power signal transmitting antenna. As a further alternative, the reinforcement member 100/200/300/600 may be heated by remote inductive heating via an external alternating magnetic field generator. Because significant portions of the reinforcement member 100/200/300/600 may comprise a conductive metallic material, the presence of an alternating magnetic field will inductively heat the reinforcement member 100/200/300/600. Further aspects of these and other heated reinforcement member 100/200/300/600 embodiments are discussed in more detail with reference to FIGS. 4H–4M.

In all embodiments, various visualization techniques may be used to facilitate implantation of the reinforcement members 100/200/300/600. For example, real time CT scanning, real time MR imaging, or a combination of preoperative CT or MR images superimposed onto a real time device tracking images such as the system commercially available under the trade name STEALTH™ available from Sofamor Danek.

FIGS. 4A–4K illustrate various embodiments of the reinforcement member 100 in accordance with the present invention. The embodiments of FIGS. 4A–4K illustrate various features which may be combined in any way to provide the desired reinforcement member 100. Reinforcement member 100 may be sized and oriented as shown and discussed with reference to FIGS. 3A and 3B. Reinforcement member 100 includes a body portion 110 and an anchor 120. The anchor 120 serves to immobilize or limit movement of the reinforcement member 100 relative to the annulus 52.

In FIGS. 4A, 4D and 4F, the anchor is in the form of threads 122 disposed about the periphery of the body portion 110, which behave like threads on a screw and engage the annulus 52 upon rotation therein. When threads 122 are used, the proximal end of the body 110 may include slots 116 as shown in FIG. 4C, which is an end view taken along line 4C—4C in FIG. 4A. The slots 116, or any other suitable mating geometry, facilitate rotation with a driver having a mating distal end. In FIG. 4E, the anchor 120 is in the form of sloped rings 124 spaced along the length of the body portion 110, which behave like rings on a ring-shank nail to engage the annulus 52 upon pushing therein. Those skilled in the art will recognize that other anchor 120 mechanisms such as barbs, expandable anchors, etc. may also be used.

The anchor 120 may extend the full length of the body portion 110 as shown in FIGS. 4A and 4F, or may be disposed only on proximal and distal portions of the body as shown in FIGS. 4D and 4E. The body portion 110 may be tubular defining a lumen 112 extending therethrough as shown in FIG. 4B, which is a cross-sectional view taken along line 4B—4B in FIG. 4A. The lumen 112 facilitates advancement of the reinforcement member 100 over a stylet to facilitate insertion into the annulus 52, as will be discussed in greater detail hereinafter. Alternatively, the body portion 110 may have a solid cross-section as shown in FIG. 4G, which is a cross-sectional view taken along line 4G—4G in FIG. 4F. In this alternative embodiment, the solid cross-section body portion 110 may include a sharpened distal tip 114 as shown in FIG. 4F to facilitate insertion into the annulus 52.

Preferably, the threads 122 have a variable pitch such that the annulus is compressed as the reinforcement member 100 is rotated and advanced into the annulus 52. Variable pitch threads 122, as shown in FIGS. 4A, 4D and 4F, generally have a larger pitch at the distal end of the body 110 and a smaller pitch at the proximal end of the body 110. The larger pitch distal threads 122 pull the annular tissue 52 a greater distance per revolution than the smaller pitch proximal threads 122. Thus, as the reinforcement member 100 is rotated and advanced into the annulus 52, the distal threads pull the annular tissue together and the proximal threads hold the tissue in place thereby compressing the annulus 52. By compressing the annulus 52, the disc 50 is mechanically stabilized and the fissures 56/58 are closed to facilitated healing.

Although compression of the annulus 52 is preferred, it is not necessary to have compression in order to provide some degree of mechanical stabilization. To the extent that compression is desired, the variable pitch threads 122 mentioned above are currently preferred. However, other compression techniques are equally useful. For example, standard constant pitch threads 122 and tapered rings 124 may achieve compression by utilizing a step-wise advancement and tension technique as will be described in more detail hereinafter.

In order to provide the ability to temporarily heat the reinforcement member 100 as discussed previously, various modifications to the design of the reinforcement member 100 may be made as described with reference to FIGS. 4H–4M. These design modifications may also be applied to reinforcement members 200 and 300, but are described with specific reference to reinforcement member 100 for purposes of illustration only. Although numerous methods may be employed to temporarily heat the reinforcement member 100, two preferred methods, resistive heating and inductive heating are described in detail.

FIG. 4H illustrates a generic reinforcement member 100 including body portion 110, anchors 120 (not shown for sake of clarity) and heating element 140 in the form of a resistive wire. FIG. 4I is a cross-sectional view taken along line 4I—4I in FIG. 4H. Resistive wire 140 may be helically wound on the outer surface of the body 110, the inner surface of the body 110, or in the wall of the body 110. Preferably resistance wire 140 is helically incorporated into the wall of the body portion 110 at the time of fabrication, for example by insert/injection molding. Resistance wire 140 may helically traverse the length of the body 110 in one pitch direction, then traverses back in the opposite direction in an opposite pitch direction. In this manner, a single wire traverses the length of the body 110, but has two ends at the proximal end of the body 110 available for connection to an electrical power source or receiving antenna.

Resistance wire 140 is conductive, but offers a high enough resistance to heat during the application of electrical current. The wire may be made of a variety of conductive metals, including copper, tungsten, platinum, or gold, and may be covered/coated with a biocompatible material. Preferably, the resistance wire 140 is formed of a biocompatible metal, but this is not essential as long as direct tissue exposure is avoided such as when a biocompatible covering/coating is used or when the wire 140 is embedded in the wall of body 110. Since the wire will be heated to a relatively high temperature (e.g., 50 to 90 degrees centigrade), the body 110 or covering is preferably made of a material which can withstand elevated temperatures, preferably of a high temperature polymer such as Polyimide, PTFE, Kynar, or PEEK.

Electrification of resistance wire 140 may be accomplished by initially incorporating a pair of releasable low resistance lead wires 142 to the ends of the resistance wire 140, as shown in FIG. 4H. The lead wires 142 are passed through or reside alongside driver 440 during the advancement of reinforcement member 100 as described with reference FIGS. 8A–8L. If they are passed through the driver 440, the driver must be hollow. Once the reinforcement member 100 is fully implanted, the lead wires 142 are connected to a power source 146, which delivers electrical current to the reinforcement member 100, causing it and the surrounding tissue to heat to a desired temperature for a desired period of time. The temperature of the resistance wire 140 may be monitored by measuring the current demand from the power source 146 or by positioning a thermocouple (not shown) adjacent the proximal end of the reinforcement member 100. Once the heating step is finished, the releasable leads 142 are removed from the resistance wires 140 utilizing releasable connection 141. Removal of the releasable leads 142 may be accommodated by providing a low tensile strength connection which separates by pulling, or by providing a fusible metal strip connection which separates by applying electric current above a threshold value. Such a fusible metal strip connection may also serve to self-limit the degree to which the reinforcement member is heated.

Figure 4J:
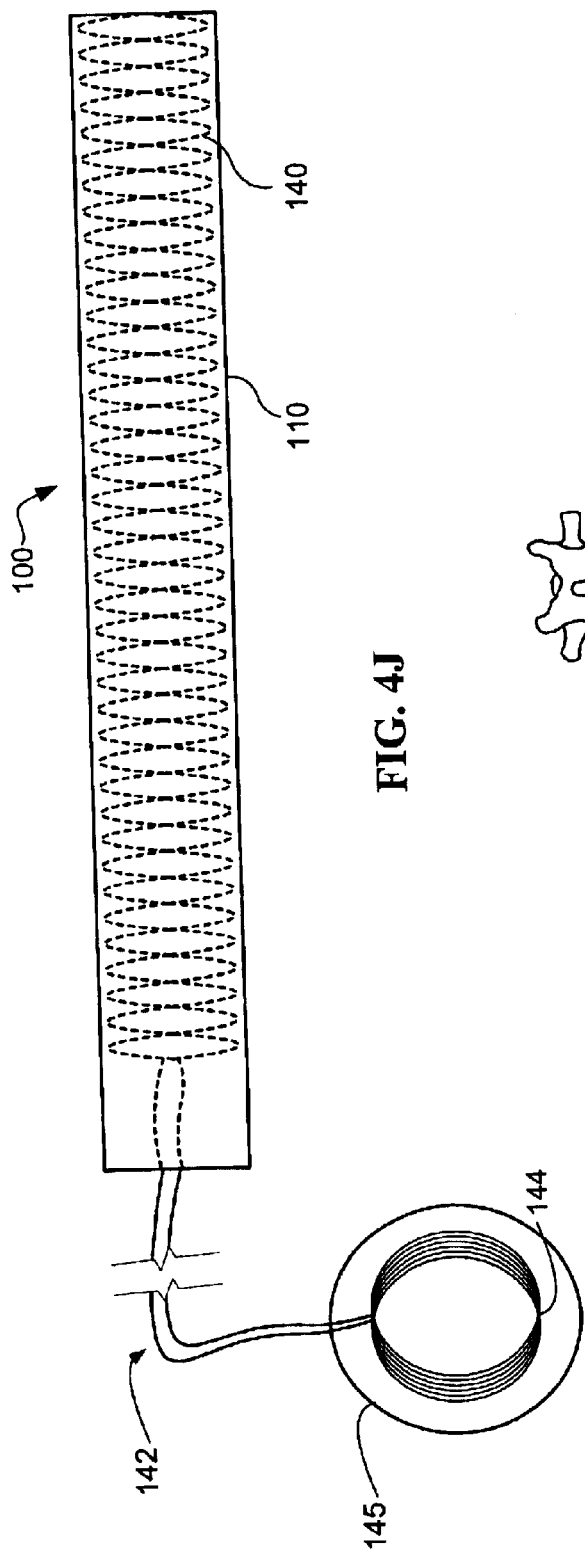

Alternatively, the leads 142 are not removable, but stay attached to the resistive wires 140 and reinforcement member 100, as illustrated in FIG. 4J. In this embodiment, and preferably after the reinforcement member 100 is implanted, the leads 142 are attached to an implantable receiver antenna such as conductive wire coil 144. The receiver coil 144 may be incorporated into a housing 145 having a flat disc shape which is subcutaneously positioned adjacent the access site. Since the lead wires 142 and the receiver coil 144 are implanted within the body, the housing 145 and the lead wires 142 are preferably encased in a biocompatible and stable material, for example silicone rubber.

Figure 4K:
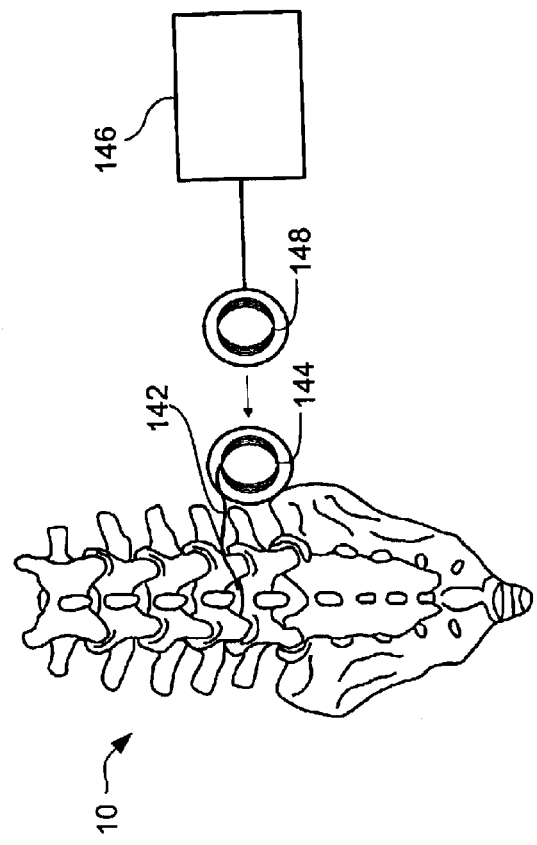

FIG. 4K illustrates an example of a suitable implant position for the receiver coil 144, relative to the vertebral column 10, preferably adjacent the lumbar disc being treated. The receiver coil 144 and housing 145 are oriented parallel to the surface of the skin, and the access site is then closed. Once positioned, a similarly shaped transmitting coil 148 is placed on the skin surface, adjacent and overlapping the subcutaneous receiver coil 144. The transmitting coil 148 is connected to a power source 146 and associated transmission circuit. When an alternating current is delivered to the transmitting coil 148, a corresponding alternating current is generated in the receiving coil 144, which in turn causes the resistance wire 140 and the reinforcement member 100 to heat.

One advantage of this resistive heating method is that the heating procedure can be repeated multiple times, without the need for reoperation or any other invasive procedure. For example, the patient may have the implanted reinforcement member(s) 100 heated upon initial implantation, and have them re-heated at any such time as back pain may recur. One of the mechanisms by which heat is believed to minimize back pain is by the destruction of nerve endings at the periphery of the annulus. However, new nerve endings may permeate the annulus, necessitating a subsequent heating to return the patient to a pain-free state.

As an alternative to the antennas 144/148, a transdermal plug 149 may be used to establish direct connection between the leads 142 and the power source 146. The plug 129 includes an internal implantable portion and an external portion. To facilitate immediate heating of the reinforcement member 100, the internal and external portions of the plug 129 may be connected just after implantation of the reinforcement member 100, but prior to closing the access site. The internal portion of the plug 129 is then positioned just below the skin and the access site is closed. To facilitate post-operative heating, a small incision may be made in the skin to connect the internal and external portions of the plug 129.

An alternate method of heating reinforcement member 100 and surrounding annular tissue is the use of inductive heating. Inductive heating is used in many industrial and some medical applications. Essentially, a high frequency alternating magnetic field is oriented on the object to be heated. The alternating magnetic field causes eddy currents in the object to be heated. These eddy currents then cause ohmic heating. As long as the object to be heated is conductive, usually metallic, it may be inductively heated.

To facilitate inductive heating, all or a significant portion of reinforcement member 100 is fabricated of a conductive metal, such as stainless steel, carbon steel, MP35N, nickel titanium alloy, or tungsten. The choice of material will influence the parameters needed for the inducting power source. Preferably, the entire body 110 is fabricated of the conductive metal.

Figure 4M:
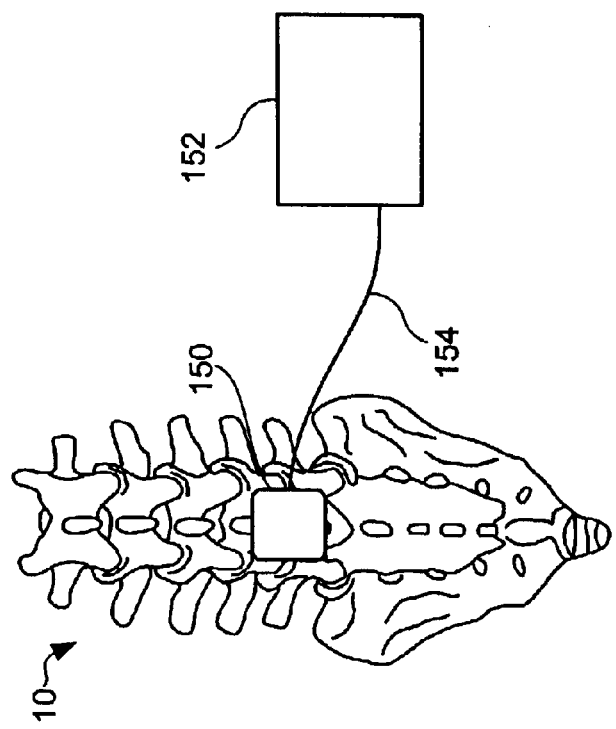
Figure 4L:
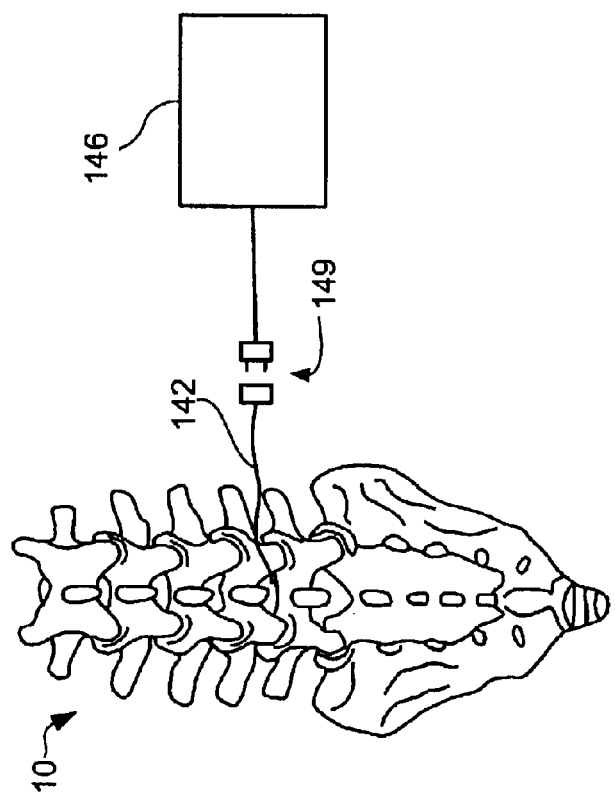

With reference to FIG. 4M, the inductor may include a power source 152 coupled by leads 154 to a coil 150 which generates a large alternating magnetic field. The coil 150 may have a long tubular shape, inside which the patient resides during heating, or may be of a smaller size (as illustrated) which is oriented toward the reinforcement member 100. The main parameters which need to be adjusted to result in a desired heating of the reinforcement member 100 are the frequency and amplitude of the alternating magnetic field. Typical frequencies will range from about 10 kHz to 10 MHz. Inductive heating also has the advantage of allowing for multiple subsequent heating treatments for the patient, should back pain recur.

While the reinforcement member 100 is preferably a permanently implanted device, the incorporation of temporary heating immediately or shortly after implantation allows for the possibility of temporary implantation. In this usage of reinforcement member 100, it is implanted using the methods and tools described in further detail below. But, once fully implanted, a transient heating step is performed. Because the reinforcement member causes the annular tissue to compress circumferentially and/or radially, the heating is particularly effective at remodeling the annular tissue to a more normal, pre-degenerated condition. Therefore, it may not be necessary to keep the reinforcement member implanted. The reinforcement member 100 can be removed by essentially reversing the implantation steps. In order to facilitate removal following heating, it is desirable to provide a lubricious coating such as a hydropholic polymer or PTFE coating on the surface of the reinforcement member 100, including the body 110 and anchor 120.

FIGS. 5A–5C schematically illustrate a circumferential reinforcement member 200, which is generally the same as reinforcement member 100 except as described herein. FIG. 5B is a cross-sectional view taken along line 5B—5B in FIG. 5A, and FIG. 5C is an end view taken along line 5C—5C in FIG. 5A. The circumferential reinforcement member 200 includes a tubular body 210 defining a lumen 212 to facilitate advancement over a stylet. The circumferential reinforcement member 200 also includes an anchor 220, preferably in the form of variable pitch threads 222. The proximal end of the body 210 the may include slots 216 or other suitable mating geometry to facilitate rotation by a driver having a mating distal end. Any of the variants of reinforcement member 100 discussed with reference to FIGS. 4A–4G may be applied to circumferential reinforcement member 200.

The circumferential reinforcement member 200 may have a geometry (e.g., circle, ellipse, oval, etc.) corresponding to the geometry of the outer aspects of a healthy annulus 52, or the member 200 may be naturally straight, taking on a curved shape during implantation. Because the circumferential reinforcement member 200 is implanted in the annulus 52 around the entire periphery thereof, the reinforcement member maximizes anchoring strength and provides superior stabilization around the entire disc 50. Thus, it is preferable that the reinforcement member 200 define a closed geometry once implanted, or even have overlapping ends, but an open geometry (e.g., semi-ellipse or semi-circle) may also be employed. The size and shape of the reinforcement member 200 may be pre-selected to accommodate anatomical variations of the annulus 52 between patients. The reinforcement member may have a relaxed size that is smaller than the implanted size such that additional radial and circumferential compression is achieved.

Circumferential reinforcement member 200 may further incorporate design features which allow for temporary heating. As described in connection with reinforcement 100 above, similar features which allow for resistive heating or inductive heating may be incorporated.

FIGS. 6A–6H schematically illustrate reinforcement member 300, including a pair of tubular pins 310, two screws 320 and two connecting rings 330 which may be assembled as shown in FIG. 6F. With reference to FIG. 6A, each of the tubular pins 310 includes a shaft portion 312, a head portion 314 and a connection mechanism 318. The shaft 312 is sized to fit within a hole of the connection ring 330 and the head 314 is sized larger than the same hole. The connection mechanism 318 may comprises a threaded shaft insertable into a threaded hole as shown, or any other known mechanical releasable connection that maintains the profile of the shaft portion 312. As seen in FIG. 6B, which is a cross-sectional view taken along line 6B—6B in FIG. 6A, the shaft portion 312 includes a lumen 313 to facilitate advancement over a stylet. The heads 314 may each include a slot 316 as seen in FIG. 6C, which is an end view taken along line 6C—6C in FIG. 6A, or other suitable geometry to mate with a distal end of a driver to facilitate rotation of the pins 310 to screw the releasable connection together.

The screws 320 include a shaft 322, a head 324, threads 328 and a sharpened tip 323 as seen in FIG. 6D. The screws 320 may comprise a wide variety of orthopedic screw designs, particularly those suitable for implantation into cartilage and other collagen-based tissues. The shaft 322 and threads 326 are sized to fit within a hole of the connection ring 330 and the head 324 is sized larger than the same hole. The head 324 includes slots 326 as seen in FIG. 6E, which is an end view taken along line 6E—6E in FIG. 6D, or other suitable mating geometry to facilitate rotation by a driver having a mating distal end.

The connection rings 330 each have first and second rings 331/333 defining first and second holes 332/334 as shown in FIG. 6F. The first hole 332 is sized to provide a sliding fit about the shaft 312 of the pins 310 and the second hole is sized to provide a sliding fit about the shaft 322 and threads 326 of the screws 320. As seen in the side view shown in FIG. 6G, each of the connection rings 330 also define an angle 336 between the rings 331/333 to accommodate the implanted arrangement as shown in FIG. 6H.

As described above in connection with reinforcement members 100 and 200, reinforcement member 300 can also incorporated features to provide for temporary heating. For example, tubular pins 310 can incorporate resistive wire, or can be fabricated of a conductive metallic material, in a manner similar to that described for reinforcement members 100 or 200 above.

Figure 7A:
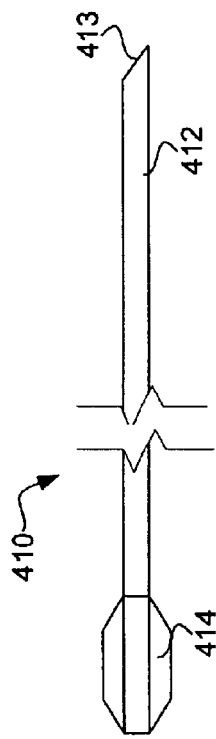
FIGS. 7A–7F illustrate tools of the present invention for implanting the reinforcement members shown in FIGS. 3A and 3B in accordance with the method illustrated in FIGS. 8A–8L.
Figure 7B:
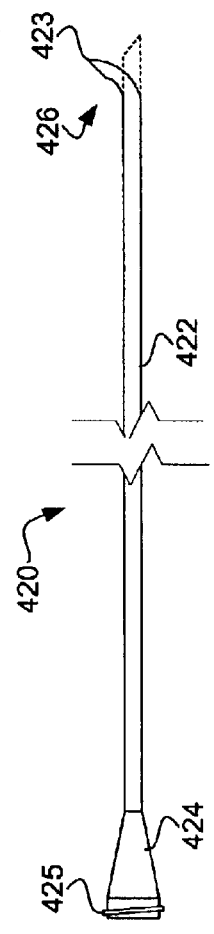
Figure 7C:
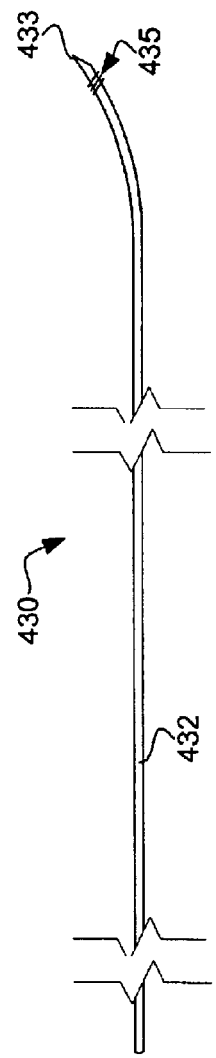
Figure 7D:
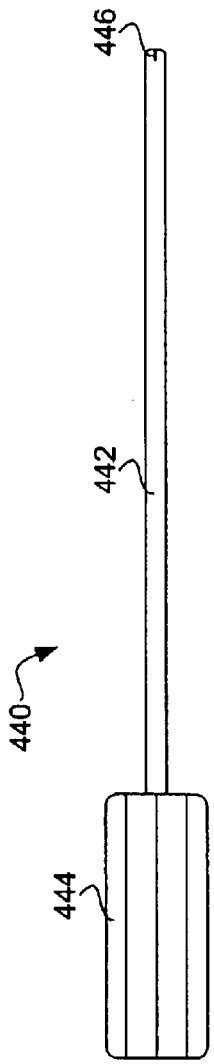
Figure 7E:
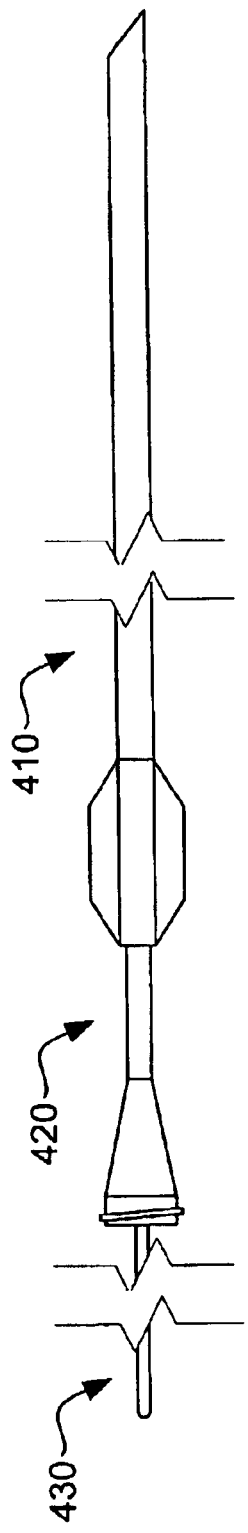
Figure 7F:
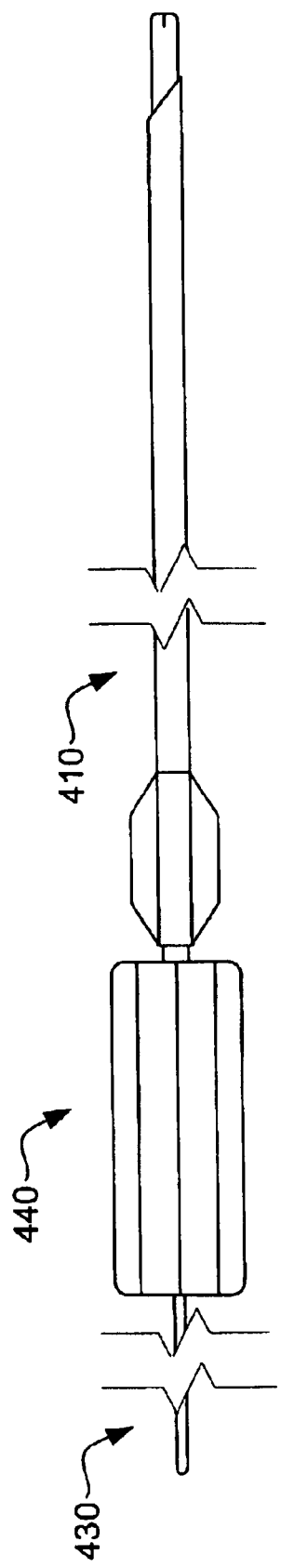

Referring now to FIGS. 7A–7F, various tools 410, 420, 430 and 440 are shown individually and assembled. The tools 410, 420, 430 and 440 may be used to implant the reinforcement members 100 discussed above. The tools include a rigid, sharpened, hollow trocar 410 as shown in FIG. 7A, a semi-rigid, sharpened, hollow curved needle 420 as shown in FIG. 7B, a sharpened curved stylet 430 as shown in FIG. 7C, and a hollow driver 440 as shown in FIG. 7D. As seen in FIG. 7E, the sharpened stylet 430 fits into the semi-rigid needle 420 which fits into the rigid trocar 410. As seen in FIG. 7F, the sharpened stylet 430 fits into the hollow driver 440 which fits into the rigid trocar 410.

With specific reference to FIG. 7A, the rigid hollow trocar 410 includes a hollow shaft 412 and a grip or handle 414. The shaft 412 includes a sharpened tip 413 to facilitate passage through the skin and back muscles, and insertion into the annulus 52. The shaft 412 is preferably made of a rigid metal such as a stainless steel hypodermic tube. The grip 414 may comprise a polymer and may be formed by insert injection molding with the shaft 412 inserted into the mold.

With specific reference to FIG. 7B, the semi-rigid curved needle 420 includes a hollow shaft 422 a hub 424. The shaft 422, which includes a sharpened tip 423, is longer than the rigid trocar 410 and has an outside diameter sufficiently small to fit into the rigid trocar 410. The shaft 422 is preferably made of a semi-rigid polymer or composite. The shaft 422 includes a curved distal portion 426 that may be straightened (shown in phantom) upon insertion of the semi-rigid needle 420 into the lumen of the rigid trocar 410. The hub 424 may include a fitting 425 to facilitate connection to a fluid source or a pressure source (e.g., a syringe).

With specific reference to FIG. 7C, the sharpened curved stylet 430 includes a flexible shaft 432 and a sharpened distal end 433. The distal tip 433 may optionally include an anchor 435 such as threads, tapered rings or barbs to facilitate the step-wise advancement and tension technique as will be described in detail hereinafter. If threads are used for the anchor 435, the curvature 434 of the distal portion of the shaft 432 may be eliminated to facilitate efficient torque transfer. The shaft 432 includes a curve 434 which approximates the curvature and diameter of the outer aspects of the annulus where the reinforcement member 100 is to be implanted. The shaft 432 is longer than the both the rigid trocar 410 and the semi-rigid needle 420, and may have a length on the order of 10 to 60 cm. The shaft 432 also has an outside diameter sufficiently small to fit into the semi-rigid needle 420. The shaft 422 preferably has a flexible but pushable construction incorporating a rigid metal such as stainless steel, or super-elastic nickel-titanium alloy. The sharpened stylet 430 is preferably highly elastic, to resist permanent set upon insertion into the curved portion 426 of the semi-rigid needle 420.

With specific reference to FIG. 7D, the hollow driver 440 includes a hollow shaft 442 and a grip or handle 444. The distal end of the hollow shaft 442 includes a tip 446 defining a geometry which mates with an end of the reinforcement member 100 to facilitate rotation thereof during implantation. The shaft 442 is preferably made of a torsionally rigid metal such as a stainless tool steel. The grip 444 may comprise a polymer and may be formed by insert injection molding with the shaft 442 inserted into the mold.

With general reference to FIGS. 8A–8L, the steps for implanting reinforcement member 100 are illustrated. It should be understood that the procedure for implanting a single member 100 in the posterior portion of the annulus 52 is shown for purposes of illustration, not limitation. All of the variables with regard to quantity, location, orientation, etc. discussed previously may be implemented by varying the generic procedure described hereinafter.

The method illustrated in FIGS. 8A–8L is a percutaneous procedure in which access to the disc 50 is achieved utilizing a number of small diameter tools which may be inserted through a patient's back (skin and back muscles), between adjacent vertebrae, and into the patient's disc 50. This percutaneous method minimizes the invasiveness of the procedure thereby reducing procedure time, procedure cost, postoperative pain and recovery time.

Figure 8B:
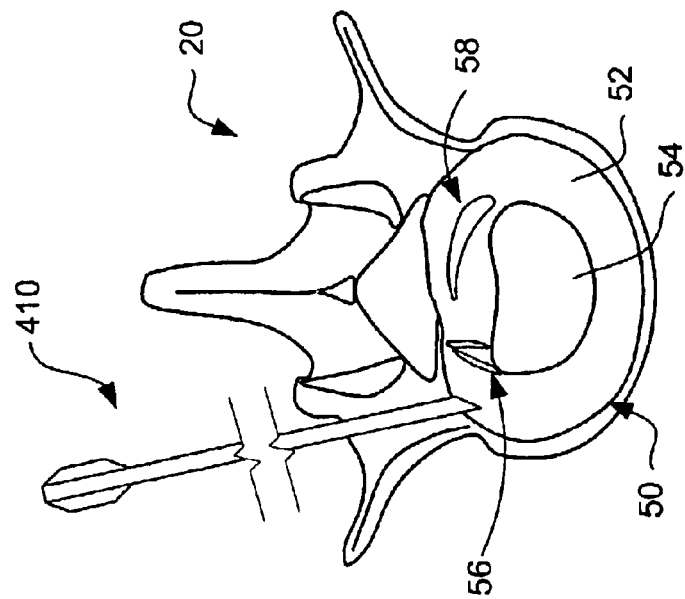
FIGS. 8A–8L illustrate a method for implanting the reinforcement members shown in FIGS. 3A and 3B in accordance with an embodiment of the present invention.
Figure 8A:
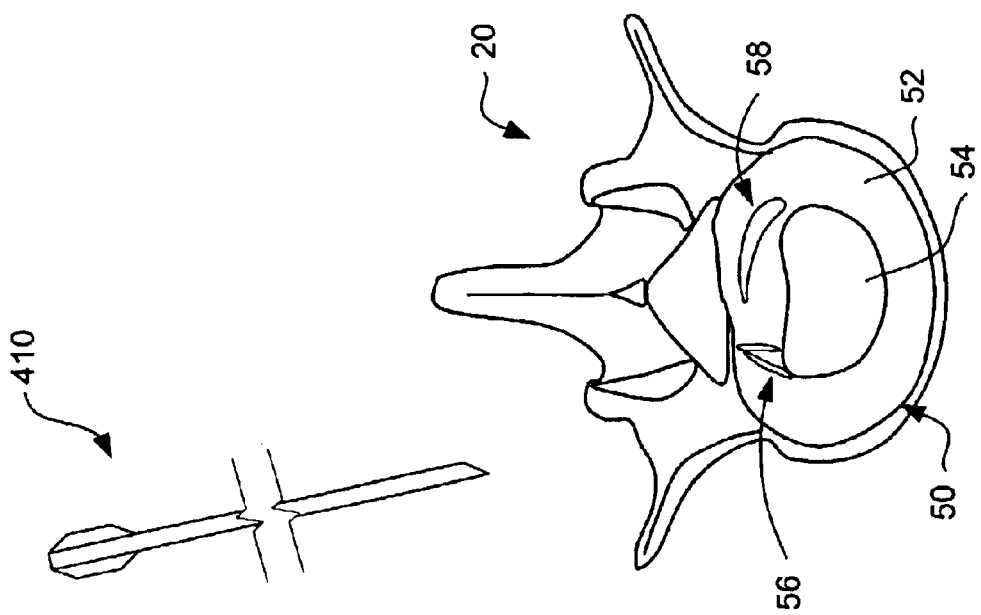

Initially, as shown in FIG. 8A, the rigid trocar 410 is positioned for insertion into the disc 50 as in a conventional discogram procedure. The rigid trocar 410 is advanced until the distal tip 413 of the trocar 410 is proximate the outer periphery of the posterior portion of the annulus 52 as seen in FIG. 8B.

Figure 8D:
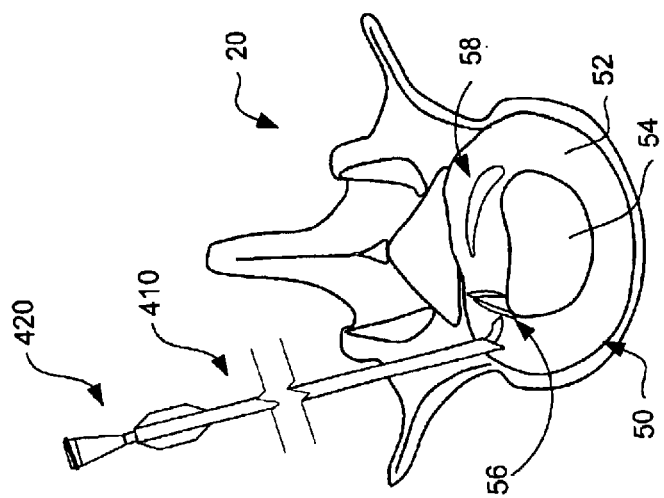
Figure 8C:
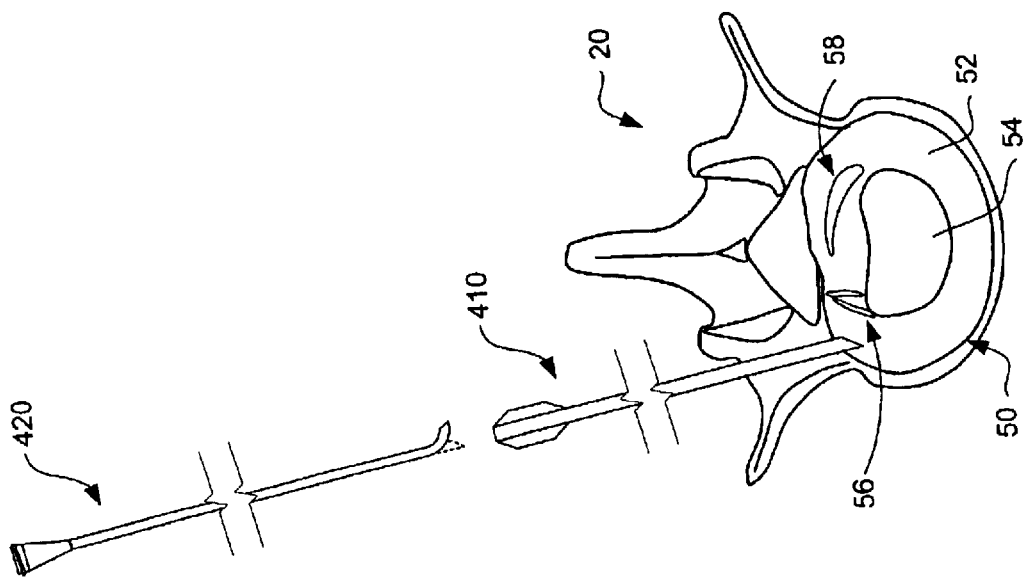

The curved portion 426 of the semi-rigid needle 420 is straightened for insertion into the trocar 410 as shown in FIG. 8C. The semi-rigid needle 420 (alone or with stylet 430) is advanced relative to the rigid trocar 410 until the curved portion 426 of the semi-rigid needle exits the distal tip 413 of the rigid trocar 410 and the desired amount of curvature is established, as seen in FIG. 8D. The curved portion 426 may be advanced until the tip 423 is roughly parallel to the posterior curvature of the annulus 52.

Figure 8F:
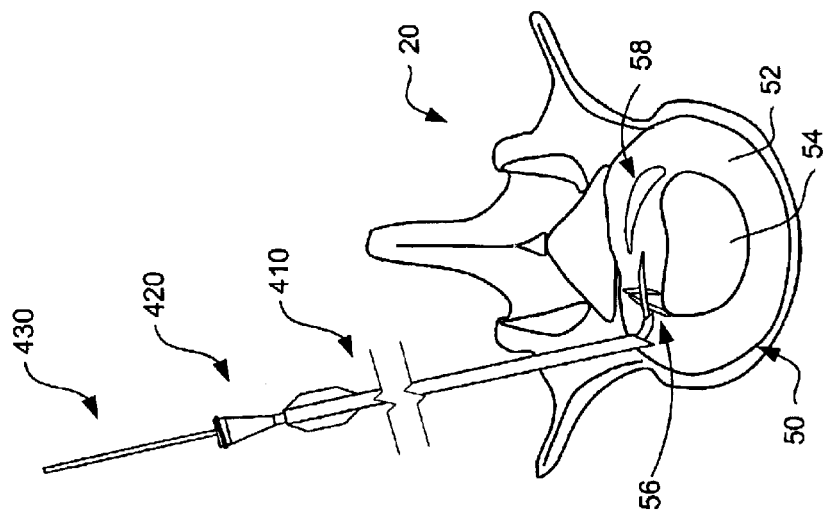
Figure 8E:
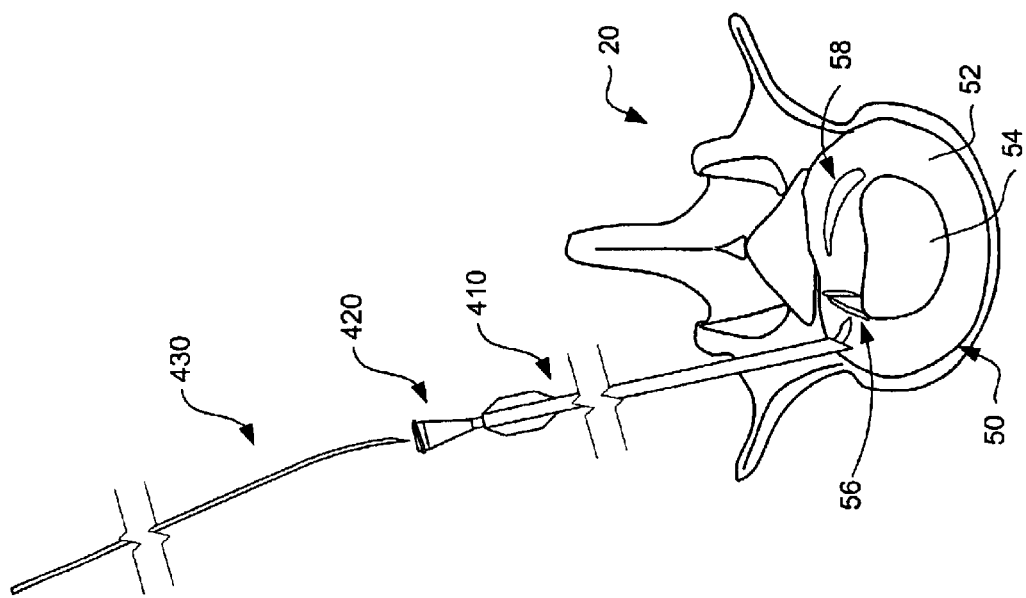

The sharpened stylet 430 is then positioned for insertion into the semi-rigid needle 420 as shown in FIG. 8E. The sharpened stylet 430 is advanced relative to the semi-rigid needle 420 until the distal tip 433 of the stylet 430 extends across radial fissures 56, as shown in FIG. 8F.

Figure 8H:
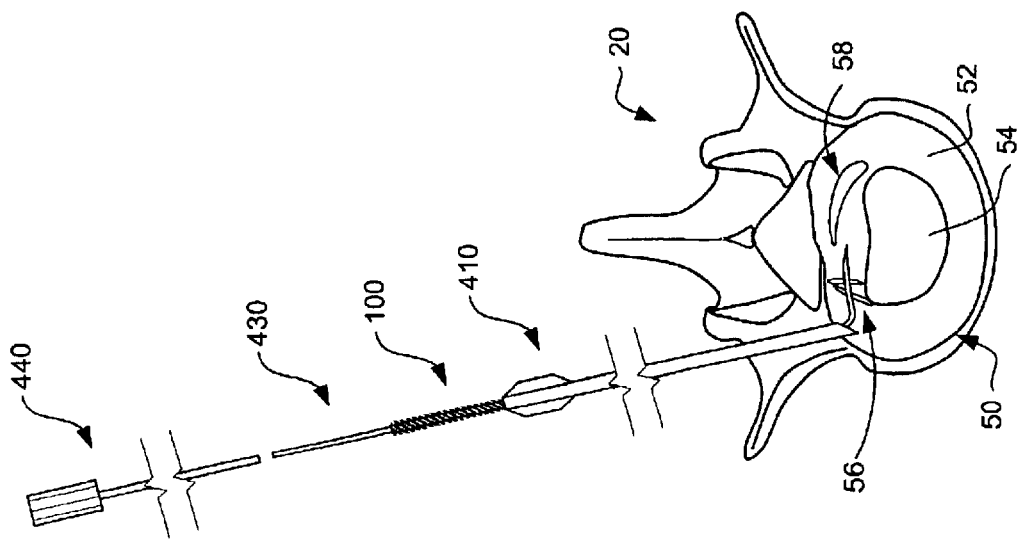
Figure 8G:
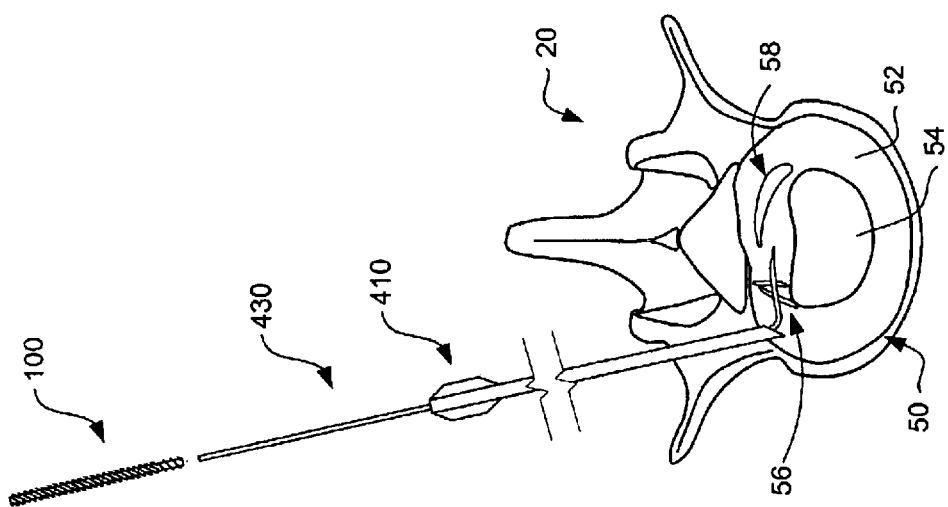
Figure 8I:
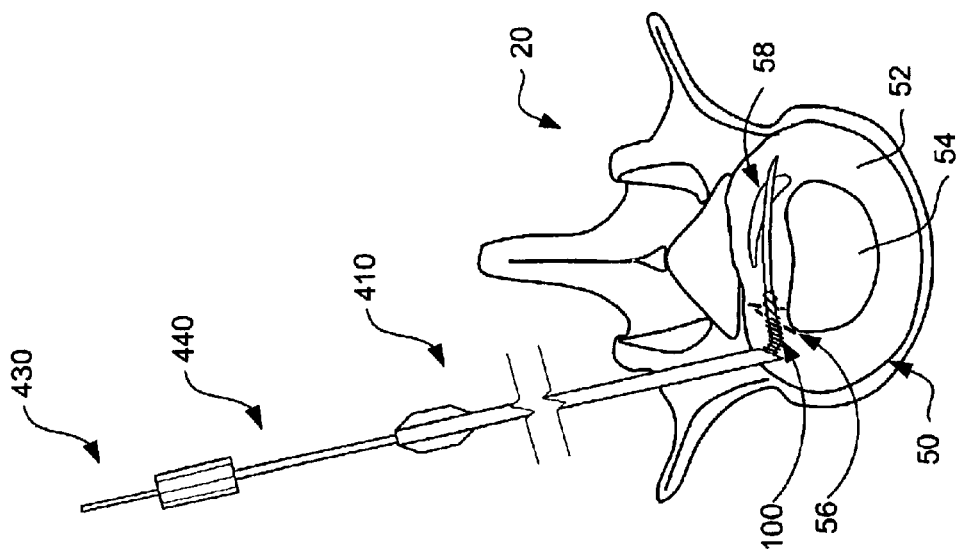

The semi-rigid curved needle 420 is removed from the stylet 430 and trocar 410, and the reinforcement member 100 is positioned for advancement over the stylet 430 as shown in FIG. 8G. The reinforcement member 100 is advanced over the stylet 430 and into the trocar 410, and the driver 440 is positioned for advancement over the stylet 430 as shown in FIG. 8H. The driver 440 is then rotated and advanced over the stylet 430 in order to rotate and push the reinforcement member 100 into the annulus and across the radial fissures 56 as seen in FIG. 8I. If the reinforcement member 100 utilizes an anchor other than threads, the driver 440 may be used to simply push or otherwise advance the reinforcement member 100 through the trocar 410 and into the annulus 52.

If a solid cross-section reinforcement member 100 is utilized, it is not necessary to utilize the stylet 430. In this situation, the curved semi-rigid needle 420 is left in place as shown in FIG. 8E and the solid cross-section reinforcement member 100 is advanced therethrough. The driver 440 is then rotated and advanced through the curved semi-rigid needle 420 in order to rotate and push the reinforcement member 100 into the annulus 52 and across the radial fissures 56. In this alternative method, it may be necessary to resize the curved semi-rigid needle 420 to accommodate the driver 440 and reinforcement member 100.

The variable pitch threads on the reinforcement member 100 compress the disc 50 and cause the fissures 56 to close as discussed previously. If variable pitch threads are not utilized on the reinforcement member 100, other techniques may be used to compress the disc 50 and close the radial fissures 56. An example of an alternative disc 50 compression technique is a step-wise advancement and tension method. In this alternative method, the distal tip 433 of the stylet 430 is incorporated with an anchor 435 such as threads. After the distal tip 433 of the stylet 430 has been advanced by rotation to extend across the fissures 56, and before the reinforcement member 100 has been advanced into the annulus 52, the stylet is pulled in the proximal direction to apply tension thereto. Because the threaded anchor at the distal end 433 of the stylet 430 grips the annulus 52, tension applied to the stylet 430 compresses a portion of the disc 50 and closes the fissures 56. Once compression of the disc 50 and closure of the fissures 56 are established, the reinforcement member 100 may be advanced into the annulus 52 to maintain disc 50 compression and hold the fissures 56 closed. This method of step-wise advancement and tension may be repeated until the reinforcement member 100 is fully implanted in the desired position within the annulus 52.

Figure 8J:
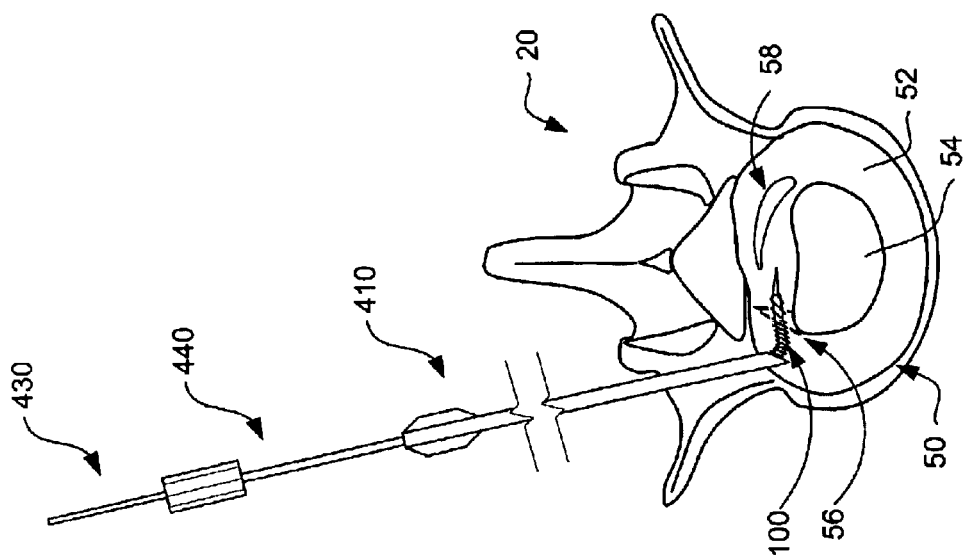
Figure 8L:
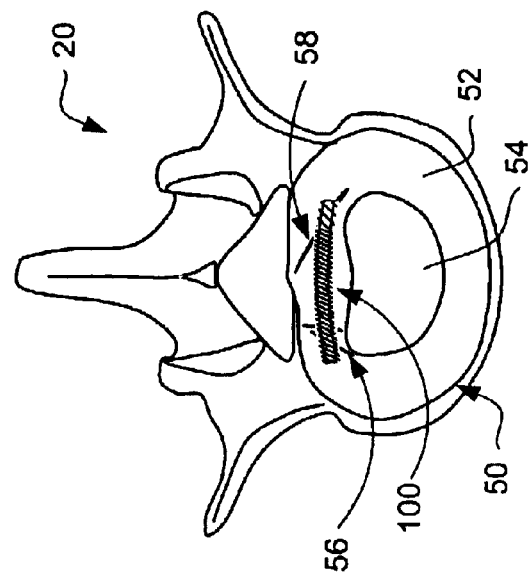
Figure 8K:
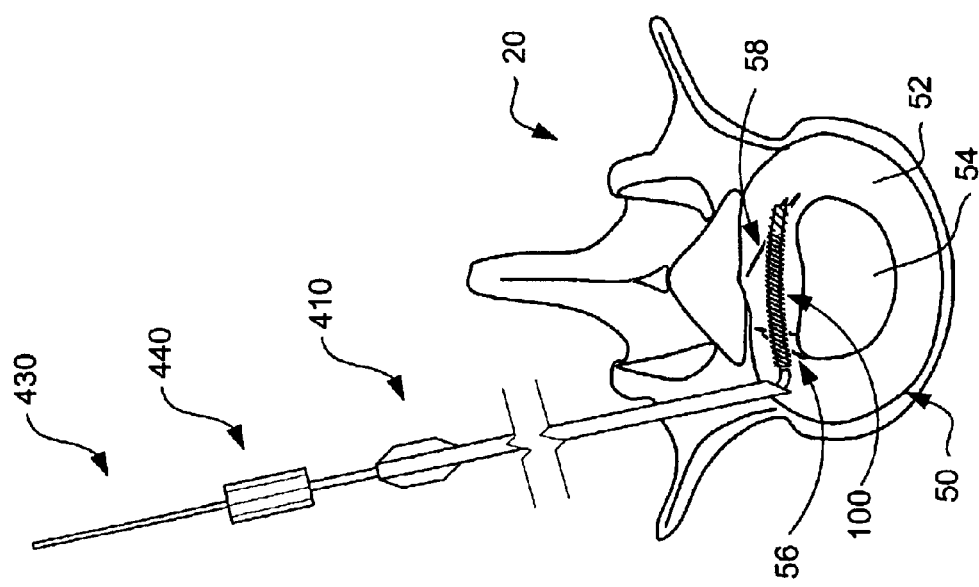

After the reinforcement member 100 is positioned across the radial fissures 56 as shown in FIG. 8I, the stylet is advanced until the distal tip extends across the circumferential fissure 58 as shown in FIG. 8J. Note that the curvature 434 of the stylet 430 defines the insertion path of the reinforcement member 100. It has been observed that the preset curvature 434 of the stylet 430 will correspond to the insertion path if the tip 433 is very sharp. With the stylet 430 advanced such that the tip extends across fissure 58, the driver 440 is then used to rotate and advance the reinforcement member 100 across the fissure 58 as shown in FIG. 8K. The variable pitch threads on the reinforcement member 100 compress the disc 50 and cause the fissure 58 to close as discussed previously. Once the reinforcement member 100 is completely deployed within the annulus 52 as shown in FIG. 8L, the tools 410/430/440 may be removed from the patient and the procedure is essentially complete.

Figure 9A:
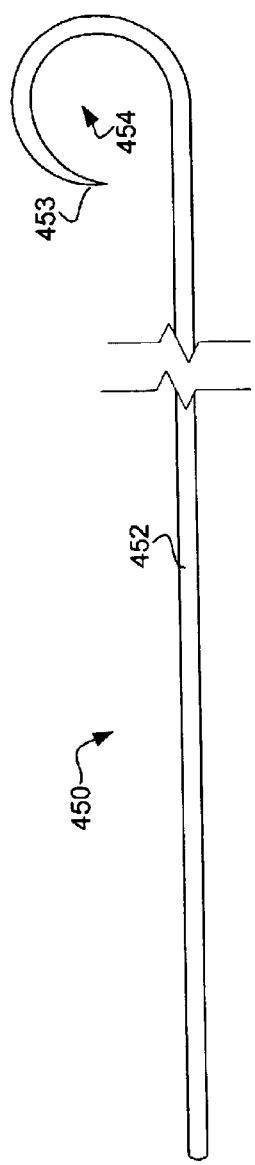
Figure 9B:
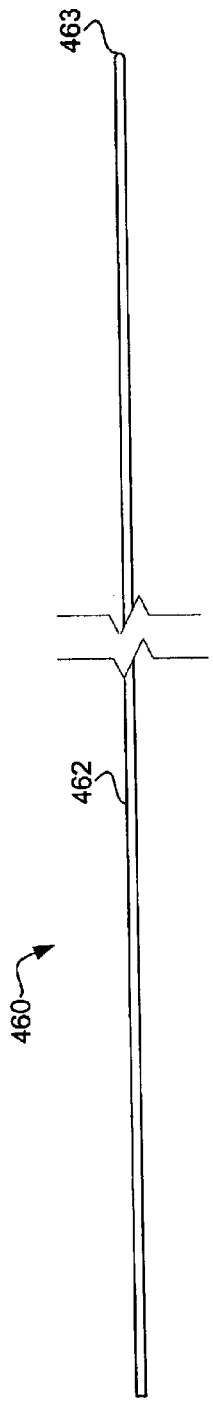
Figure 9C:
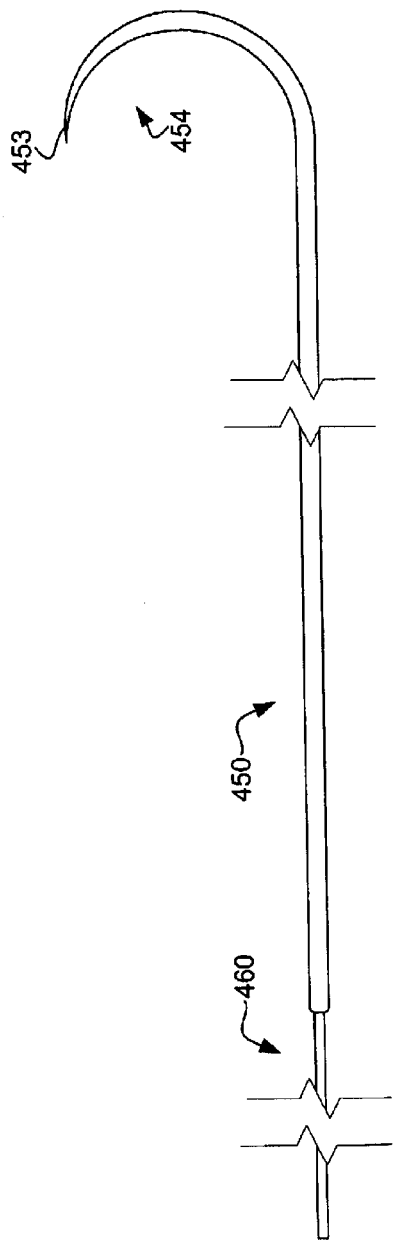

With general reference to FIGS. 9A–9F, schematic illustrations of additional tools 450/460/720 for use in the method of implanting reinforcement member 200 are shown. The additional tools include a variable curvature stylet 450 as shown in FIG. 9A, a stiffening mandrel 460 as shown in FIG. 9B, and an advancement tool 720 as shown in FIG. 9D. The variable curvature stylet 450 is hollow which permits insertion of the stiffening mandrel 460 as shown in FIG. 9C.

As seen in FIG. 9A, the variable curvature stylet 450 includes a tubular shaft 452, a curved distal portion 454 and a closed distal end 453 which is sharpened. The variable curvature stylet 450 is substantially the same as the curved stylet 430 described previously, except for the provision of a lumen into which the stiffening mandrel 460 is insertable. As seen in FIG. 9B, the stiffening mandrel 460 includes an elongate shaft 462 and a blunt tip 463. The shaft 462 and tip 463 of the stiffening mandrel 460 are sized to be inserted into the hollow shaft 452 of the stylet 450. The hollow stylet 450 and the stiffening mandrel 460 may be made of stainless steel, nickel titanium alloy or the like.

As can be seen from a comparison of FIGS. 9A and 9C, upon insertion of the stiffening mandrel 460 into the hollow stylet 450, the curvature increases. Preferably the stiffening mandrel 460 is inserted fully into the hollow stylet 450 to increase the radius of curvature of the distal portion of the curvature 454, since the distal portion of the curvature 454 dictates the path that the stylet 450 will follow. The relative stiffness of the stylet 450 and stiffening mandrel 460 may be selected to vary the amount of change in the curvature 454. The variable curvature 454 may be used to navigate around the changing curvature of the annulus 52 as described hereinafter. At any point during advancement of the stylet 450, the curvature 454 may be adjusted by insertion of an appropriately stiff mandrel 460. The path defined by the stylet 450 may thus be customized to any particular disc 50 anatomy.

As seen in FIG. 9D, advancement tool 720 may be optionally employed to drive the distal end of the hollow stylet 450 through annular tissue 52. The advancement tool 720 includes an elongate tubular shaft 722, with a handle 724 connected to its proximal end and a plurality of threads 726 connected to its distal end. The tubular shaft 722 of the advancement tool 720 includes a lumen which is sized to accommodate the variable curvature stylet 450 therein. To transfer forces from the distal end of the advancement tool 720 to the distal end of the stylet 450, the variable curvature stylet 450 may include a tapered collar 456. With this arrangement, the advancement tool 720 may be advanced over the variable curvature stylet 450 until the distal end of the shaft 722 abuts the collar 456 on the variable curvature stylet 450. During use, the threads 726 engage the annular tissue 52 and upon rotation, apply longitudinal forces against the collar 456, and thereby cause distal advancement of the variable curvature stylet 450. The threads 726 are rotated by manually rotating handle 724, which transmits torsional forces along the elongate shaft 722 to the distal threads 726. To provide adequate transmission of torsional forces, the tubular shaft 722 may further comprise a composite structure as illustrated in FIG. 9E or metallic tubular structure as illustrated in FIG. 9F.

With specific reference to FIG. 9E, the tubular shaft 722 comprises a composite structure having an outer layer 721 disposed about a reinforcement layer 723 disposed about an inner layer 725. The outer layer 721 and the inner layer 725 may comprise a polymeric material having a relatively low coefficient of friction such as PTFE or HDPE. The reinforcement layer 723 is preferably torsionally rigid in both directions of rotation, as may be provided by an interwoven wire braid or by multiple wire coils wound in opposite directions.

With specific reference to FIG. 9F, the elongate tubular shaft 722 comprises a tube 727 which may be formed of a highly elastic and rigid metal such as stainless steel, nickel titanium alloy, or the like. The metallic tube 727 includes a plurality of slots 729 spaced at regular increments along the length of the shaft 722. The slots 729 extend through the wall of the metallic tube 727, but do not extend about the entire circumference of the metallic tube 727. Thus, the slots 729 impart flexibility to the flexible tube 727, while maintaining torsional rigidity thereof.

With general reference to FIGS. 10A–10H, the steps for implanting circumferential reinforcement member 200 are illustrated. All of the variables with regard to quantity, location, orientation, etc. discussed previously may be implemented by varying the generic procedure described hereinafter. The method illustrated in FIGS. 10A–10H is a percutaneous procedure in which access to the disc 50 is achieved utilizing a number of small diameter tools which may be inserted through a patient's back (skin and back muscles), between adjacent vertebrae, and into the patient's disc 50.

Figure 10B:
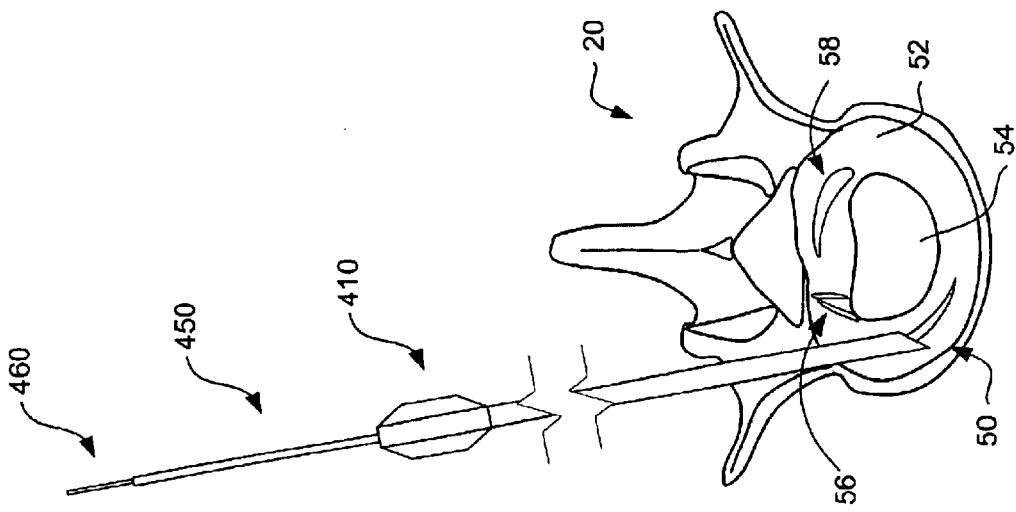
FIGS. 10A–10H illustrate a method for implanting the reinforcement member shown in FIG. 3C in accordance with an embodiment of the present invention.
Figure 10A:
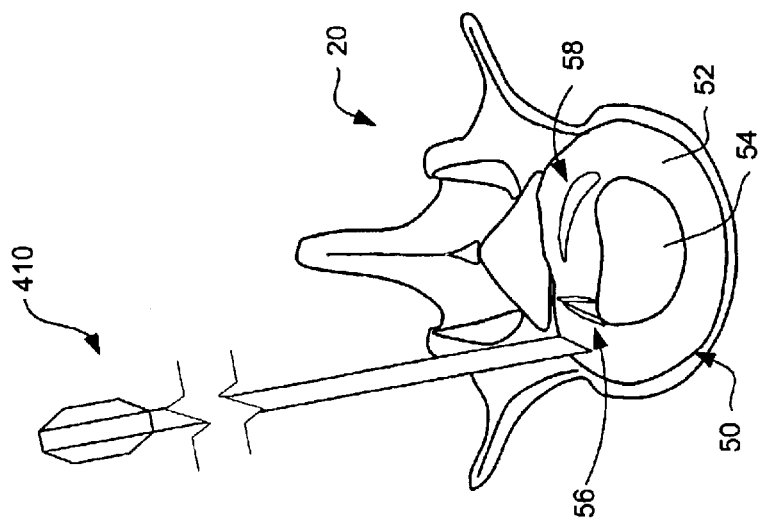

Initially, as shown in FIG. 10A, the rigid trocar 410 is advanced into the annulus 52 of the disc 50. The trocar 410 is advanced until the distal tip 413 thereof is disposed in the lateral portion of the annulus 52 roughly half way between the posterior and anterior portions of the annulus 52 as seen in FIG. 10B. The hollow curved stylet 450 with the stiffening mandrel 460 inserted therein is then advanced into the trocar 410. Note that an appropriate stiff mandrel 460 has been fully inserted into the hollow stylet 450 a sufficient distance to define a curvature 454 that approximates the curvature of the anterior portion of the annulus 52. Continued advancement of the hollow stylet 450 and stiffening mandrel 460 as a unit cause the stylet 450 to traverse the anterior portion of the annulus 52 as shown in FIG. 10C.

Figure 10D:
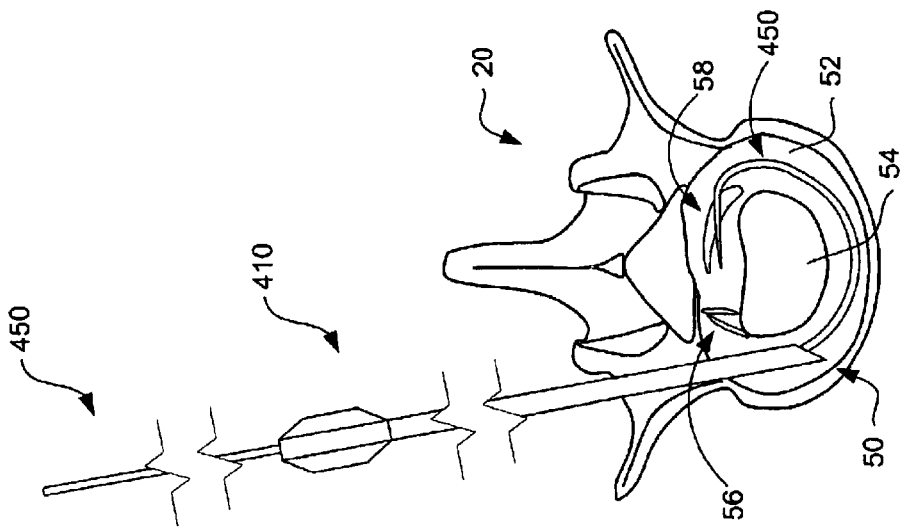
Figure 10C:
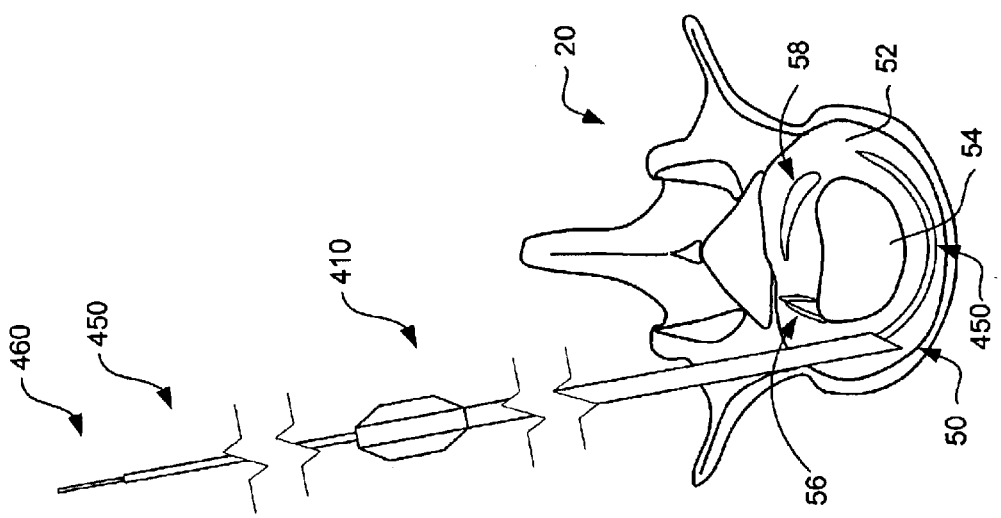

After the distal tip 453 of the stylet 450 is positioned roughly half way between the posterior and anterior portions of the annulus 52 as seen in FIG. 10C, the stiffening mandrel 460 is retracted or removed from the stylet 450 to define a smaller curvature 454 that approximates the curvature of the posterior lateral portion of the annulus 52. The stylet 450 is then advanced until the distal tip 453 thereof enters the posterior portion of the annulus 52 as shown in FIG. 10D.

An appropriately stiff mandrel 460 is then advanced or inserted into the hollow stylet 450 to define a curvature 454 that approximates the curvature of the posterior portion of the annulus 52. The stylet is then advanced across the posterior portion of the annulus 52. The stiffening mandrel 460 is then retracted or removed from the stylet 450 to define a smaller curvature 454 that approximates the curvature of the posterior lateral portion of the annulus 52. The stylet 450 is then advanced until the distal tip 453 thereof is positioned adjacent the distal tip 413 of the trocar 410 as shown in FIG. 10E.

Figure 10F:
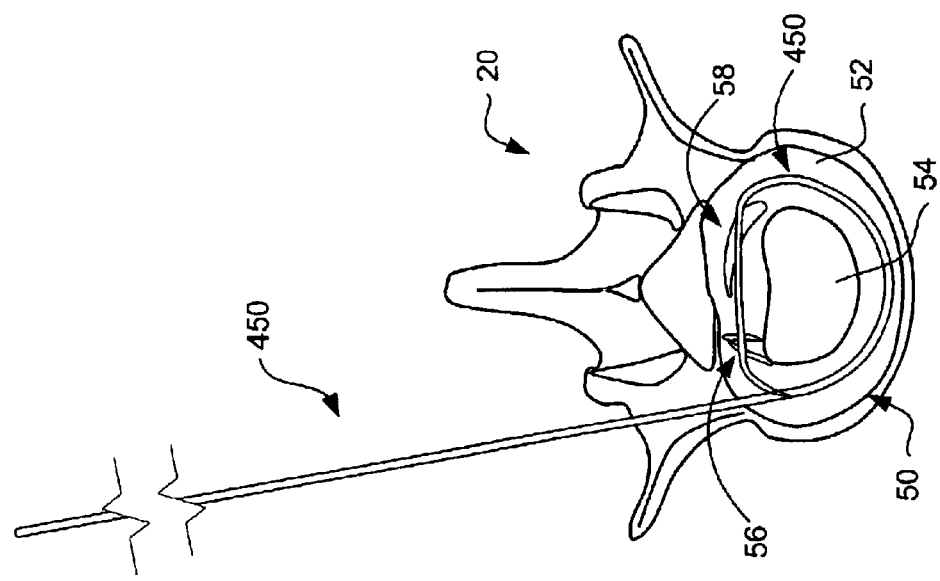
Figure 10E:
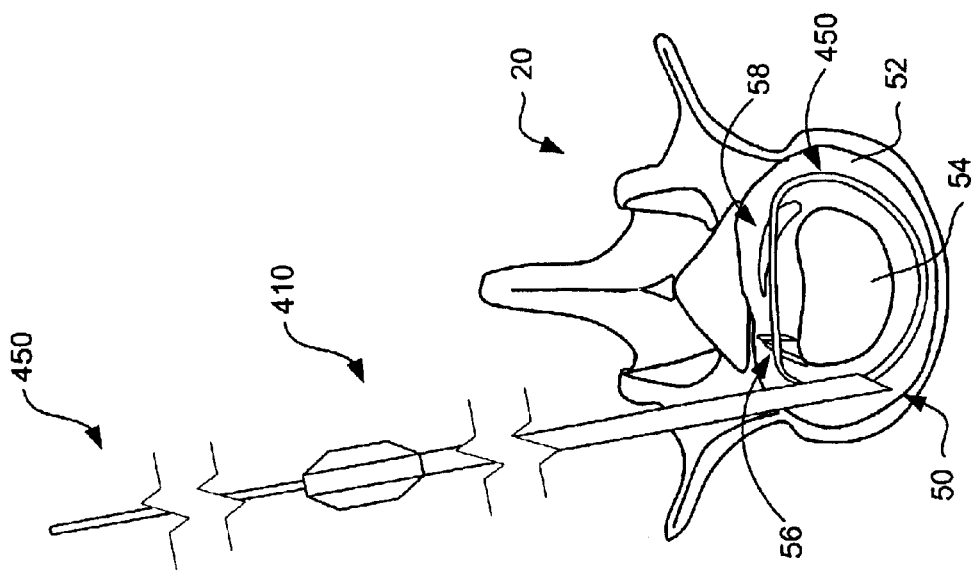
Figure 10H:
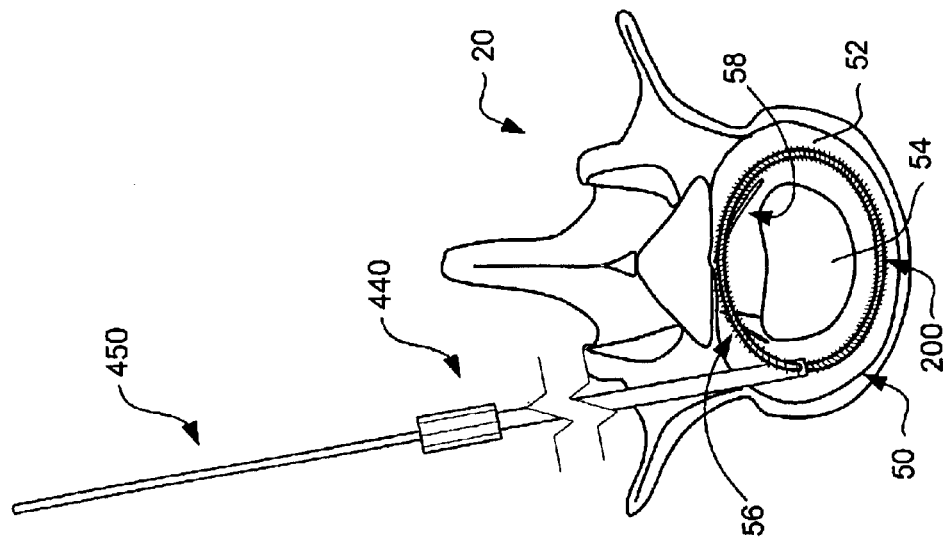
Figure 10G:
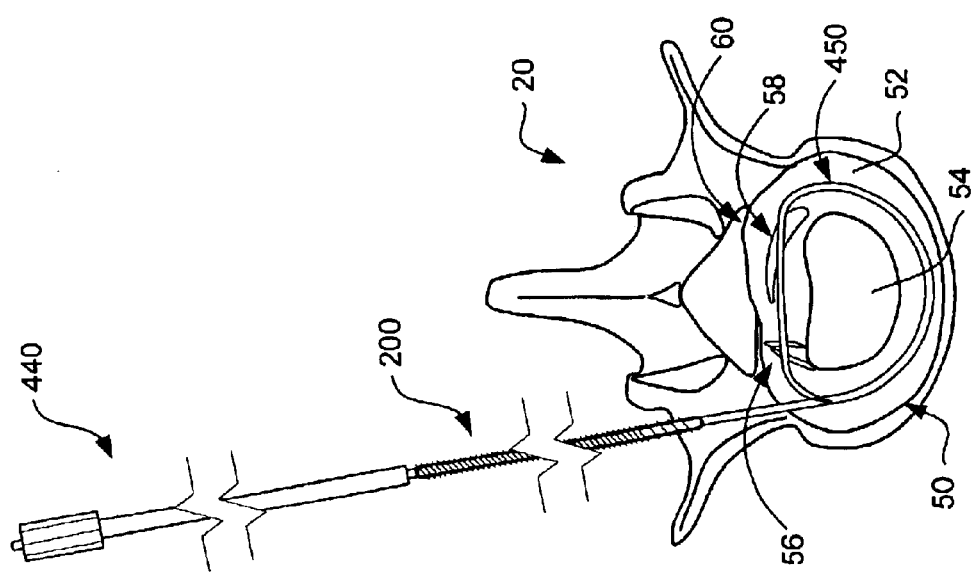

The trocar 410 is then removed from the patient leaving the stylet 450 in the annulus 52 to define the insertion path for the reinforcement member 200 as shown in FIG. 10F. The circumferential reinforcement member 200 and driver 440 are then advanced over the stylet 450 as shown in FIG. 10G. Using the driver 440 to push and rotate the circumferential reinforcement member 200, the member 200 is advanced into the annulus 52 along the path defined by the stylet 450 until the distal end of the reinforcement member 200 is adjacent the proximal end of the reinforcement member 200. Note that the variable pitch threads 222 compress the disc 50 and cause the fissure 56/58 to close. If the reinforcement member 200 includes an anchor 220 other than threads (e.g., sloped rings, barbs, etc.) the driver 440 may be used to simply push the reinforcement member 200 into the annulus 52. Once the reinforcement member 200 is in the desired position, the driver 440 and stylet 450 may be removed from the patient to complete the procedure.

With general reference to FIGS. 11A–11H, the steps for implanting reinforcement member 300 are illustrated. All of the variables with regard to quantity, location, orientation, etc. discussed previously may be implemented by varying the generic procedure described hereinafter. The method illustrated in FIGS. 11A–11H is a percutaneous procedure in which access to the disc 50 is achieved utilizing a number of small diameter tools which may be inserted through a patient's back (skin and back muscles), between adjacent vertebrae, and into the patient's disc 50.

Figure 11B:
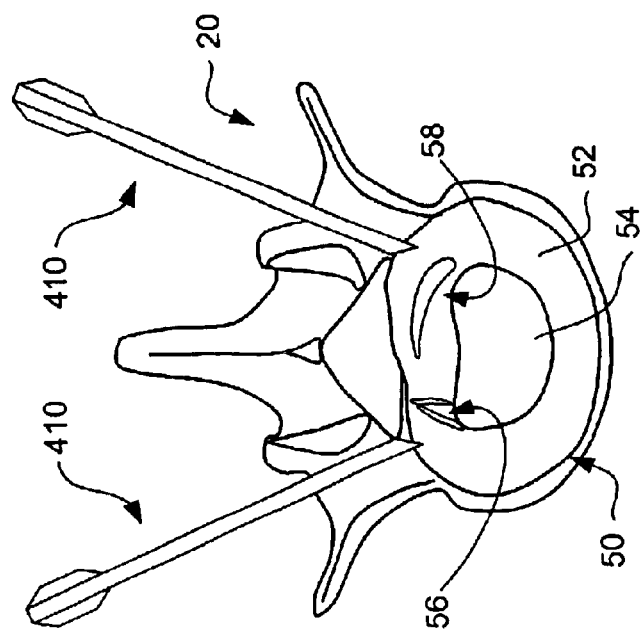
Figure 11A:
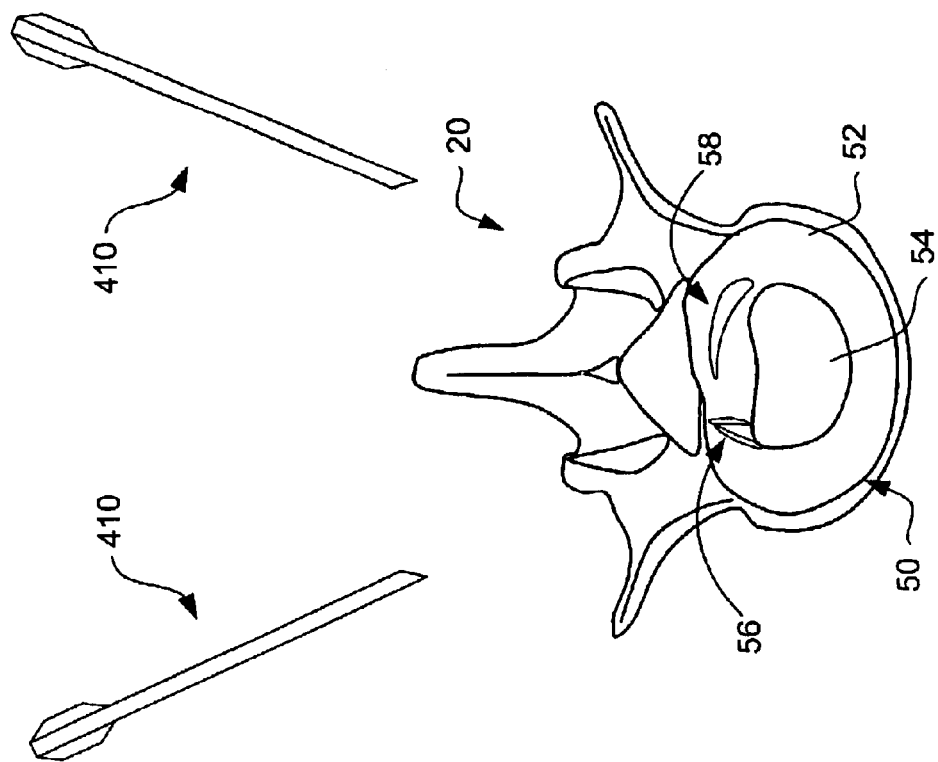
Figure 11D:
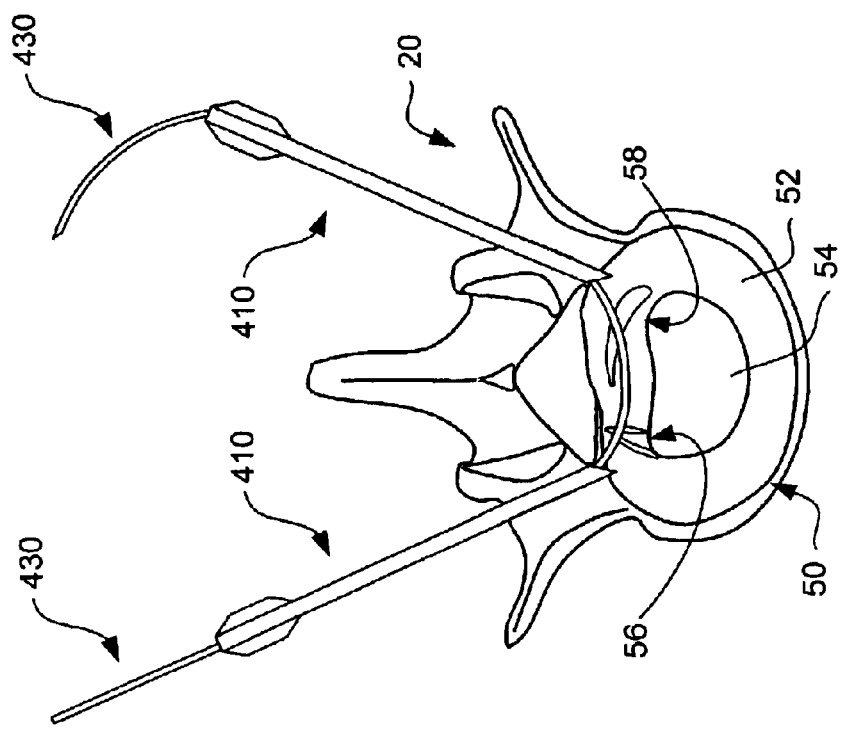
Figure 11C:
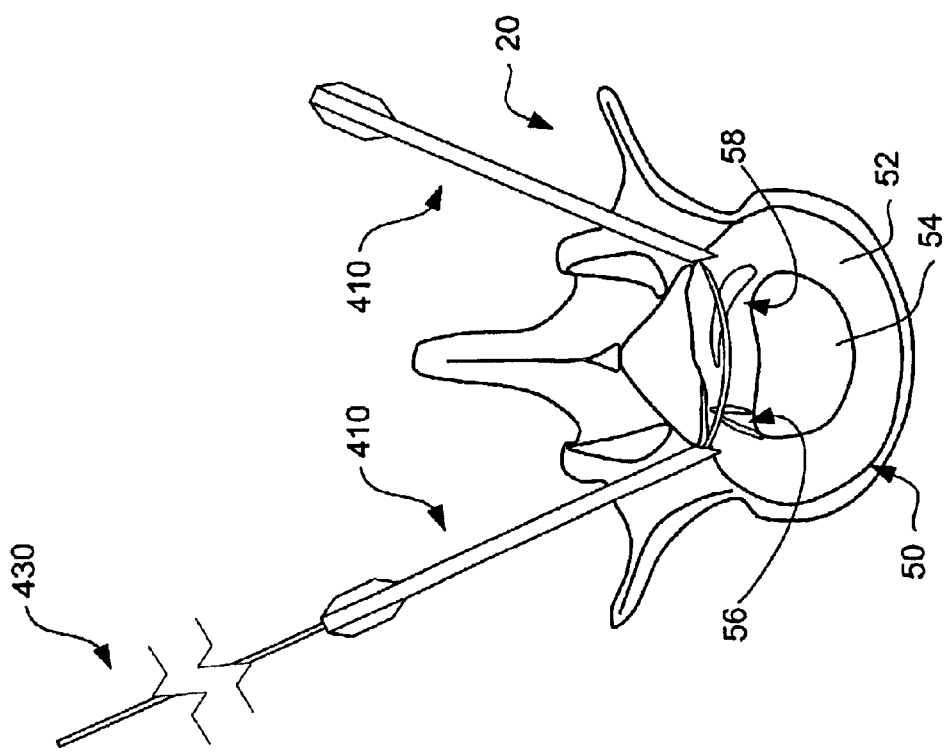

Initially, as shown in FIG. 11A, two trocars 410 are positioned for insertion into the disc 50. The trocars 410 are advanced until the distal tip 413 of each trocar 410 is proximate the outer periphery of the posterior portion of the annulus 52 as seen in FIG. 11B. The curved stylet 430 is then advanced into one of the trocars 410 and advanced into the annulus 52 as shown in FIG. 11C. The curved stylet 430 is then advanced across the posterior annulus 52, into the distal tip 413 of the other trocar 410, and out the proximal end of the other trocar 410 as shown in FIG. 11D. The curvature 434 of the stylet 430 is selected such that the tip 433 of the stylet 430 traverses the posterior portion of the annulus 52 and automatically enters into the other trocar 410. To facilitate automatic insertion of the stylet into the other trocar 410, the inside diameter of the trocar 410 may be tapered to increase the inside diameter closer to the tip 413. As mentioned previously, the stylet 430 will follow a path in the annulus 52 corresponding to the curvature 434 of the stylet 430 if the tip 433 is very sharp.

Figure 11F:
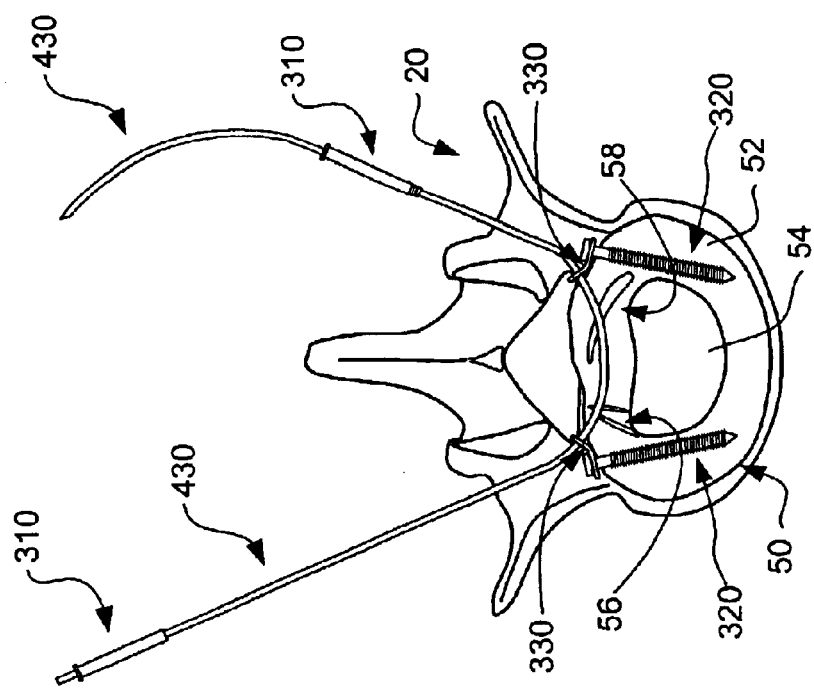
Figure 11E:
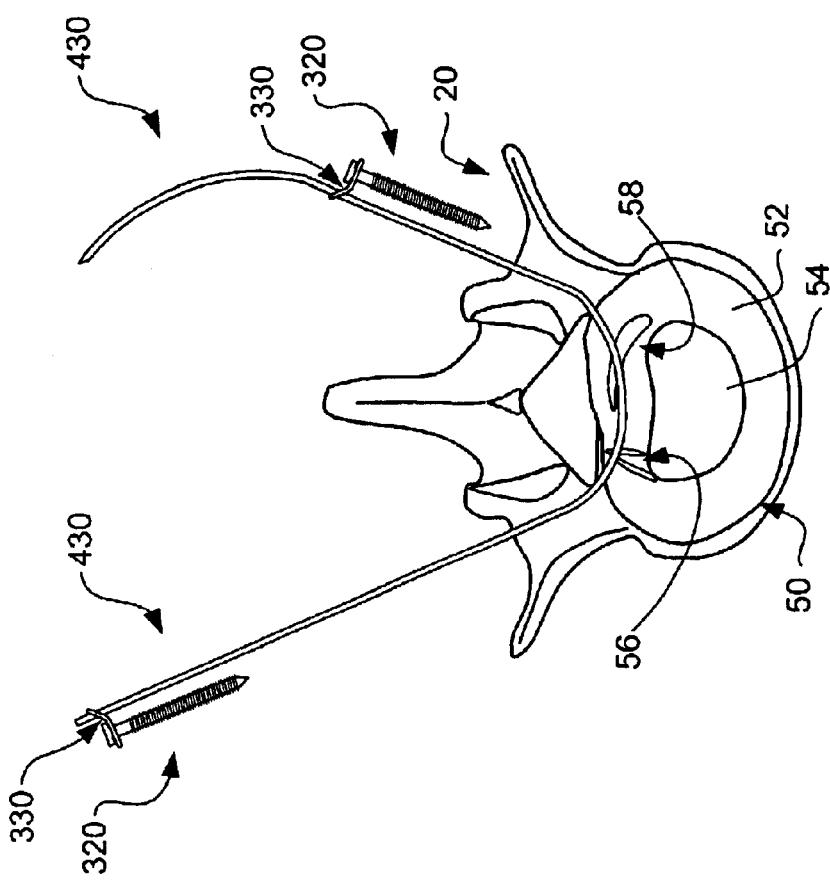

The trocars 410 are then removed from the patient leaving the stylet 430 in place as shown in FIG. 11E. Also as shown in FIG. 11E, the screws 320 are placed in the holes 334 of the connection rings 330, and the connection rings 330 are slid onto the stylet 430 through holes 332. The screws 320 are then screwed into the annulus 52 as shown in FIG. 11F using a conventional driver (not shown). Placing the screws 320 in the lateral portions of the annulus 52 takes advantage of the generally greater integrity (usually thicker and healthier) of the lateral portions of the annulus 52 to establish firm anchor points.

Also as shown in FIG. 11F, the tubular pins 310 are positioned on the stylet 430. The tubular pins 310 are then advanced over the stylet 430, across the posterior portion of the annulus 52, and screwed together as shown in FIG. 11G using driver 440 (not shown). The pins 310 are have an assembled length which is shorter than the length of the stylet traversing the annulus 52 such that connection of the pins 310 causes compression of the disc 50 and closure of the fissures 56/58. After removal of the stylet 430, the screws 320 may be tightened further into the annulus 52 in order to further compress the disc 50 and close the fissures 56/58 as shown in FIG. 11H.

With general reference to FIGS. 12A–12G, FIGS. 13–15, FIGS. 16A–16E, and FIGS. 17A–17D, schematic illustrations of additional tools 710/730/740/750/800/900 are shown for use in implanting reinforcement member 600 in accordance with the method illustrated in FIGS. 18A–18L. The additional tools include a curved stylet or needle 710 as shown FIGS. 12A–12G, a guide tube or sheath 730 as shown in FIG. 13, a pledget push rod 740 as shown in FIG. 14, a pledget 750 as shown in FIGS. 14 and 15, a column support and advancement device 800 for stylet 710 as shown in FIGS. 16A–16E, and a column support and advancement device 900 for stylet 710 and sheath 730 as shown in FIGS. 17A–17D. Tools 710/730/800/900 and the associated method may be utilized to implant other reinforcement members described herein, including reinforcement members 100/200/300.

With specific reference to FIGS. 12A–12G, the stylet or needle 710 includes a flexible elongate shaft 711 and a sharpened distal end 714. The stylet 710 is similar to the curved stylet 430 described with reference to FIG. 7C, except as described herein and apparent from the drawings. The stylet or needle 710 may have a substantially straight distal portion 712A as shown in FIG. 12A. Alternatively, the stylet 710 may be curved as illustrated in FIGS. 12B–12E.

For example, in FIG. 12A, the stylet 710A includes a straight distal portion 712A. In FIG. 12B, the stylet 710B includes a curved portion 712B having a curvature that may, for example, correspond to the anterior curvature of the annulus 52. In FIG. 12C, the stylet 710C includes a curved portion 712C having a curvature that may, for example, correspond to the curvature of the lateral portions of the annulus 52. In FIG. 12D, the stylet 710D includes a distal curved portion 712D having a curvature that permits relatively sharp turns or counter-turns during navigation through the annulus 52. In FIG. 12E, the stylet 710E has a primary curvature 712E and a secondary opposite curvature 716E proximal thereon. The provision of a primary curvature 712E in addition to a secondary opposite curvature 716E allows the stylet 710E to change directions during navigation within the annulus 52. To this end, the secondary curvature 716E may have a curvature corresponding to the path already defined through the annulus 52 during navigation, and the primary curvature 712E may have a curvature corresponding to the path to be taken by the stylet 710E upon further advancement through the annulus 52. Although a limited number of distal configurations 712 have been illustrated, it is contemplated that a variety of stylets 710 having a variety of distal geometries 712 may be employed during the implantation procedures described hereinafter.

The shaft 711 of the stylet 710 preferably has a flexible but pushable construction incorporating a rigid metal mandrel such as stainless steel, or a super-elastic alloy such as nickel-titanium. Highly elastic or super-elastic materials incorporated into the elongate shaft 711 resist permanent deformation during insertion and navigation through the annulus 52. The shaft 711 of the stylet 710 may have a diameter ranging from 0.010 to 0.025 inches, which may vary depending on the tortuosity of the annular path and the characteristics (toughness, friction) of the annular material 52. The shaft 711 may be coated with a lubricious material such as PTFE and a hydrophilic polymer.

It has been found that if the tip 714 is sufficiently sharp to easily penetrate annular tissue 52, the path through the annular tissue 52 taken by the stylet 710 will substantially conform to the geometry of the distal portion 712 of the stylet 710. In particular, if the distal portion 712 is substantially straight, the stylet 710 will define a linear path through the annular tissue 52. Alternatively, if the distal portion 712 has a curve or other nonlinear geometry (in a relaxed state), the stylet 710 will define a path through the annular tissue 52 corresponding to the shape of the distal portion 712. To this end, it is desirable to provide a tip 714 having sufficient sharpness to readily penetrate annular tissue 52, which tends to be relatively fibrous and tough. The distal tip 714 may have a symmetrical geometry 714A as illustrated in FIG. 12F or an asymmetrical geometry 714B as illustrated in FIG. 12G, and preferably has a fine to micro-fine sharpness. By providing a sufficiently sharp tip 714, navigation through the annulus 52 may be performed in a predictable manner as described in more detail hereinafter.

With specific reference to FIG. 13, the guide tube or sheath 730 includes an elongate tubular shaft 732 having a lumen extending therethrough sized to accommodate the stylet 710. The guide tube or sheath 730 preferably has a relatively thin wall structure so as to minimize the increase in profile relative to the stylet 710. In addition, the inside surface of the shaft 732 preferably has a low friction coating or liner such as PTFE to minimize friction between the guide sheath 730 and the stylet 710. The guide sheath 730 preferably is able to withstand relatively high longitudinal compressive forces and therefore, preferably comprises a relatively rigid but flexible material such as PTFE or polyimide. For example, the tubular shaft 732 may comprise a polyimide tube having an inside diameter approximately 0.0005 to 0.001 inches greater than the outside diameter of the stylet 710, with a wall thickness of approximately 0.0005 to 0.003 inches. The tubular shaft 732 may further incorporate a reinforcement layer such as a metallic braid or the like to help prevent various modes of buckling.

With specific reference to FIG. 14, the pledget push rod 740 includes an elongate rigid shaft 742 comprising, for example, a stainless steel rod. The distal end of the shaft 742 is connected to pledget 750 by way of a releasable connection 744. Releasable connection 744 may comprise, for example, a weakened area of the rod 742 or pledget 750 that may be broken by application of torsional forces to the rod 742.

With specific reference to FIG. 15, the pledget 750 includes a body portion 752 and two holes 754 sized to accommodate the stylet 710 and reinforcement member 600. The body portion 752 may comprise a metallic or polymeric material. Examples of suitable metallic materials include stainless steel and super-elastic alloys such as nickel-titanium. If the body portion 752 comprises a polymeric material, the polymeric material may be biologically inert, biodegradable or bioabsorbable. Examples of suitable polymeric materials comprising biologically stable or inert materials include HDPE and PTFE. Examples of biodegradable or bioabsorbable materials include resorbable collagen, LPLA (poly(l-lactide)), DLPLA (poly(dl-lactide)), LPLA-DLPLA, PGA (polyglycolide), PGA-LPLA or PGA- DLPLA. The body portion 752 of the pledget 750 may be coated with biocompatible materials, growth factors to facilitate healing, agents which render the nuclear matter inert or otherwise reduce chemical irritation thereof, and/or anesthetic agents to reduce nerve signal transmission (i.e., pain).

With specific reference to FIGS. 16A–16E, the column support and advancement device 800 for use with stylet 710 is shown. Device 810 includes a shaft portion 810 which extends through and is rigidly connected to a proximal handle assembly 812. The distal end of the shaft 810 may incorporate a plurality of threads 814 to rotationally engage and bore through tissues in the back (dermal and muscular tissues) and anchor against tissues immediately adjacent the point of entry into the annulus 52. The distal tip 815 of the shaft 810 may also be sharpened to facilitate penetration through tissues in the back. The shaft 810 comprises a rigid metal tube having a lumen extending therethrough adapted to receive the stylet 710. The inside surface of the tubular shaft 810 may be provided with a low friction liner or coating such as PTFE. Within the handle 812, the shaft 810 includes a slot aligned with a slot or keyway 816 in the handle 812, which is sized and shaped to accommodate key 820. The slot in the shaft 810 contained within the handle assembly 812 has a width that is less than that of the outside diameter of the stylet 710 such that the stylet 710 cannot pass therethrough and such that the shaft 810 provides column support to the stylet 710 and prohibits buckling thereof.

Key 820 includes a thumb button 822 which may incorporate a plurality of grip members 828. A metallic plate 824 extends downwardly from the body portion 822 and has a geometry which substantially conforms to keyway 816. The bottom of the plate 824 incorporates one or more protrusions 826. Protrusions 826 engage and mate with recesses 715 formed in the proximal end of the stylet 710. Protrusions 826 and recesses 715 may be replaced by a wide variety of mating geometries to facilitate engagement between the key 820 and the proximal end of the stylet 710.

Upon depression of the thumb button 822 relative to the handle 812, the plate 824 travels in a downward direction to force the protrusions 826 into the recesses 715. The thumb button 822 may then be advanced in the distal direction, while maintaining downward pressure, to advance the stylet 710 in the distal direction relative to the shaft 810 into annular tissue 52. Although the stylet 710 may encounter substantial resistance during advancement through annular tissue 52, and despite the relative flexibility of the stylet 710, the shaft 810 of the advancement device 800 provides sufficient column strength to the stylet 710 to resist buckling during advancement.

After the key 820 has been advanced to the distal end of the handle 812, the downward force applied to the thumb button 822 may be removed to disengage the protrusions 826 from the recesses 715 in the stylet 710. To facilitate disengagement of the teeth 826 from the recesses 715, a pair of leaf springs 825 may be provided on either side of the plate 824 to urge the key 820 in the upward direction relative to the handle 812. In the disengaged position, the key 820 may be moved to the proximal end of the handle 812, and a downward force may be reapplied to the thumb button 822 to cause engagement of the protrusions 826 with the recesses 715. The thumb button 822 may then be advanced again in the distal direction relative to the handle 812 to advance the stylet 710 further into the annular tissue 52.

This procedure may be repeated until the stylet 710 is advanced the desired distance. In addition, with the key 820 in the disengaged position, the stylet 710 may be removed for a different stylet 710 having a different distal curvature, for example. To exchange the stylet 710, downward pressure against the thumb button 822 is removed to allow the key 820 to be urged in the upward direction by springs 825, to thereby disengage the protrusions 826 from the recesses 715. In the disengaged position, the stylet 710 may be removed from the device 800 by pulling the stylet 710 in the proximal direction. A second stylet 710 may be inserted into the device 800 by inserting the distal end of the stylet 710 into the proximal end of the lumen of the shaft 810 located at the proximal end of the handle assembly 812. The stylet may then be advanced until the distal end thereof exits the distal end of the shaft 810.

With specific reference to FIGS. 17A–17D, column support and advancement device 900 for use with stylet 710 and sheath 730 is shown. Device 900 includes a rigid metallic tubular shaft 910 having a handle 912 connected to its proximal end. A plurality of threads 914 are provided at the distal end of the shaft 910 to facilitate advancement through tissues up to the perimeter of the annulus 52, and to facilitate anchoring of the tubular shaft 910 adjacent the periphery of the annulus 52. The distal tip 915 of the tubular shaft 910 is sharpened to facilitate advancement through dermal and muscular tissues in the back up to and adjacent the annulus 52. The tubular shaft 910 has an inside diameter sized to accommodate the guide sheath 730 which is sized to accommodate the stylet 710. The inside diameter of the tubular shaft 910 may incorporate a low friction coating such as PTFE to minimize friction between the tubular shaft 910 and the tubular sheath 730.

The tubular shaft 910 includes a helical slot 916 which passes through the wall thereof and extends from a point adjacent the handle 912 to a mid portion of the shaft 910. A proximal nut 920 and a distal nut 930 are disposed about the shaft 910 and cooperate with the helical slot 916 such that they may be independently longitudinally advanced and retracted by rotation thereof relative to the shaft 910.

As best seen in FIG. 17B, the proximal nut 920 abuts a collar 918 fixedly connected to the stylet 710. Similarly, the distal nut 930 abuts a collar 732 fixedly attached to the tubular sheath 730. Thus, longitudinal advancement of nut 920 by rotation thereof relative to the shaft 910 causes corresponding longitudinal advancement of the stylet 710. Similarly, longitudinal advancement of nut 930 by rotation thereof relative to shaft 910 causes corresponding longitudinal advancement of the tubular sheath 730.

As seen in FIG. 17C, proximal nut 920 includes a collar 924 connected to a bearing 926 by a pair of arms 922. The arms 922 extend through the helical slot 916 in the shaft 910. The collar 924 extends around the outside of the shaft 910, and the bearing 926 fits within the lumen of the shaft 910. The bearing 926 has an inside diameter sized to accommodate the stylet 710 in an outside diameter sufficient to engage and abut the collar 718, while permitting relative rotational movement. The side openings 928 in the collar 924 and bearing 926 permit the proximal nut 920 to be removed from the shaft 910, which in turn permits the stylet 710 to be removed from the device 900 and replaced with a different stylet 710 having a different distal curvature, for example.

As seen in FIG. 17D, the distal nut 730 includes a collar 934 connected to a bearing 936 by a pair of arms 932. The collar 934 has an inside diameter sufficient to accommodate the outside diameter of the shaft 910. The bearing 936 has an outside diameter sized to fit within the lumen of the shaft 910 and sized to engage and abut the collar 732 on the tubular sheath 730. The bearing 936 also has an inside diameter sufficient to accommodate the tubular sheath 730, while allowing relative rotational movement.

With this arrangement, the stylet 710 may be advanced independently of the sheath 730, and visa-versa. In addition, with this arrangement, both the tubular sheath 730 and the stylet 710 have column support proximal of the path being navigated through the annulus 52.

With general reference to FIGS. 18A–18L, the steps for implanting reinforcement member 600 are illustrated. The method illustrated in FIGS. 18A–18L utilizes stylet 710 to navigate through the annulus 52 and implant reinforcement member 600. The method illustrated in FIGS. 18A–18L may be modified to make use of hollow stylet 450 and stiffening mandrel 460 to navigate through the annulus 52 and implant reinforcement member 600. All of the variables with regard to quantity, location, orientation, etc., discussed previously may be implemented by varying the generic procedure described hereinafter. The method illustrated in FIGS. 18A–18L is a percutaneous procedure in which access to the disc 50 is achieved utilizing a number of small diameter tools which may be inserted through a patient's back (skin and back muscles), between adjacent vertebrae, and adjacent the patient's disc 50.

Figure 18B:
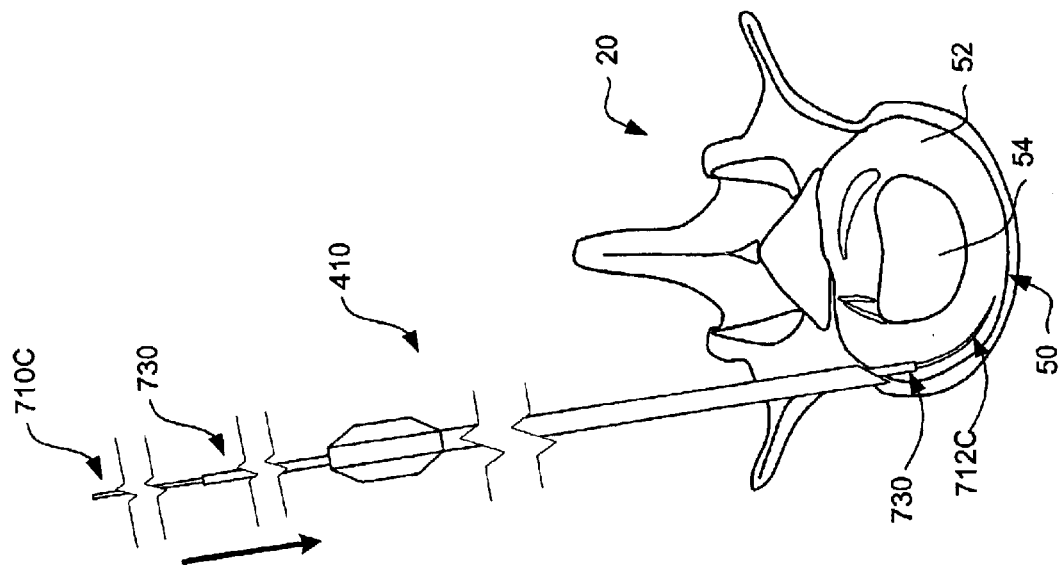
Figure 18A:
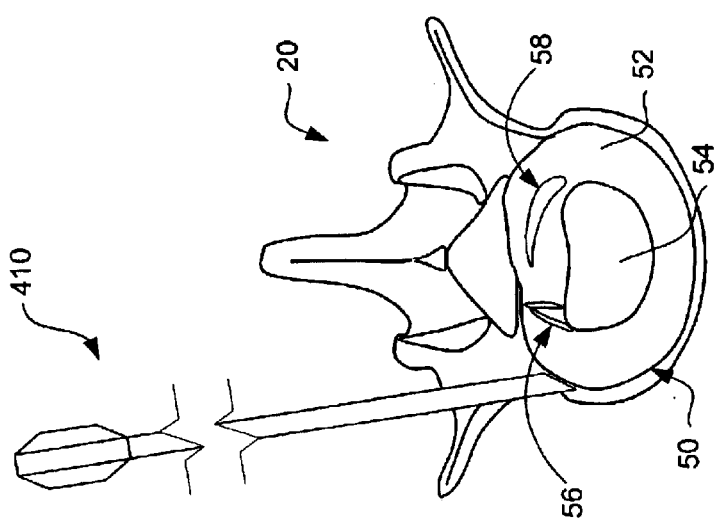

Initially, as shown in FIG. 18A, the rigid trocar 410 is advanced until the distal tip thereof is disposed immediately adjacent the periphery of the annulus 52 of the disc 50. A stylet 710C, with tubular sheath 730 disposed thereon, is inserted into the rigid trocar 410. The stylet 710C, having a curved distal portion 712C, is advanced out the distal end of the trocar 410 into the annulus 52 until the distal end of the stylet 710C is located in the anterior portion of the annulus 52 as shown in FIG. 18B. Note that the curvature of the distal portion 712C roughly corresponds to the curvature of the lateral annulus 52. The sheath 730 may then be advanced over the stylet 710C until the distal end of the sheath is adjacent the distal end of the stylet 710.

Figure 18D:
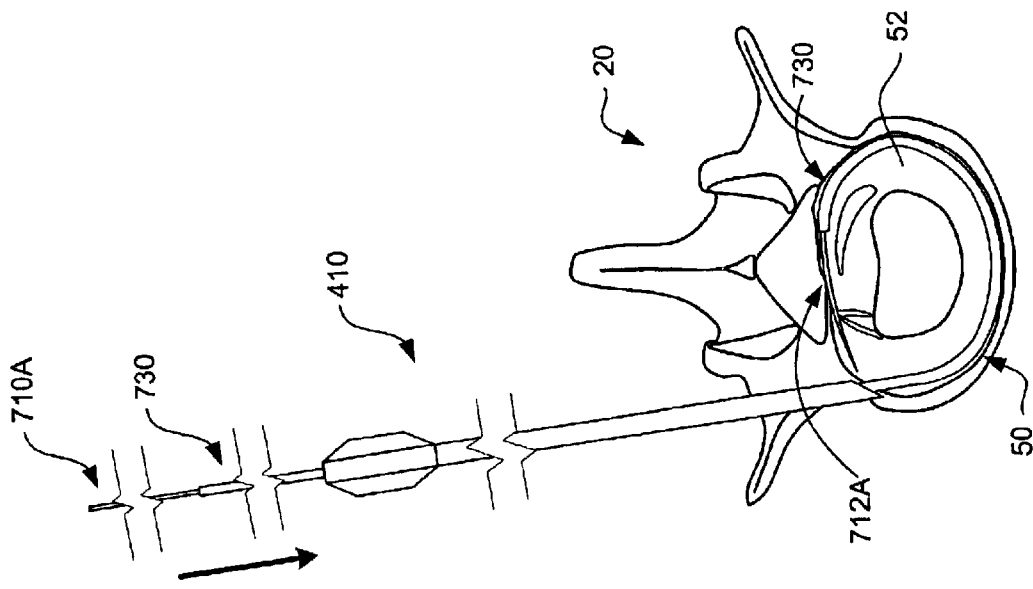
Figure 18C:
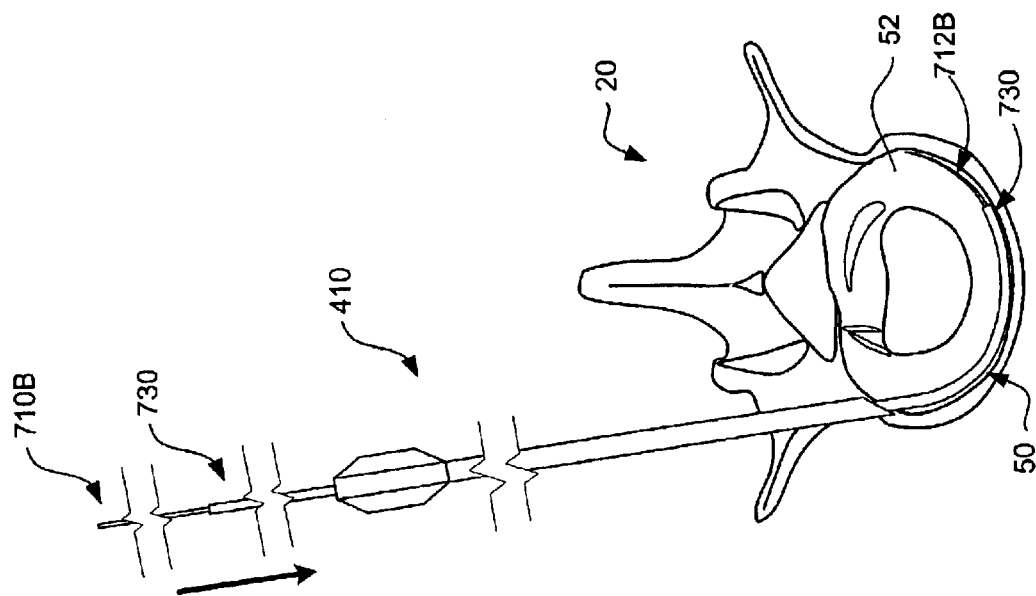

The stylet 710C may then be removed from the sheath 730, and another stylet 710B, having a curved distal portion 712B, may be advanced through the sheath 730 as shown in FIG. 18C. In this manner, the tubular sheath 730 maintains the path defined by the penetrating stylet 710C, and allows the next stylet 710B to begin penetration where stylet 710C left off. The stylet 710B is advanced until the distal tip is positioned in the lateral portion of the annulus, after which the tubular sheath 730 may be advanced thereover. Note that the curvature of the distal portion 712B roughly corresponds to the curvatures of the anterior annulus 52. The stylet 710B may be exchanged for stylet 710C having a curved portion 712C to traverse the lateral side of the annulus 52. The stylet 710C may then be exchanged for another stylet 710A having a relatively straight distal portion 712A to traverse the posterior portion of the annulus 52 as shown in FIG. 18D. The tubular sheath 730 is then advanced over the stylet 710A until the distal end of the sheath 730 is adjacent the distal end of the stylet 710A.

Figure 18F:
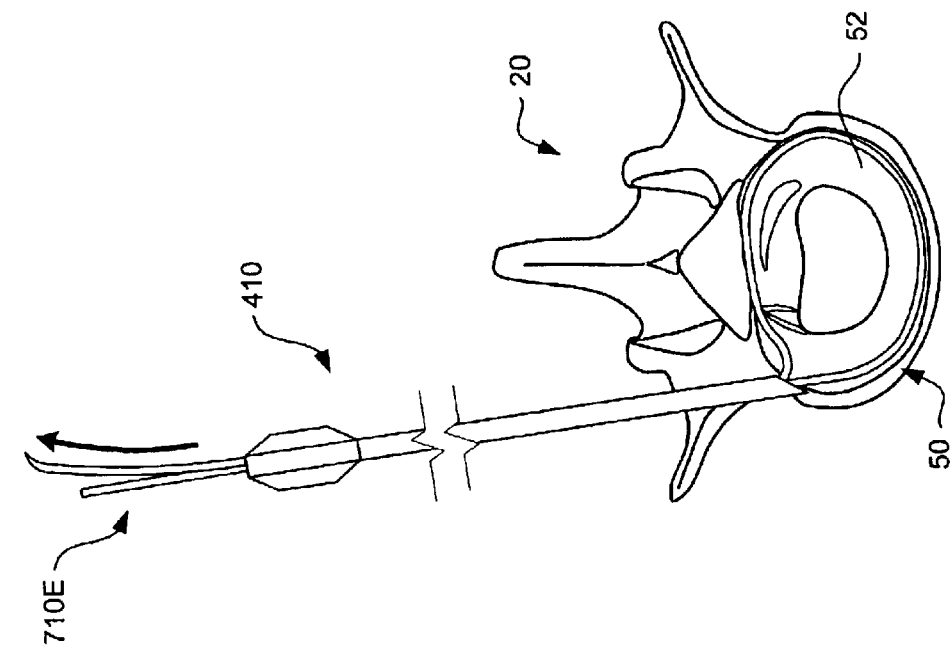
Figure 18E:
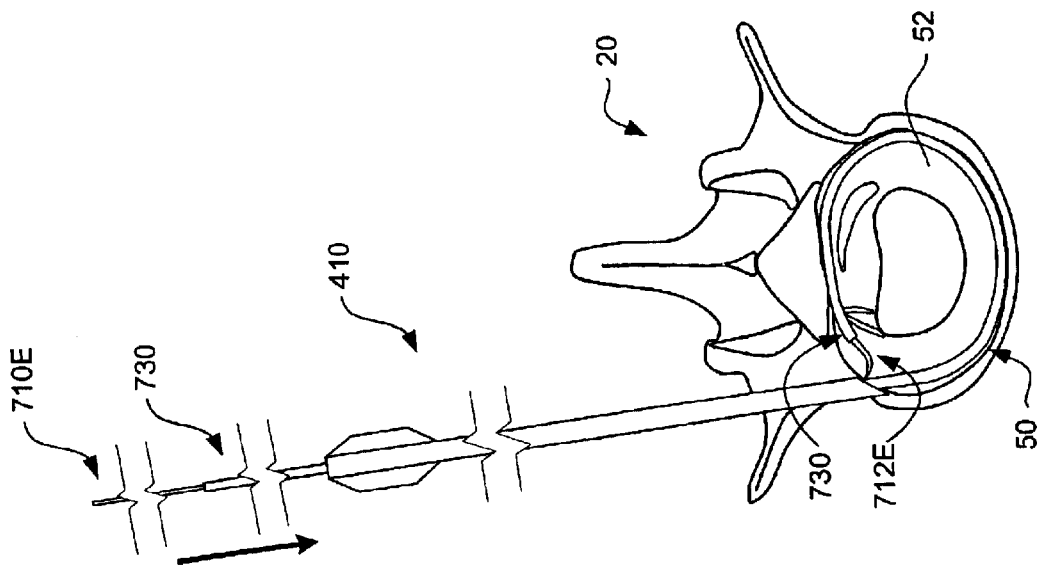

Once the distal end of the stylet 710A and the distal end of the tubular sheath 730 are disposed adjacent the opening to the distal end of the trocar 410, the straight stylet 710A may be exchanged for double curve stylet 710E as shown in FIG. 18E. The distal tip of the stylet 710E is navigated into the distal end of the trocar 410 utilizing the visualization techniques described previously. Once the distal end of the stylet 710 is disposed in the trocar 410, the tubular sheath 730 may be removed. With the distal end of the stylet 710E reentered into the distal end of the trocar 410, the stylet 710E may be freely advanced until the distal portion thereof exits the proximal portion of the trocar 410 as shown in FIG. 18F.

At this point, the trocar 410 may also be removed, but may optionally be left in place, depending on the means employed to connect the ends of the reinforcement member 600. As illustrated in FIG. 18G, one end 602 of the reinforcement member 600 is connected to the proximal end of the stylet 710. This may be accomplished, for example, by threading the reinforcement member through a hole (not shown) in the proximal end of the stylet 710 similar to the threading a sewing needle. Immediately before or immediately after the reinforcement member 600 is attached to the proximal end of the stylet 710, the pledget push rod 740 may be used to push the pledget 750 over the opposite ends of the stylet 710 until the pledget 750 is positioned immediately adjacent the entry and exit points in the annulus 52 as illustrated in FIG. 18G.

Figure 18H:
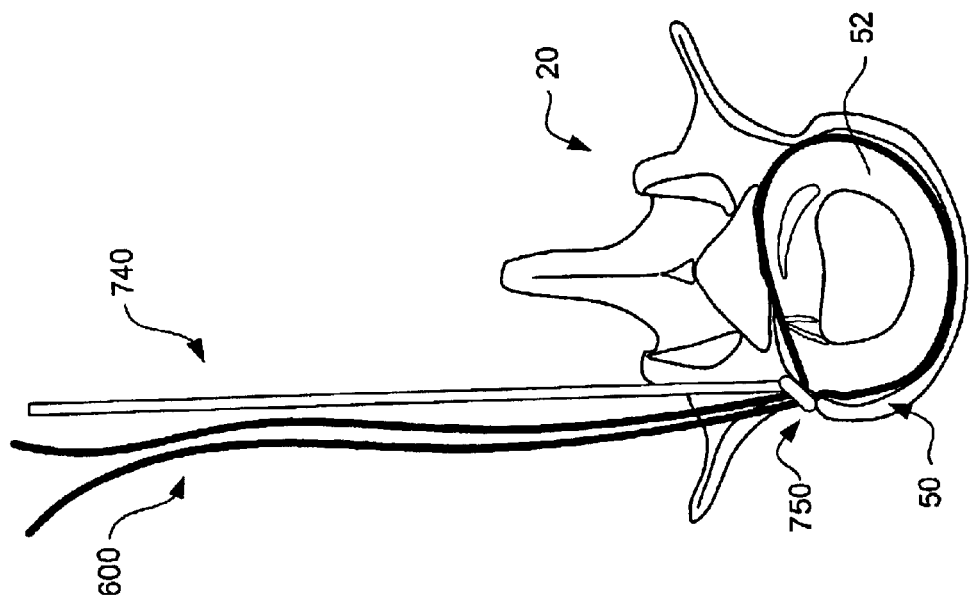
Figure 18G:
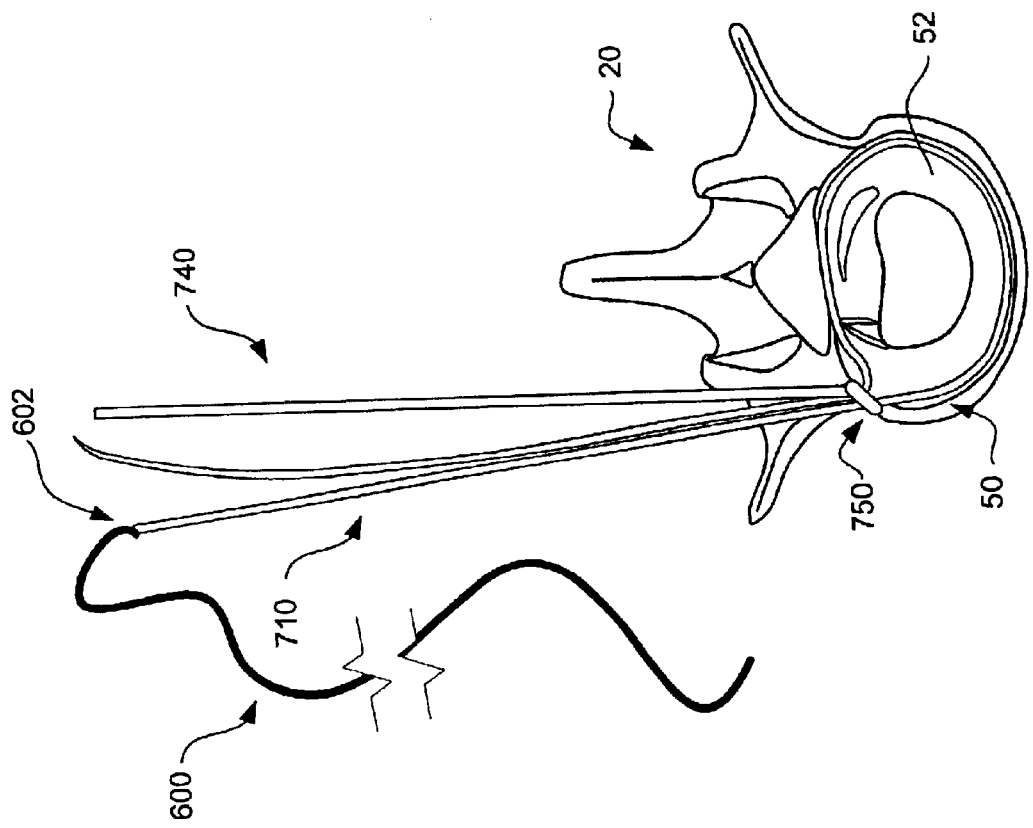

The distal end of the stylet 710 may then be pulled while applying a push force to the push rod 740 to pull the reinforcement member along the path defined the stylet 710 through the annulus 52, after which the reinforcement member 600 may be disconnected from the stylet as shown in FIG. 18H. A connection (e.g., knot) 610 may be made in the reinforcement member 600 and advanced to the pledget 750 utilizing a conventional knot pusher (not shown) as shown in FIG. 18I. While the knot is being tightened, the reinforcement member 600 applies compressive forces about the perimeter of the annulus 52 thereby closing fractures and fissures 56/58. Once the knot 610 has been tightened, the reinforcement member 600 may be cut immediately proximal of the knot 610 adjacent the pledget 750 as shown in FIG. 18J utilizing a conventional suture cutting device (not shown).

Figure 18L:
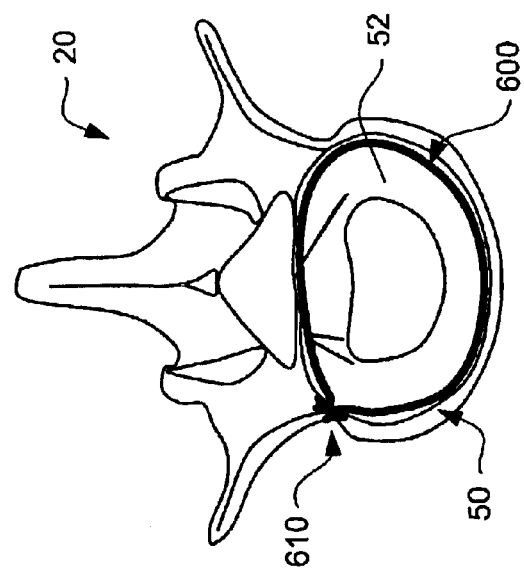
Figure 18K:
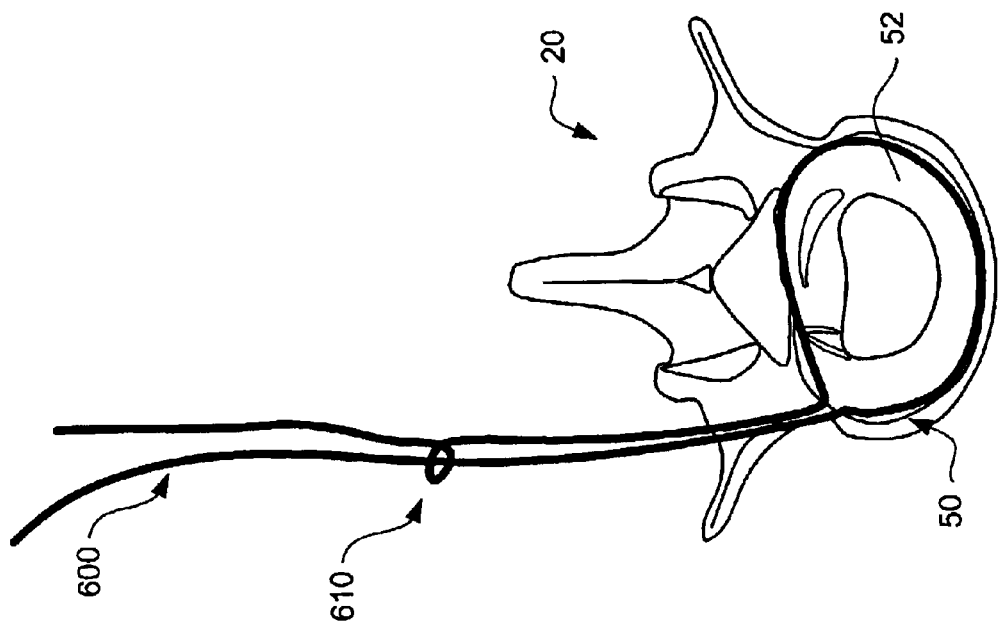

Alternatively, as shown in FIGS. 18K and 18L, the pledget 750 may be omitted. In particular, a connection (e.g., knot) 610 may be made in the reinforcement member 600 and advanced to the entry and exit point in the annulus 52 utilizing a conventional knot pusher (not shown) as shown in FIG. 18K. While the knot is being tightened, the reinforcement member 600 applies compressive forces about the perimeter of the annulus 52 thereby closing fractures and fissures 56/58. Once the knot 610 has been tightened, the reinforcement member may be cut utilizing a conventional suture cutting device (not shown) immediately proximal of the knot 610 as shown in FIG. 18L.

The path navigated through the annulus 52 by the foregoing method may be a function of the individual anatomical geometry of the patient and/or the particular portion of the annulus 52 requiring compression. Accordingly, as shown in FIGS. 19A–19F, the path 620 defined by the stylet 710 and reinforcement member 600 through the annulus 52 may vary. For example, a substantial rectangular path 620A with rounded corners may be employed as illustrated in FIG. 19A. Alternatively, a substantially trapezoidal path 620B having rounded corners may be employed as shown in FIG. 19B. Alternatively, a substantially oval path 620C may be employed as shown in FIG. 19C. Each of these paths may be defined by the particular sequence of curved stylets 710 utilized in accordance with the method described previously.

Although it is preferable to define a path 620 substantially confined to the annulus 52, the path 620 may also extend through a portion of the nucleus 54 as illustrated in FIGS. 19D and 19E. In such circumstances, it is preferable to not define a direct path from the nucleus 54 to the exterior of the annulus 52, to thereby minimize the likelihood that nuclear material will leak out of the disc 50. For example, as shown in FIG. 19D, the path through the nucleus 54 may enter at one lateral side, and exit at the opposite lateral side thereof. Alternatively, as shown in FIG. 19E, the path 620E may enter on the anterior side and exit on the posterior side of the nucleus 54. FIG. 19F illustrates a path 620F which is just external to the outer surface of the annulus 52.

While a single path 620 followed by a single reinforcement member 600 is illustrated, it is also contemplated that multiple reinforcement members 600 may be implanted. For example, one reinforcement member 600 could be implanted proximate the lower (inferior) portion of the annulus 52 and one reinforcement member 600 could be implanted in the upper (superior) portion of the annulus 52. Any number of reinforcement members 600 could be implanted in a single disc, either through a single trocar 410 placement, or multiple trocar placements.

Figure 20B:
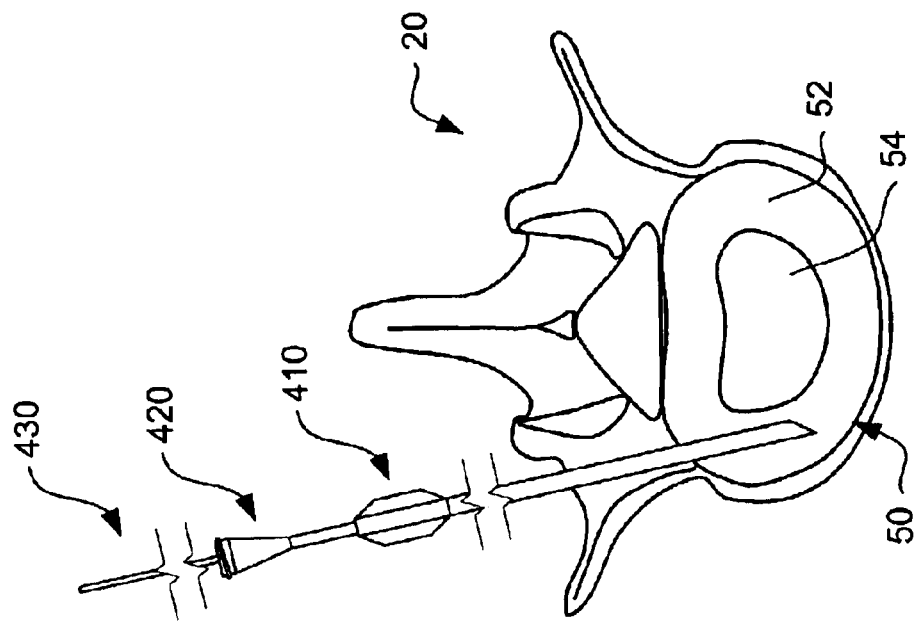
FIGS. 20A–20J illustrate steps for implanting a self-expanding reinforcement member.
Figure 20A:
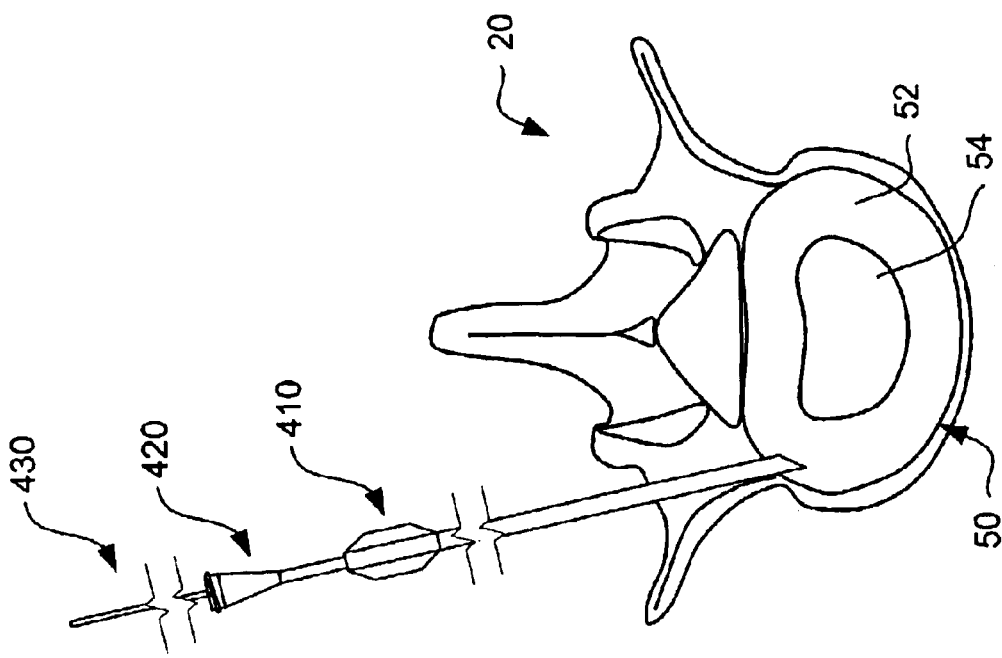
Figure 20D:
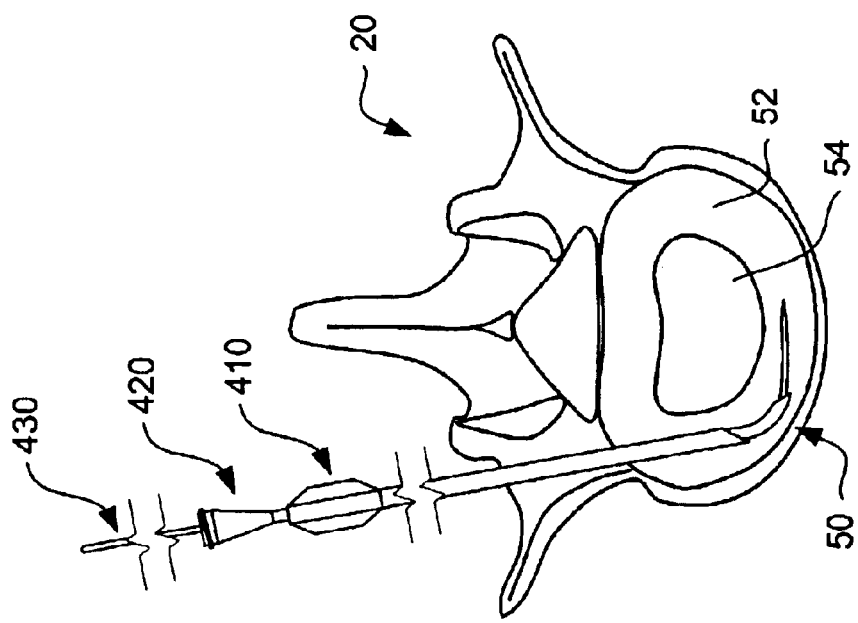
Figure 20C:
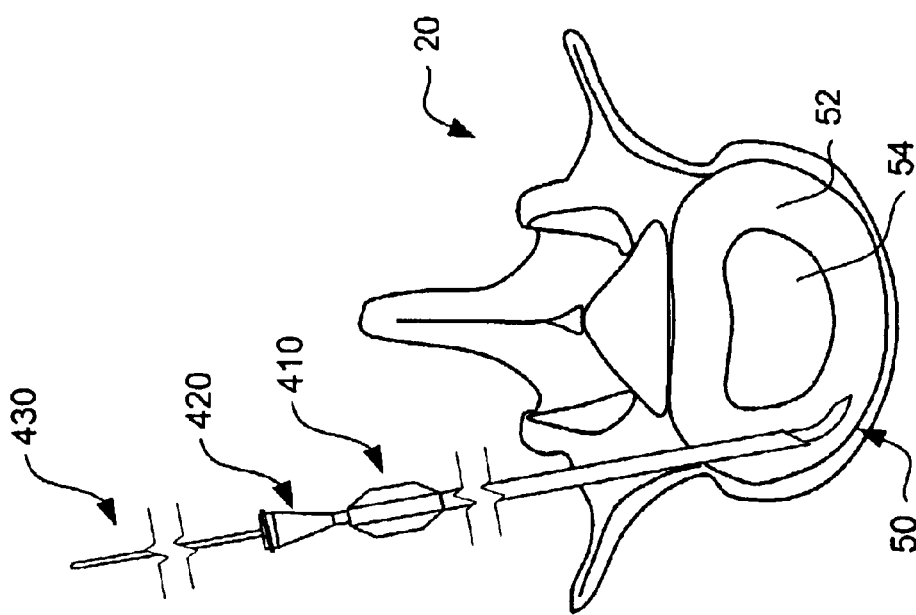
Figure 20F:
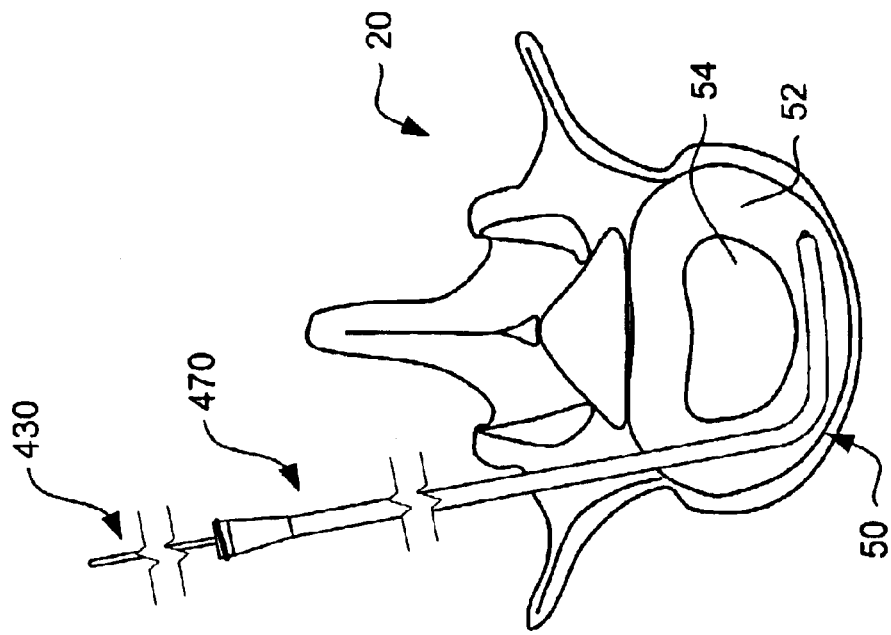
Figure 20E:
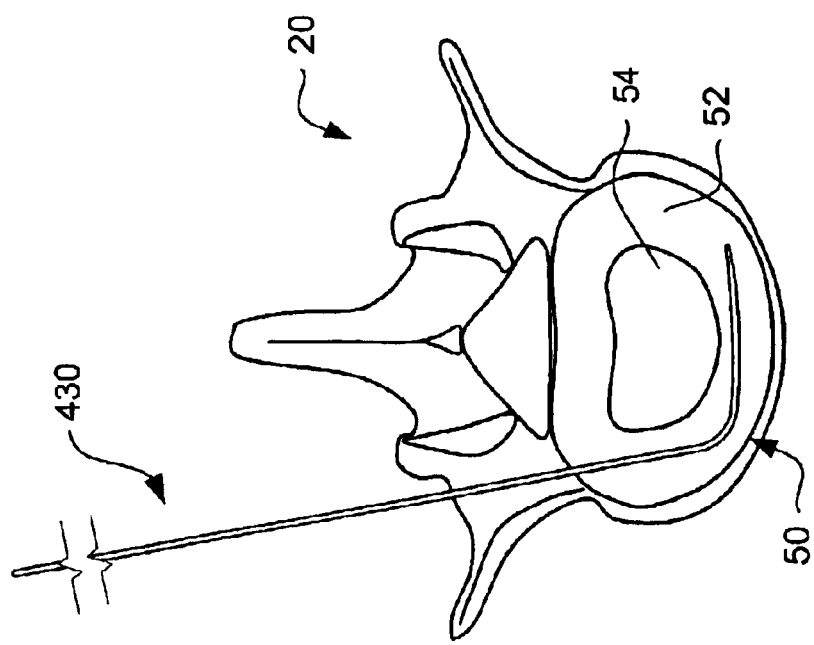
Figure 20H:
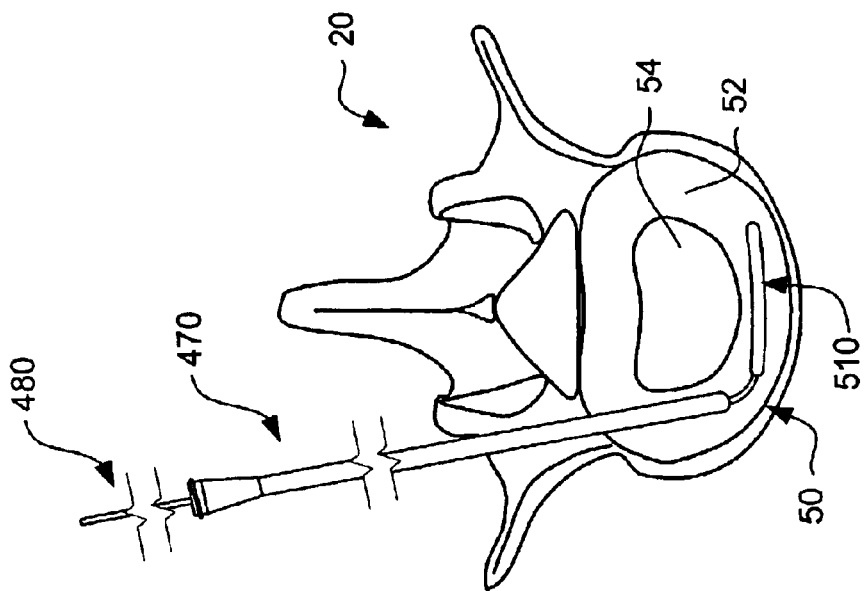
Figure 20G:
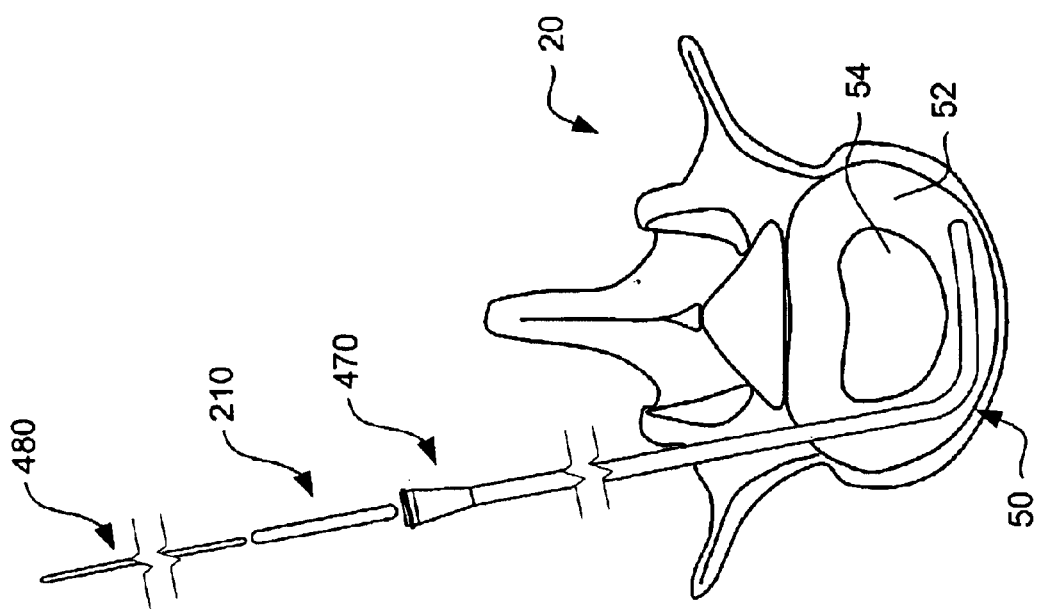
Figure 20J:
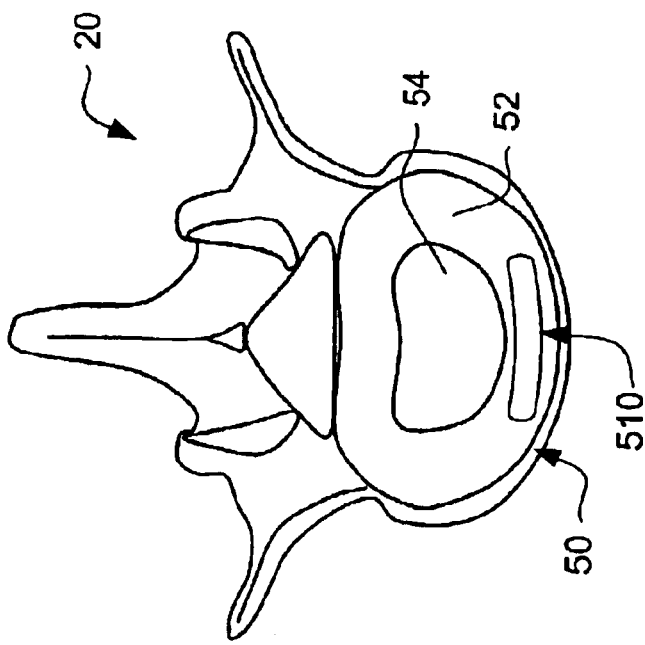
Figure 20I:
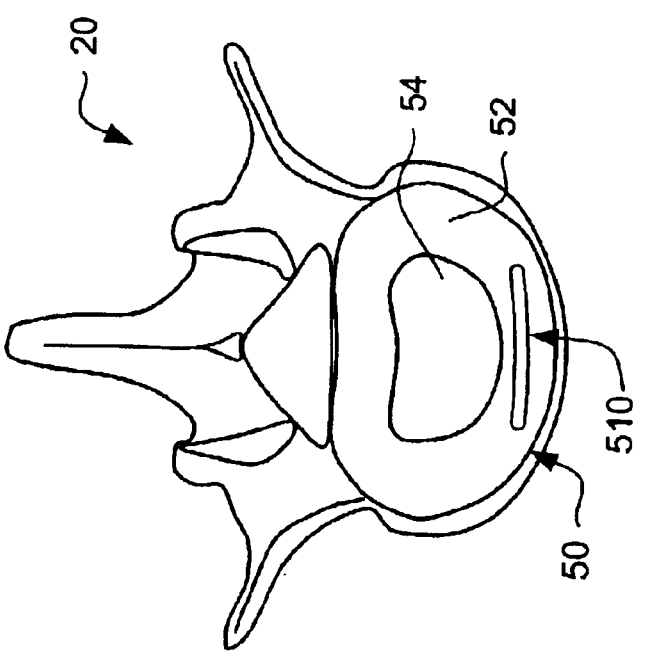
Figure 20K:
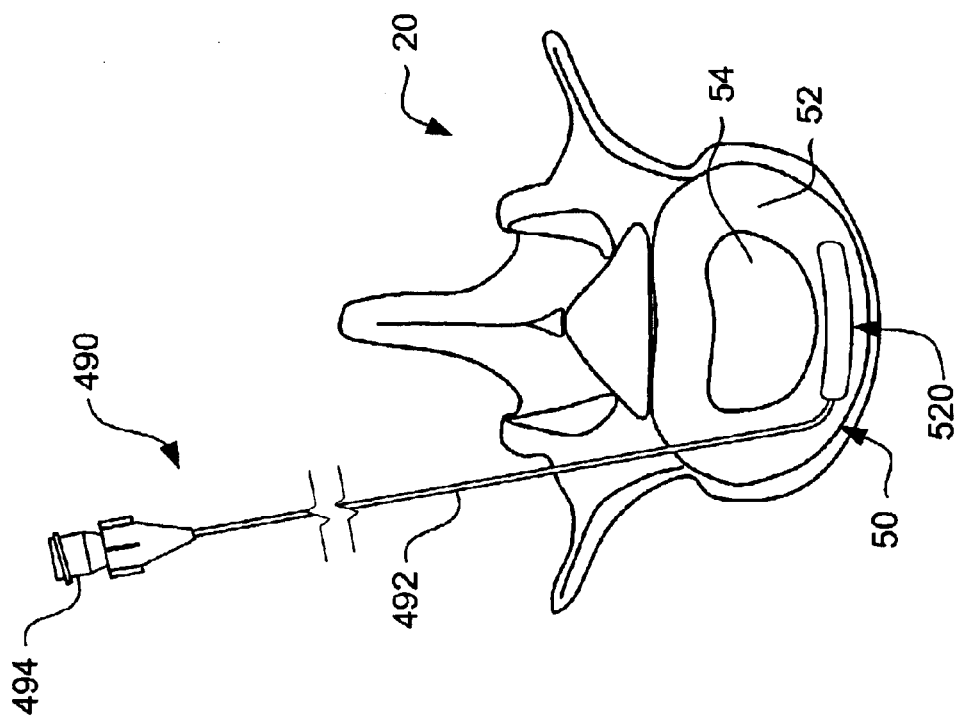
FIGS. 20K–20L illustrate steps for implanting an inflatable reinforcement member.
Figure 20L:
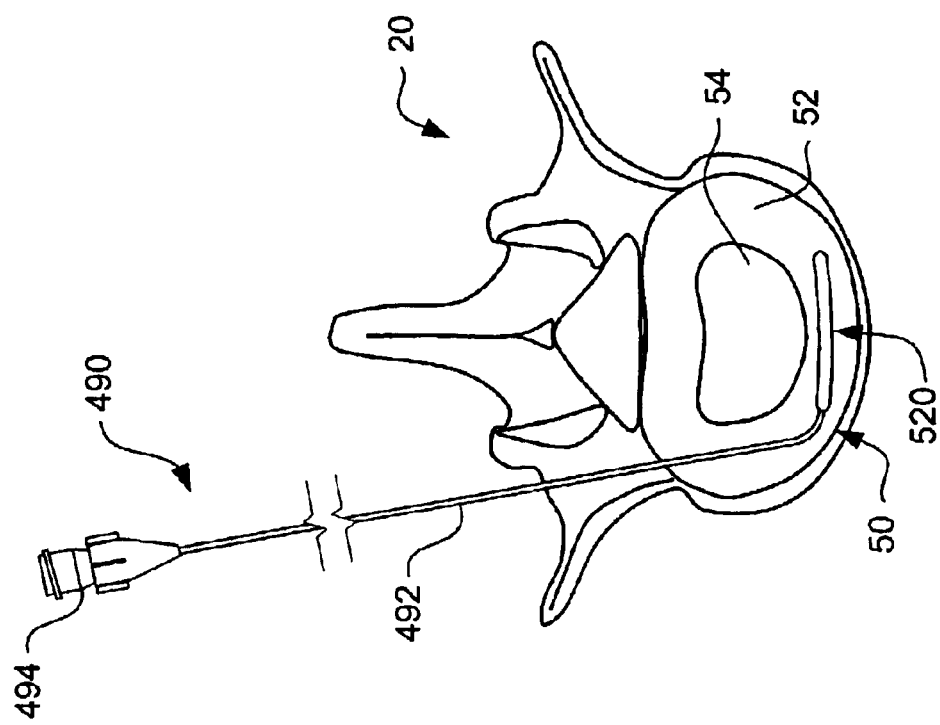
Figure 20N:
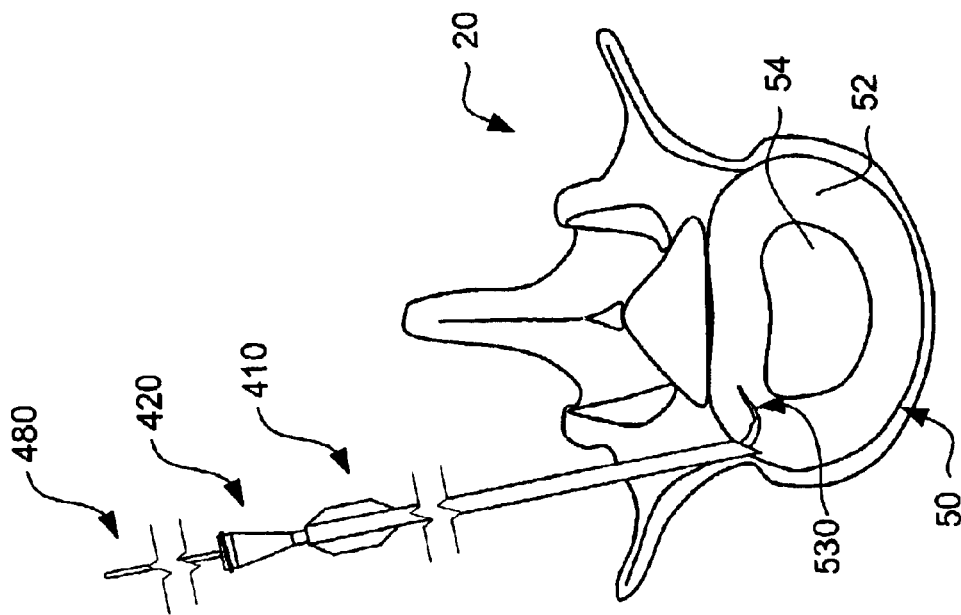
FIGS. 20M–20R illustrate steps for implanting a reinforcement bar.
Figure 20M:
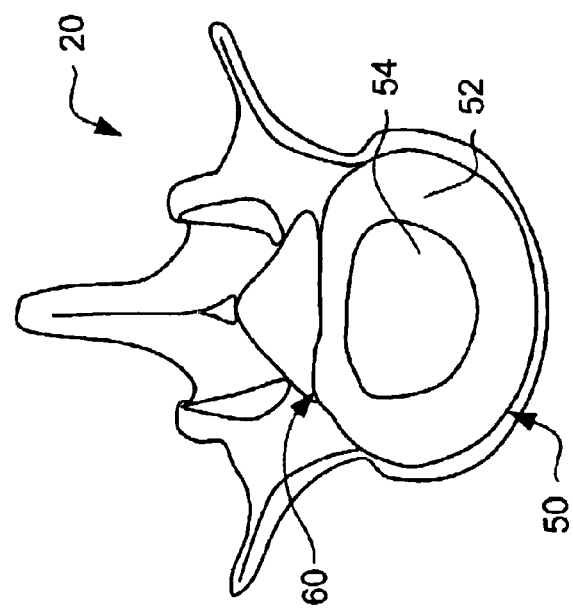
Figure 20P:
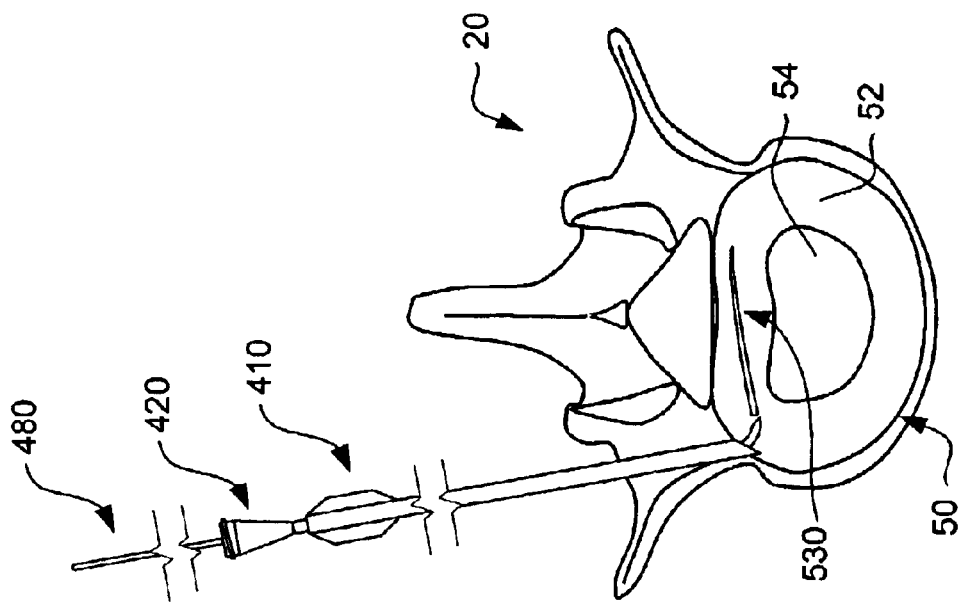
Figure 20O:
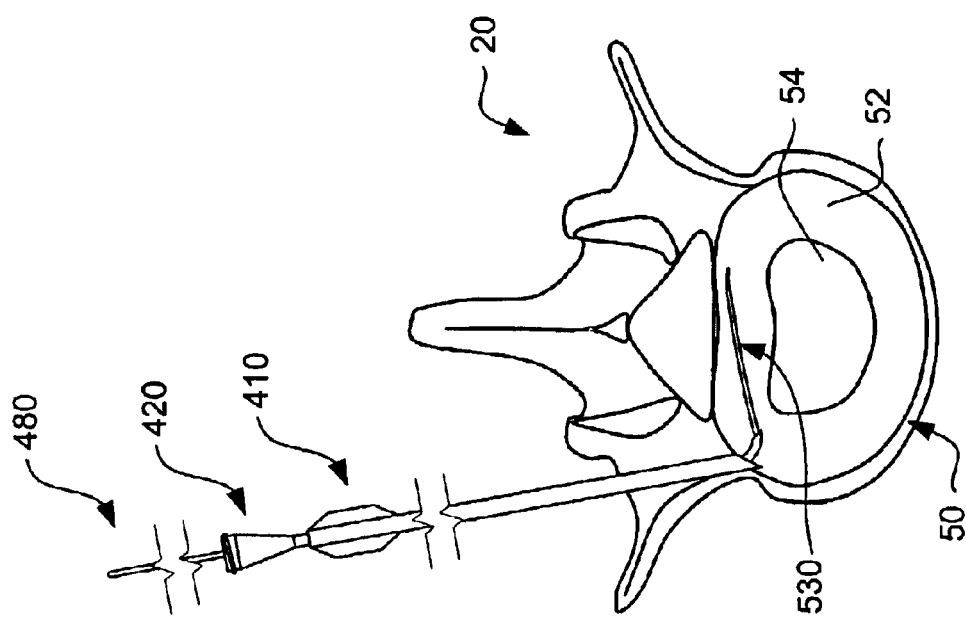
Figure 20R:
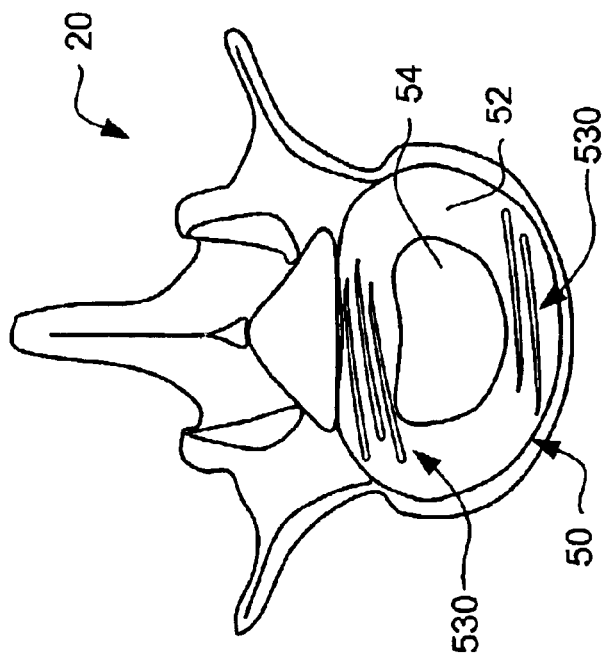

With general reference to FIGS. 20A–20R, alternative embodiments of reinforcement members and methods of implantation are disclosed. The reinforcement members 510/520/530 may be used to reinforce the disc, restore disc height and/or bear some or all of the load normally carried by the annulus. The reinforcement members 510/520/530 are relatively rigid and thus serve to reinforce the disc 50, and particularly the annulus 52, where inserted. In addition, the reinforcement members 510/520/530 may have a relatively large profile when implanted and thus increase disc height.

The reinforcing members 510/520/530 may be used singularly or in groups, depending on the increase in disc 50 height desired and/or the amount of reinforcement of the annulus 52 desired. For example, the reinforcing members 510/520/530 may be stacked or inserted side-by-side. In addition, the reinforcing members 510/520/530 may be located in virtually any portion of the annulus 52. Preferably, the reinforcing members 510/520/530 are substantially symmetrically disposed about the median plane 70 to avoid causing curvature of the spine 10. Although the reinforcing members 510/520/530 may be inserted, in part or in whole, into the nucleus 54, it is preferable to insert them into the annulus 52 for purposes of stability and load carrying. Specifically, to provide stability, it is desirable to symmetrically locate the reinforcing members 510/520/530 as far as reasonably possible from the median plane 70, or to span as great a distance as possible across the median plane 70. In addition, because the annulus 52 of the disc 50 is believed to carry the majority of the load, particularly in the lumbar region 12, the reinforcing members 510/520/530 are preferably placed in the annulus 52 to assume the load normally carried thereby, and reinforce the load bearing capacity of the annulus 52, without hindering the normal mobility function of the disc 50.

The reinforcing members 510/520/530 may comprise expandable members such as self-expanding members 510 or inflatable members 520. Alternatively, the reinforcing members 510/520/530 may comprise unexpandable members such as reinforcement bars 530. When implanting each type of reinforcement member 510/520/530, it is preferable to maintain the integrity of the annulus 52. Accordingly, space in the annulus 52 for the reinforcing members 510/520/530 is preferably established by dilation or the like, although some amount of tissue removal may be used.

The expandable reinforcement members 510/520 are useful because they may be delivered in a low profile, unexpanded condition making it easier to traverse the very tough and fibrous collagen tissue of the annulus 52. For similar reasons, the reinforcement bars 530 are useful because they may have a small diameter and a sharpened tip. Although it is possible to insert the expandable reinforcing members 510/520 into the annulus 52 in their final expanded state, it is desirable to deliver the expandable reinforcing members 510/520 into the annulus 52 in an unexpanded state and subsequently expand them in order to minimize invasiveness and resistance to insertion.

The self-expanding reinforcing member 510 may comprise a solid or semi-solid member that self-expands (e.g., by hydration) after insertion into the annulus. Examples of suitable materials for such solid or semi-solid members include solid fibrous collagen or other suitable hard hydrophilic biocompatible material. If the selected material is degradable, the material may induce the formation of fibrous scar tissue which is favorable. If non-degradable material is selected, the material must be rigid and bio-inert. The self-expanding reinforcing member 510 preferably has an initial diameter that is minimized, but may be in the range of 25% to 75% of the final expanded diameter, which may be in the range of 0.3 to 0.75 cm, or 10% to 75% of the nominal disc height. The length of the self-expanding member 510 may be in the range of 1.0 to 6.0 cm, and preferably in the range of 2.0 to 4.0 cm.

The inflatable reinforcing member 520 may comprise an expandable hollow membrane capable of inflation after insertion into the annulus. An example of a suitable inflatable structure is detachable balloon membrane filled with a curable material. The membrane may consist of a biocompatible and bio-inert polymer material, such as polyurethane, silicone, or polycarbonate-polyurethane (e.g., Corethane). The curable filler material may consist of a curable silicone or polyurethane. The filler material may be curable by chemical reaction (e.g., moisture), photo-activation (e.g., UV light) or the like. The cure time is preferably sufficiently long to enable activation just prior to insertion (i.e., outside the body) and permit sufficient time for navigation and positioning of the member 520 in the disc. However, activation may also take place inside the body after implantation. The inflatable reinforcing member 520 preferably has an initial deflated diameter that is minimized, but may be in the range of 25% to 75% of the final inflated diameter, which may be in the range of 0.3 to 0.75 cm, or 10% to 75% of the nominal disc height. The length of the inflatable member 520 may be in the range of 1.0 to 6.0 cm, and preferably in the range of 2.0 to 4.0 cm.

The reinforcement bars 530 may comprise a rigid, solid or hollow bar having a sharpened tip. The reinforcement bars 530 may comprises stainless steel mandrels, for example, having a diameter in the range of 0.005 to 0.100 inches, preferably in the range of 0.010 to 0.050 inches, and most preferably in the range of 0.020 to 0.040 inches, and a length in the range of 1.0 to 6.0 cm, and preferably in the range of 2.0 to 4.0 cm. The reinforcement bars 530 may be straight for linear insertion, or curved to gently wrap with the curvature of the annulus during insertion. In addition, the outer surface of the reinforcement bars 530 may have circular ridges or the like that the permit easy insertion into the annulus 52 but resist withdrawal and motion in the annulus following implantation. Other suitable materials for reinforcement bars 530 include titanium alloy 6-4, MP35N alloy, or super-elastic nickel-titanium alloy.

With general reference to FIGS. 20A–20J, the steps for implanting a self-expanding reinforcement member 510 are illustrated. It should be understood that the procedure for implanting a single member 510 in the anterior annulus 52 is shown for purposes of illustration, not limitation. All of the variables with regard to quantity, location, orientation, etc. discussed previously may be implemented by varying the generic procedure described hereinafter.

Initially, the sharpened stylet 430, semi-rigid needle 420 and rigid trocar 410 are assembled. As shown in FIG. 20A, the distal portion of the assembly 410/420/430 is inserted into the disc 50 as in a conventional discogram procedure. The assembly 410/420/430 is advanced until the distal tip 413 of the rigid needle is proximate the anterior curvature of the annulus 52, near the anterior side of the nucleus 54, as seen in FIG. 20B. The semi-rigid needle 420 (alone or with stylet 430) is advanced relative to the rigid trocar 410 until the curved portion 426 of the semi-rigid needle exits the distal tip 413 of the rigid trocar 410 and the desired amount of curvature is established, as seen in FIG. 20C. The curved portion 426 may be advanced until the tip 423 is substantially parallel to the tangent of the anterior annulus 52 curvature. The sharpened stylet 430 is advanced relative to the semi-rigid needle 420 to the desired position within the anterior annulus 52, as shown in FIG. 20D. The semi-rigid needle 420 and the rigid trocar 410 are completely withdrawn from the stylet 430, leaving the stylet in position as shown in FIG. 20E.

A flexible dilator 470 is advanced over the stylet 430 to dilate the annulus 52, as seen in FIG. 20F. The flexible dilator 470 is similar to semi-rigid needle 420 except that the dilator includes a blunt distal tip and is relatively more flexible, and has larger inner and outer diameters. Note that one or more dilators 470 may be advanced co-axially about the stylet 430 until the annulus is sufficiently dilated to accept the self-expandable member 510. The stylet 430 is then withdrawn from the flexible dilator 470 and the self-expandable member 510 is introduced into the lumen of the flexible dilator 470 using a push bar 480, as shown in FIG. 20G. Alternatively, the dilator 470 may be removed in favor of a flexible hollow catheter with a large inner diameter to facilitate delivery of member 510. The push bar 480 is similar to stylet 430 except that the distal tip of the push bar 480 is blunt. Alternatively, the push bar 480 may simply comprise the stylet 430 turned around, thus using the proximal blunt end of the stylet 430 as the push bar 480. The push bar 480 is advanced until the member 510 is in the desired position, as seen in FIG. 20H. To facilitate positioning the member 510, radiographic visualization may be used to visualize the distal end of the push bar 480, which is formed of radiopaque material and may include radiopaque markers. In addition, the member may be loaded with a radiopaque material to facilitate radiographic visualization thereof.

After the member 510 is in the desired position, the flexible dilator 470 is retracted from the push bar 480 while maintaining position of the member 510 with the push bar. The push bar 480 is then removed leaving the member 510 in place. If necessary, the procedure may be repeated for additional member implants 510. The member 510 is then allowed to expand over time, perhaps augmented by placing the spine 10 in traction. Alternatively, the spine 10 may be placed in traction prior to beginning the procedure.

With reference to FIGS. 20K–20L, the steps for implanting an inflatable reinforcement member 520 are illustrated. In this procedure, the steps outlined with reference to FIGS. 20A–20F are followed. Specifically, the same steps are followed up to and including the step of advancing the flexible dilator 470 over the stylet 430 to dilate the annulus 52, and thereafter removing the stylet 430 from the flexible dilator 470. Using a catheter 490, the inflatable member 520 is introduced into the dilator 470 and advanced until the member 520 is in the desired position, as shown in FIG. 20K. The inflatable member 520 is connected to the distal end of the catheter 490, which includes a flexible but pushable shaft 492 and an inflation port 494. The flexible dilator 470 is retracted from the catheter 490 while maintaining position of the member 520.

With the member 520 in the desired position, which may be confirmed using radiographic visualization as described above, the proximal inflation port 494 is connected to a syringe (not shown) or other suitable inflation apparatus for injection of the curable filler material. The filler material is then activated and the desired volume is injected into the catheter 490 via the inflation port 494, as seen if FIG. 20L. The filler material is allowed to cure and the catheter 490 is gently torqued to break the catheter 490 from the solid member 520. This break-away step may be facilitated by an area of weakness at the juncture between the distal end of the catheter 490 and the proximal end of the member 520. The catheter 490 is then removed leaving the member 520 in place. If necessary, the procedure may be repeated for additional member implants 520.

With reference to FIGS. 20M–20R, the steps for implanting a reinforcement bar 530 are illustrated. As seen in FIG. 20M, the disc 50 includes a protrusion or bulge 60, which is preferably, but not necessarily, reduced or eliminated before insertion of the reinforcement bar 530. This may be done by separating the adjacent vertebrae 20. In order to establish separation of the vertebrae 20, the spine 10 may be placed in traction or conventional intervertebral separation tools may be used. After the bulge 60 is reduced or eliminated, similar steps are followed as outlined with reference to FIGS. 20A–20C.

Delivery of a single reinforcement bar 530 into the posterior annulus 52 is illustrated. Specifically, the distal portion of the assembly 410/420/480 is inserted into the disc 50 as in a conventional discogram procedure. The assembly 410/420/480 is advanced until the distal tip 413 of the rigid trocar 410 just penetrates the posterior side of the annulus 52, as seen in FIG. 20N. The semi-rigid needle 420 (alone or with bar 530) is advanced relative to the rigid trocar 410 until the curved portion 426 of the semi-rigid needle 420 exits the distal tip 413 of the rigid trocar 410 and the desired amount of curvature is established, as shown in FIG. 20N. The curved portion 426 may be advanced until the tip 423 is substantially parallel to the posterior annulus 52.

Figure 20Q:
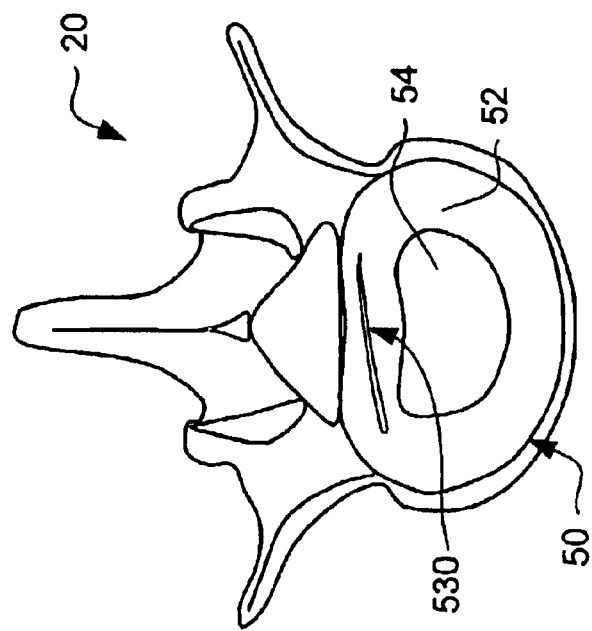

Using the push bar 480, the reinforcement bar 530 with its sharpened tip is pushed into the annulus 52 as seen in FIG. 20O. The reinforcement bar 530 is advanced into the annulus 52 with the push bar 480 until the bar 530 is in the desired position, as seen in FIG. 20P, which may be confirmed using radiographic visualization as described above. The push bar 480 is then retracted, leaving the reinforcement bar 530 in place, as shown in FIG. 20P. The semi-rigid needle 420 and the rigid trocar 410 are then removed, as shown in FIG. 20Q, or, if necessary, the procedure may be repeated for additional reinforcement bar implants 530, as shown in FIG. 20R. Presence of the reinforcement bars 530 serves to keep the disc 50, and particularly the bulge 60, in a more normal condition, and to protect against continued bulging, thus easing nerve impingement.

With reference to FIGS. 21A–21C, an alternative reinforcement member 540 is illustrated. In this embodiment, reinforcement member 540 includes an anchor arm 542 having an anchor mechanism 544 attached to a distal end thereof. The anchor mechanism 54 may comprise circular ridges, barbs or the like which are readily advanced into the annular tissue 52, but resist retraction. Reinforcement member 540 also includes a lever arm 546 including a distal sharpened tip 548. The distal end of the anchor arm 542 also incorporates a sharpened tip 548. The reinforcement member 540 preferably comprises a highly elastic or super-elastic metal such as stainless steel or a nickel titanium alloy.

FIG. 21A illustrates the reinforcement member in a relaxed state, and FIG. 21B illustrates the reinforcement member in a compressed delivery state sized to fit within trocar 410. The reinforcement member 540 may be delivered into the annulus 52 in a compressed state through trocar 410 utilizing push rod 480 as shown in FIG. 21C. As the reinforcement member 540 is pushed out the distal end of the trocar 410 utilizing push rod 480, the sharpened ends 548 penetrate the tissue and the anchor mechanism 544 engages the tissue to define the deployed configuration shown in FIG. 21C. In the deployed configuration, the anchor arm and the lever arm are forced to pivot relative to each other thereby building a bias force at the elbow connecting the anchor arm 542 and the lever arm 546. In the deployed configuration, the lever arm 546 applies a compressive force to the exterior portion of the annulus 52 to minimize protrusions and bulges along the posterior periphery of the annulus 52.

With reference now to FIGS. 22A–22D, alternative reinforcement members 570 and 580 are illustrated. Reinforcement members 570 and 580 are similar to reinforcement 600 except for the provision of distal anchors 574/584. Except as described herein and apparent from the drawings, the function and delivery of reinforcement members 570 and 580 are substantially the same as reinforcement member 600.

Figure 22A:
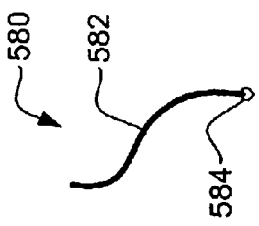
FIGS. 22A–22D illustrate a reinforcement member in accordance with yet another alternative embodiment of the present invention.

As shown in FIG. 22A, reinforcement member 570 comprises a monofilament or multifilament structure 572 that is highly flexible and has a high tensile strength. The ends of the filament structure 572 incorporate anchors 574, which may comprise circular ridges, barbs or the like which are readily advanced into the annular tissue 52, but resist retraction. As shown in FIG. 22B, the reinforcement member 570 may be deployed in the annulus 52 with the anchors residing in healthy annular tissue and the filament structure partially surrounding the fractures and fissures 56/58 in a circumferential manner. By advancing the anchors 574 during deployment, the annular tissue 52 is compressed along the length of the filament structure 572, thereby closing fractures and fissures 56/58 and reducing posterior protrusions.

Figure 22C:
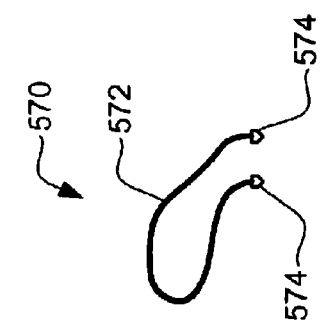
Figure 22B:
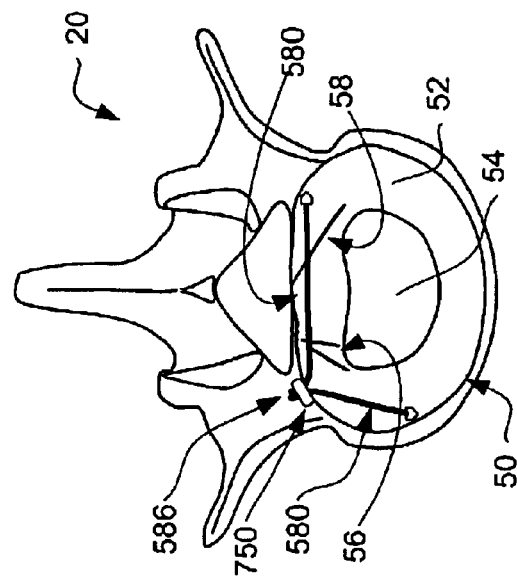
Figure 22D:
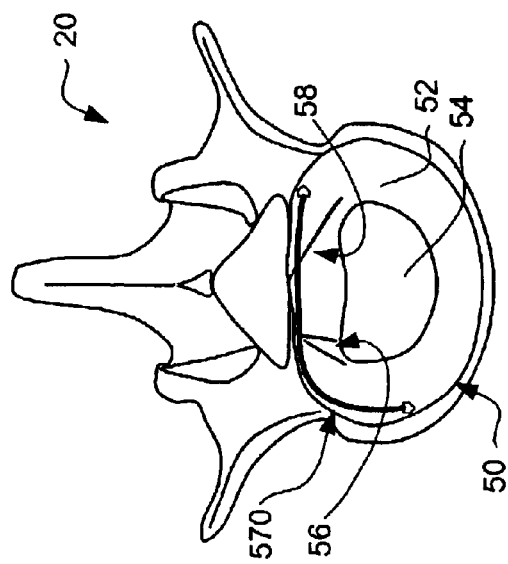

A similar arrangement is shown in FIGS. 22C and 22D. In this embodiment, a reinforcement member 580 comprises a monofilament or a multifilament structure 582 having a single distal anchor 584 attached thereto. The proximal end of the filament structure 582 is otherwise free. During implantation, one or more reinforcement members 580 may be utilized as shown in FIG. 22D. The free ends of the filament structure 582 are connected using, for example, a knot 586 with or without the use of a pledget 750.

Figure 23B:
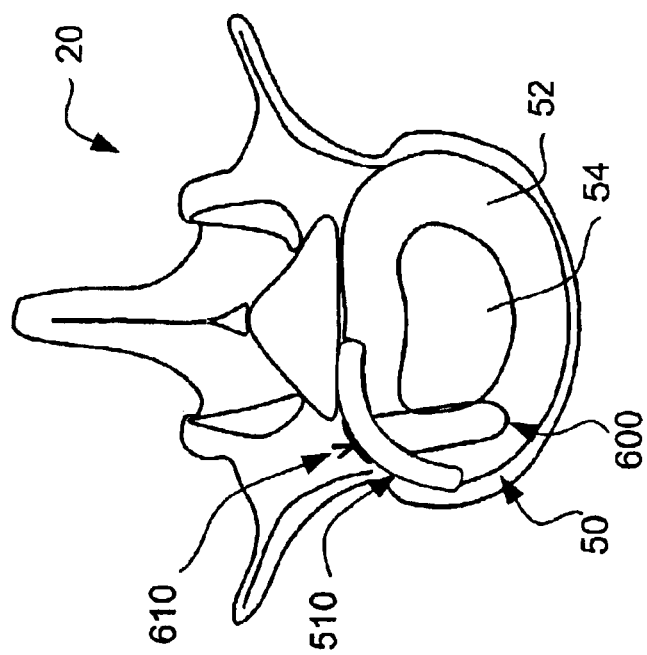
FIGS. 23A and 23B illustrate an alternative method for implanting a variation of the reinforcement member shown in FIG. 20J in accordance with an embodiment of the present invention.
Figure 23A:
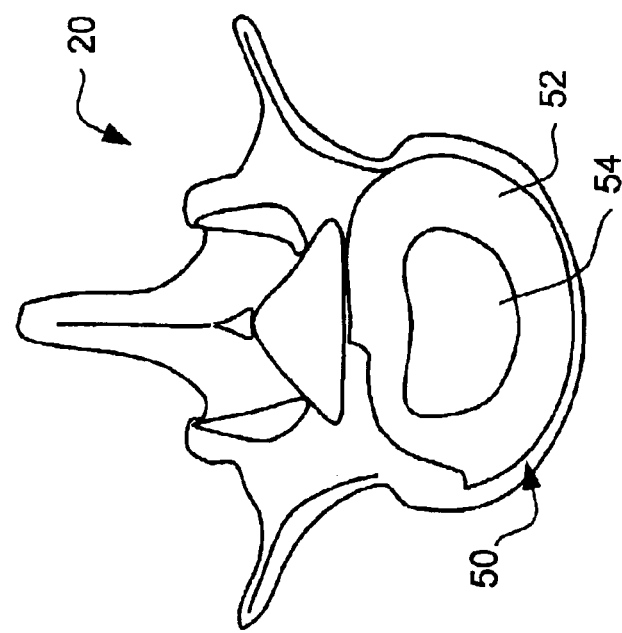

Refer now to FIGS. 23A and 23B which illustrate an alternative method for implanting a variation of the reinforcement member 510, and optionally utilize another reinforcement member 600 to anchor reinforcement member 510 in place. Reinforcement member 510 may be implanted in a void left by discectomy utilizing a method such as described with reference to FIGS. 20A–20L. Other reinforcement members may used in place of reinforcement member 510 such as reinforcement members 100/200. Other reinforcement members may optionally be used as anchor means. By way of example, not limitation, reinforcement member 600 is shown as a means to anchor reinforcement member 510 relative to the annulus 52 utilizing a method such as described with reference to FIGS. 25A–25J or FIGS. 27A–27H, for example.

Following a discectomy, a portion of the annulus 52 is typically removed as shown in FIG. 23A. The void left by the discectomy procedure may expose the disc 50 to increased stress due to loss of surface area and/or leakage of fluid from the nucleus 54. By implanting a reinforcement member 510 in the void as seen in FIG. 23B, the reinforcement member 510 acts as a barrier to nuclear leakage and acts as a support member to minimize disc height loss. Reinforcement member 510 acts as a support to adjacent vertebrae by having a height substantially equal to the nominal height of the disc (in a healthy state) and by providing an expanded volume substantially equal to the void, to thereby share the load of adjacent vertebrae. This combination of functions (barrier and volume) reduces the rate of degeneration or possibly eliminates further degeneration of the disc 50.

Figure 24E:
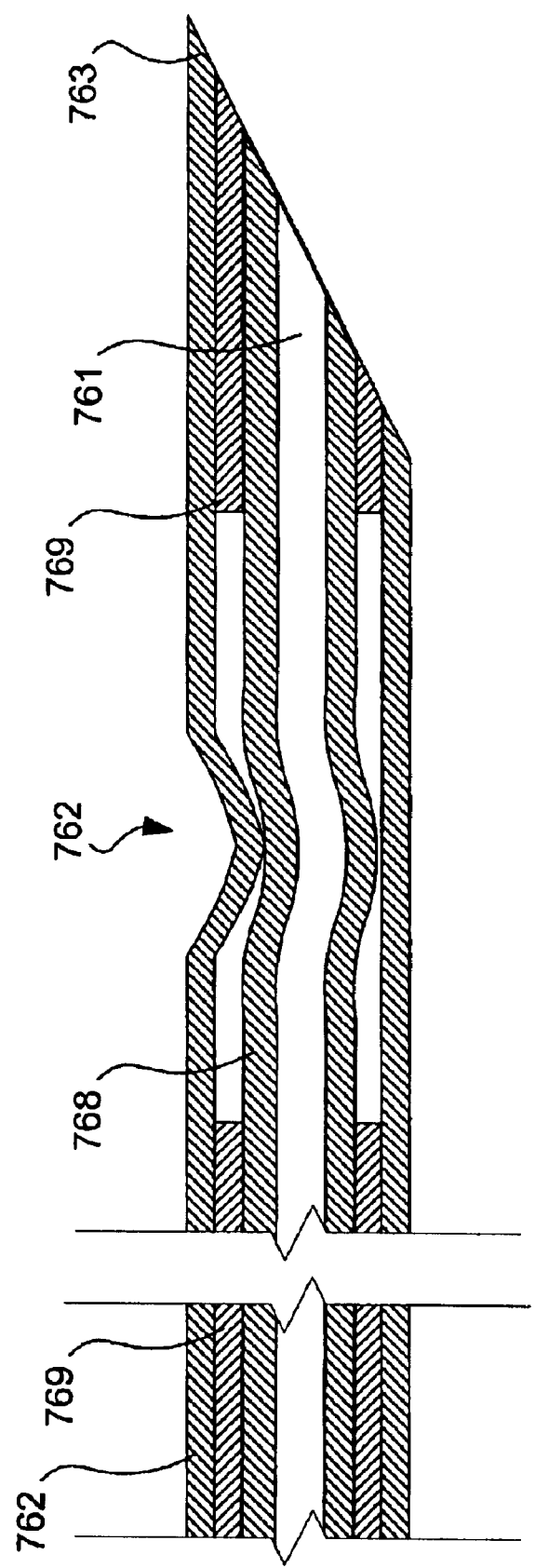

Refer now to FIGS. 24A–24E which illustrate various tools 760/770 for implanting the reinforcement member 600 in accordance with the method illustrated in FIGS. 25A–25J. As seen in FIG. 24A, dual tube trocar 760 includes two rigid tubes 762 formed of stainless steel, for example, secured to a handle 764. The tubes 762 may be substantially the same size and symmetric. Each tube 762 includes a sharpened tip 763 and a lumen (not visible) fully extending therethrough to slidably accommodate stylet 770 shown in FIG. 24B. The lumen of the second tube 762 which accommodates reentry of the stylet 770 may be made even larger (e.g., 2–3 times) to permit variability in reentry as will be discussed in more detail hereinafter. A bracket 766 may be disposed between the rigid tubes 762 to maintain spacing and alignment therebetween.

With reference to FIG. 24B, stylet 770 is substantially the same as stylet 710 described previously. Stylet 770 includes an elongate flexible shaft 772 and a sharpened distal end 773. The stylet or needle 770 has a curved portion 774 with a diameter substantially equal to the distance between the centerlines of the tubes 762 of the trocar 760. The curved portion 774 preferably has at least 180 degrees of curvature or more to define at least a full semi-circle. The shaft 772 of the stylet 770 preferably has a flexible but pushable construction incorporating a rigid metal mandrel such as stainless steel, or a super-elastic alloy such as nickel-titanium. Highly elastic or super-elastic materials incorporated into the elongate shaft 772 resist permanent deformation during insertion and navigation through the annulus 52. The shaft 772 of the stylet 770 may have a diameter ranging from 0.010 to 0.025 inches and is sized to fit within the lumens of the tubes 762 of the trocar 760. The shaft 772 may be coated with a lubricious material such as PTFE and a hydrophilic polymer.

If the tip 773 is sufficiently sharp to easily penetrate annular tissue 52, the path through the annular tissue 52 taken by the stylet 770 will substantially conform to the geometry of the distal curved portion 774 of the stylet 770. In particular, if the distal portion 774 has a curve with a diameter substantially equal to the distance between the centerlines of the tubes 762 of the trocar 760, the stylet 770 will exit the distal end of one tube 762 and naturally define a path through the annular tissue 52 to reenter the distal end of the other tube 762. To this end, it is desirable to provide a tip 773 having sufficient sharpness to readily penetrate annular tissue 52, which tends to be relatively fibrous and tough. By providing a sufficiently sharp tip 773, the stylet 770 will naturally navigate through the annulus 52 from the end of one tube 762 into the end of the other tube 762, without requiring visualization or steering of the stylet 770.

Refer now to FIGS. 24C and 24D which illustrate alternative dual tube trocar 760 designs which utilizes means 765/767 to ensure proper alignment of the stylet 700 as it exits the distal end of one of the tubes 762. In particular, in order for the stylet 770 to reenter the distal end of the second tube 762, the stylet 770 preferably exits the distal end of the first tube 762 with the curved portion 774 of the stylet 770 in substantially the same plane as the two tubes 762. This may be accomplished manually by rotating the stylet 770 prior to exit from the first tube 762, or this may be accomplished automatically by providing a keyed passageway or by providing mechanisms 765/767.

Because the curved portion 774 will align itself with any curvature provided in the lumen of the tubes 762, the distal end of one or both of the tubes 762 may be provided with a gentle curvature 765 as seen in FIG. 24C which will provide a corresponding curvature to the lumen extending therethrough. Alternatively, the distal end of one of the tubes 762 may be provided with an indentation 767 as seen in FIG. 24D which will define a corresponding curved path in the lumen extending therethrough. In particular, with reference to FIG. 24E, the indent 767 impinges on an inner tube 768 which is otherwise centered in the lumen of the tube 762 by collars 769. By virtue of the indent 762, the lumen 761 defined through the inner tube 768 is provided with a curved path. Whether provided by a curve in the tube 762, by an indent 762 impinging on an inner tube 768, or by other means to define a curved path within the tube 762, the curved portion 774 of the stylet will naturally align itself with such a curvature, thereby automatically providing alignment between the stylet 770 and the second tube 762 as the distal end of the stylet 770 reenters the trocar 760 as will be described in more detail hereinafter.

Refer now to FIGS. 25A–25J which illustrate an alternative method for implanting the reinforcement member 600. The method illustrated in FIGS. 25A–25J utilizes stylet 770 to navigate through the annulus 52 and implant reinforcement member 600. The method illustrated in FIGS. 25A–25J is similar to the method illustrated in FIGS. 18A–18L, except with regard to path defined by reinforcement member 600 and the automatic navigation of stylet 770 out of and into the trocar 760. The method illustrated in FIGS. 25A–25J is particularly suited for a post discectomy procedure to close the opening (not shown) created thereby. Further, the method illustrated in FIGS. 25A–25J is particularly suited for a post annular compression procedure (e.g., contraction of annular tissue by thermal means) to maintain the re-compressed annulus (not shown) created thereby. All of the variables with regard to quantity, location, orientation, etc., discussed previously may be implemented by varying the generic procedure described hereinafter. The method illustrated in FIGS. 25A–25J is a percutaneous procedure in which access to the disc 50 is achieved utilizing a number of small diameter tools which may be inserted through a patient's back (skin and back muscles), between adjacent vertebrae, and adjacent the patient's disc 50.

Figure 25B:
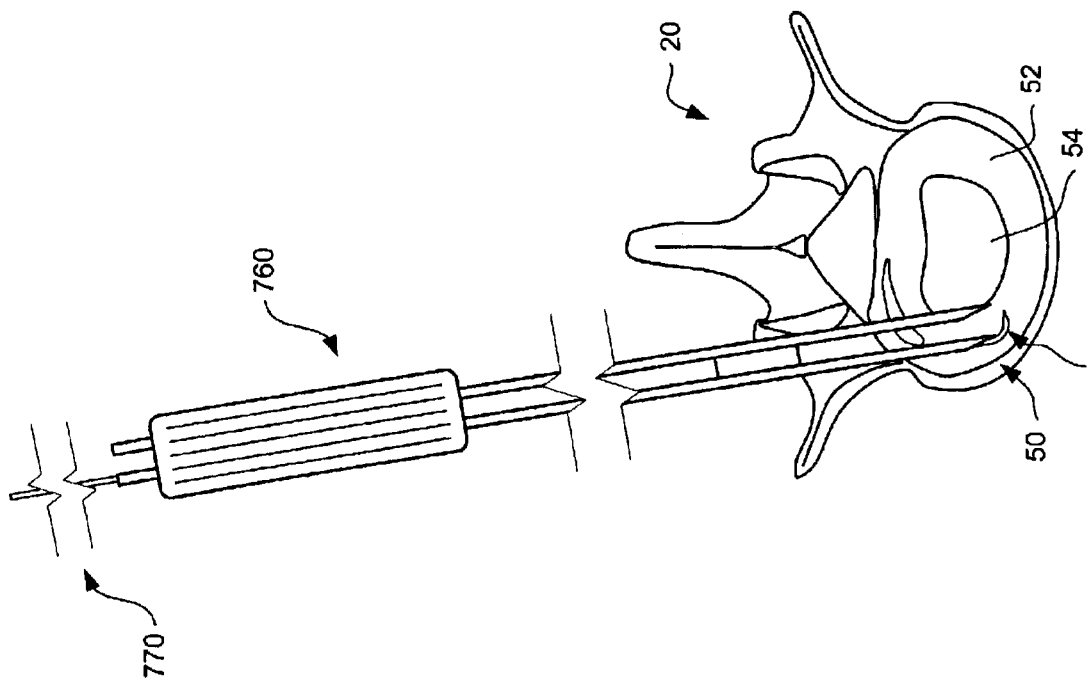
Figure 25A:
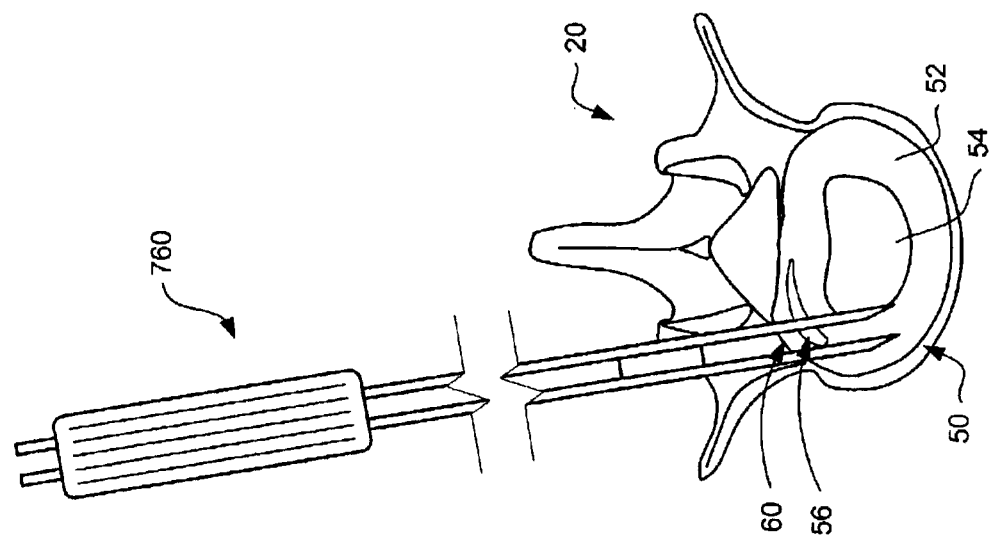

Initially, as shown in FIG. 25A, the rigid dual tube trocar 760 is advanced until the distal tips thereof are disposed in the anterior portion of the annulus 52. The stylet 770 is then inserted into the first tube 762 of the rigid dual tube trocar 760. The stylet 770, having a curved distal portion 774, is advanced out the distal end of the fist tube 762 into the annulus 52 as shown in FIG. 25B. The stylet 770 is advanced until the distal tip 773 reenters the trocar 760 at the distal end of the second tube 762 as shown in FIG. 25C. Note that the curvature 774 corresponds to the distance between the centerlines of the tubes 762, and that the curvature 774 is at least semi-circular (180 degrees or more) to thereby automatically reenter the trocar 760 at the distal end of the second tube 762.

Figure 25H:
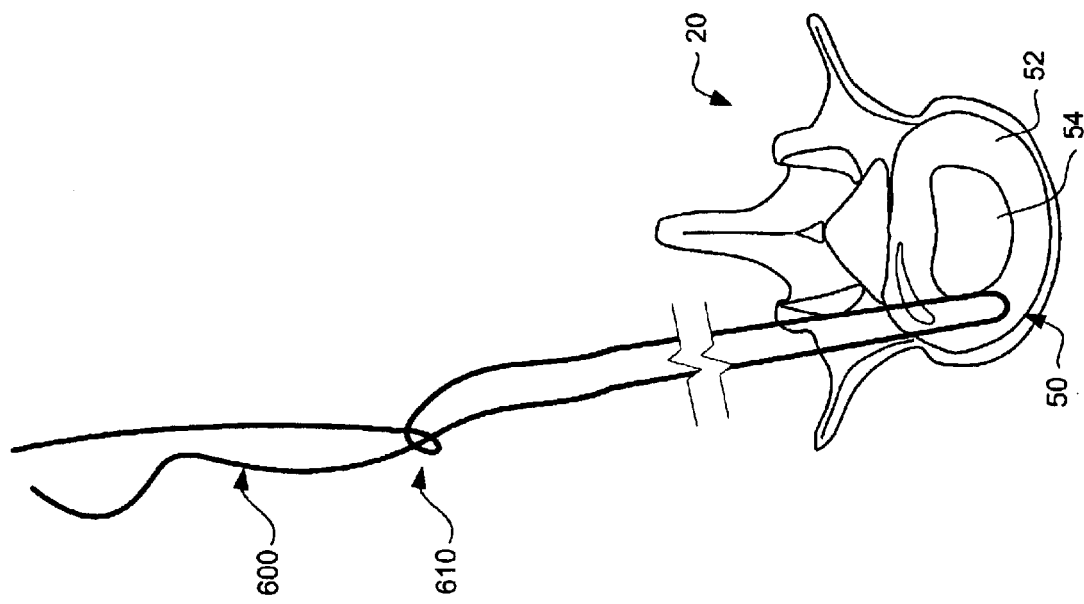
Figure 25G:
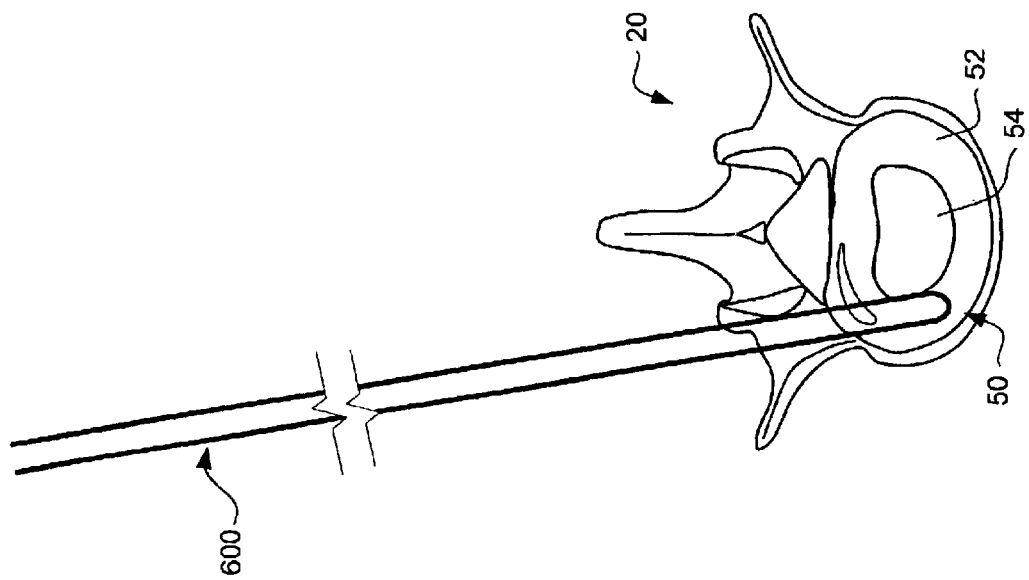

The stylet 770 is advanced until the distal tip 773 exits the proximal end of the second tube 762 as shown in FIG. 25D. One end of the reinforcement member 600 is attached to the proximal end of the stylet 770 as shown in FIG. 25E. This may be accomplished, for example, by threading the reinforcement member through a hole (not shown) in the proximal end of the stylet 770 similar to the threading a sewing needle. The distal end of the stylet 770 is pulled proximally to pull the stylet out of the trocar 760 and thread the reinforcement member 600 along the path defined by the stylet 770 as shown in FIG. 25F. At this point, the trocar 760 may be removed as shown in FIG. 25H, but may optionally be left in place, depending on the means employed to connect the ends of the reinforcement member 600.

Figure 25I:
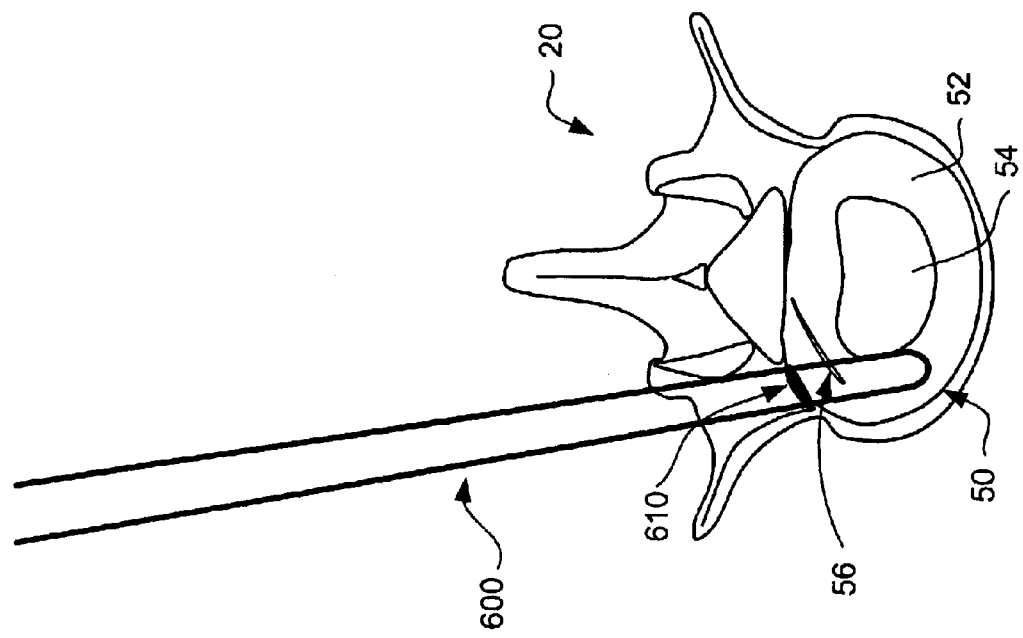
Figure 25J:
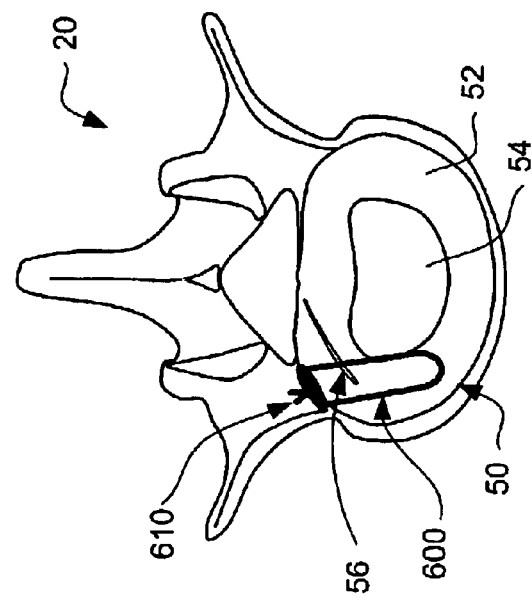

Although not shown, immediately before or immediately after the reinforcement member 600 is attached to the proximal end of the stylet 770, the pledget push rod 740 may be used to push the pledget 750 over the opposite ends of the reinforcement member 600 until the pledget 750 is positioned immediately adjacent the entry and exit points in the annulus 52. A connection (e.g., knot) 610 may be made in the reinforcement member 600 and advanced to the entry points of in the annulus 52 utilizing a conventional knot pusher (not shown) as shown in FIG. 25I. While the knot 610 is being tightened, the reinforcement member 600 applies compressive forces about the annulus 52 thereby closing fractures and fissures 56. Once the knot 610 has been tightened, the reinforcement member 600 may be cut immediately proximal of the knot 610 (proximal of pledget 750 if used) as shown in FIG. 25J utilizing a conventional suture cutting device (not shown).

Refer now to FIGS. 26A–26G which illustrate various tools 780/790/840 for implanting the reinforcement member 600 in accordance with the method illustrated in FIGS. 27A–27H. As seen in FIG. 26A, a dual lumen trocar 780 includes a dual lumen shaft 782 and a proximal handle 784. Rigid shaft 782 includes a sharpened tip 783 and a laterally facing opening 785. The rigid shaft 782 may be formed of stainless steel and may comprises a rigid outer tube 788 and a rigid inner tube 786 disposed eccentrically therein as seen in FIG. 26B. Inner tube 786 defines a lumen 787 extending through the entire shaft 782 and is sized to accommodate hollow stylet 790. A crescent-shaped lumen 789 is defined between the outer tube 788 and the inner tube 786. The crescent-shaped lumen 789 extends through the entire shaft 782 and is sized to accommodate hollow stylet 790. Opening 785 is also sized to accommodate the hollow stylet 790, and may be made even larger (e.g., 2–3 times larger) to accommodate variability in reentry as will be discussed in more detail hereinafter.

With reference to FIGS. 26C and 26D, hollow stylet 790 is substantially the same as stylet 710 except as described herein and illustrated in the drawings. Hollow stylet 790 includes an elongate flexible shaft 792 and a sharpened distal end 793. A lumen 791 extends through the entire shaft 792 and is sized to accommodate reinforcement member 600.

The shaft 792 of the hollow stylet 790 preferably has a flexible but pushable construction incorporating a rigid metal tube such as stainless steel hypotubing, or a super-elastic alloy tube such as nickel-titanium. Highly elastic or super-elastic materials incorporated into the elongate shaft 792 resist permanent deformation during insertion and navigation through the annulus 52. The shaft 792 of the stylet 790 may have a diameter ranging from 0.010 to 0.025 inches and is sized to fit within the lumens 787/789 of the shaft 792 of the trocar 790. The shaft 792 may be coated with a lubricious material such as PTFE and a hydrophilic polymer.

The stylet or needle 790 has a curved portion 794 and a separable curved tip 796. The separable curved tip 796 is connected to the reinforcement member 600 as shown in FIGS. 26E and 26F, but is separable from the remainder of the shaft 792. The curved portion 794 and the separable curved tip 796 may have the same diameter which may vary as described with reference to curved portion 712 of stylet 710 shown in FIGS. 12A–12E. The curved portion 774 together with separable tip 796 may have at least 360 degrees of curvature or more to define at least a full circle. Two example curvatures of the separable curved tip 796 are shown in FIGS. 26E and 26F.

The tip 793 of the hollow stylet 790 is sufficiently sharp to easily penetrate annular tissue 52, such that the path through the annular tissue 52 taken by the hollow stylet 790 will substantially conform to the geometry of the distal curved portion 794 and the curved separable tip 796. In particular, if the distal curved portion 794 and the curved separable tip 796 have a curve with at least 360 degrees of curvature or more, the hollow stylet 790 will exit the lumen 787 at the distal end of the inner tube 786 and naturally define a path through the annular tissue 52 to reenter the trocar 780 through opening 785 and into the lumen 789 of the outer tube 788. To this end, it is desirable to provide a tip 793 having sufficient sharpness to readily penetrate annular tissue 52, which tends to be relatively fibrous and tough. By providing a sufficiently sharp tip 793 with the appropriate geometry described above, the stylet 790 will naturally navigate through the annulus 52 and renter the trocar 780 without requiring visualization or steering of the stylet 790.

Push rod 840 may comprise a rigid mandrel having a length sufficient to extend through the shaft 782 of the trocar 780 and a diameter sufficient to permit passage through lumen 789. The distal end of the push rod 840 is adapted to engage the separable tip 796 as it renters the trocar 780 through opening 785, and lock the tip 796 relative to shaft 782 by mechanical compression, for example.

Refer now to FIGS. 27A–27H which illustrate a method for implanting the reinforcement member 600. The method illustrated in FIGS. 27A–27H utilizes hollow stylet 790 to navigate through the annulus 52 and implant reinforcement member 600. The method illustrated in FIGS. 27A–27H is similar to the method illustrated in FIGS. 18A–18L, except with regard to the automatic navigation of stylet 770 out of and back into the trocar 780. The method illustrated in FIGS. 27A–27H is particularly suited for a post discectomy procedure to close the opening (not shown) created thereby. Further, the method illustrated in FIGS. 27A–27H is particularly suited for a post annular compression procedure (e.g., contraction of annular tissue by thermal means) to maintain the re-compressed annulus (not shown) created thereby. All of the variables with regard to quantity, location, orientation, etc., discussed previously may be implemented by varying the generic procedure described hereinafter. The method illustrated in FIGS. 27A–27H is a percutaneous procedure in which access to the disc 50 is achieved utilizing a number of small diameter tools which may be inserted through a patient's back (skin and back muscles), between adjacent vertebrae, and adjacent the patient's disc 50.

Figure 27B:
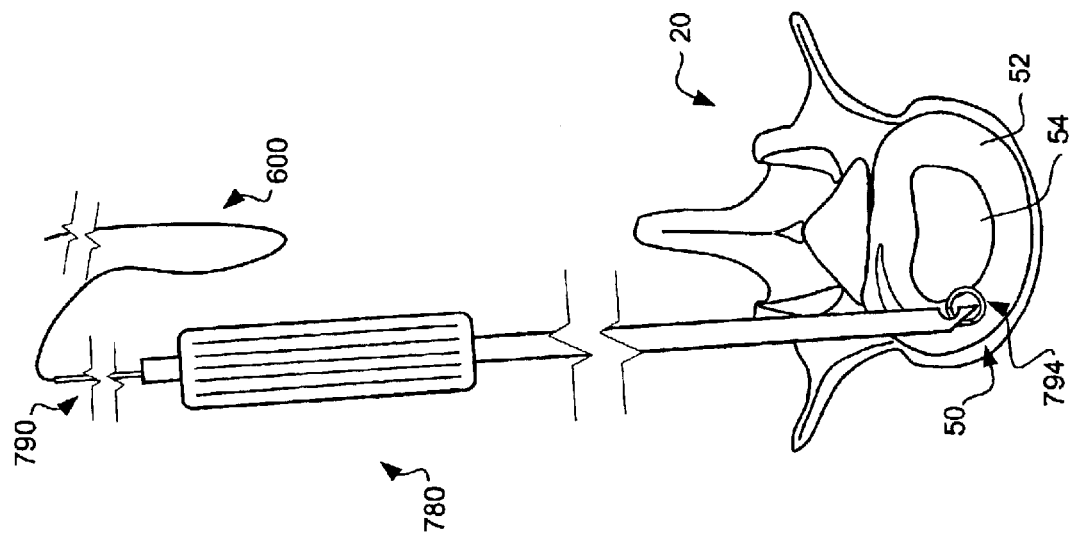
Figure 27A:
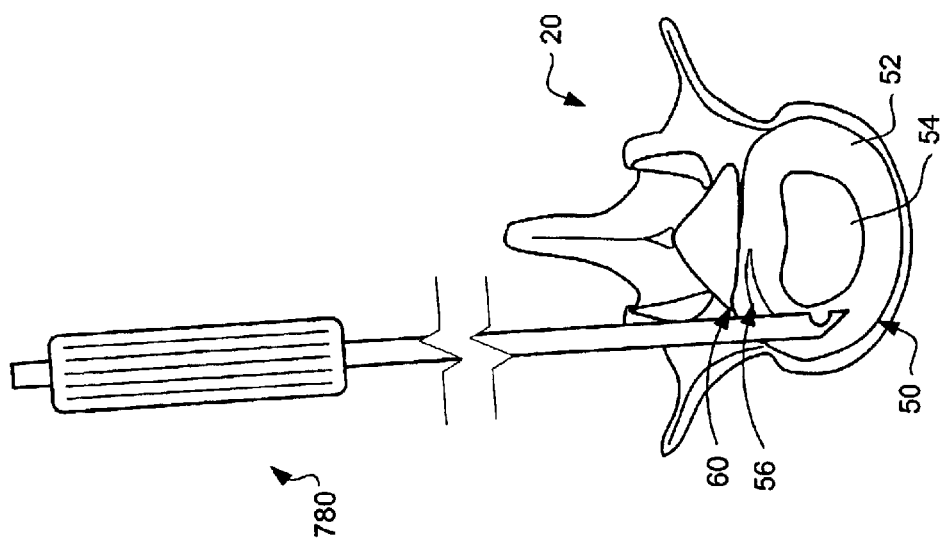

Initially, as shown in FIG. 27A, the rigid dual lumen trocar 780 is advanced until the distal tip thereof is disposed in the anterior portion of the annulus 52. The hollow stylet 790 is then inserted into the inner tube 786 of the rigid dual lumen trocar 780. The hollow stylet 790, having a curved distal portion 794 and separable tip portion 796, is advanced out the distal end of the shaft 782 into the annulus 52 as shown in FIG. 27B. The hollow stylet 790 is advanced until the distal tip 793 reenters the trocar 780 through the opening 785 at the distal end shaft 782 as shown in FIG. 27B. Note that the curvature of the curved portion 794, the curvature of the separable tip 796 is selected to automatically align with the opening 785 and thereby automatically reenter the trocar 780.

Figure 27D:
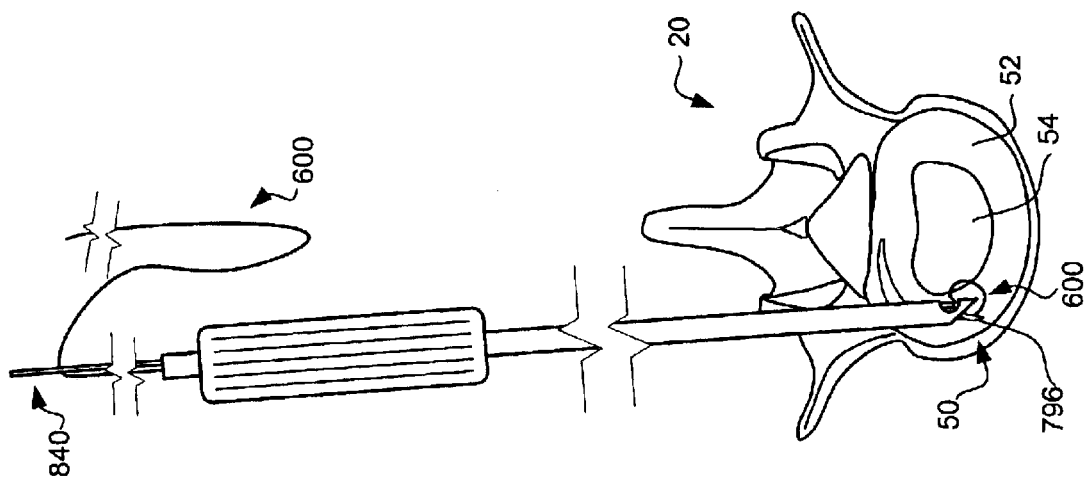
Figure 27C:
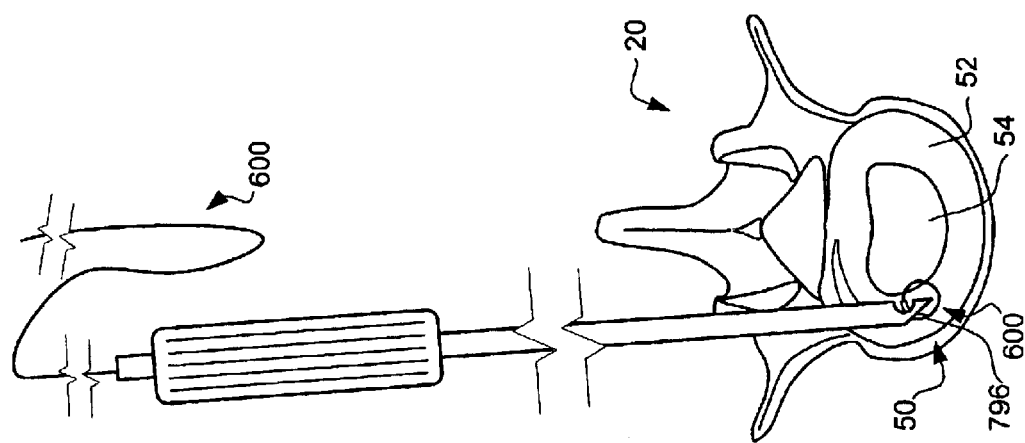

The proximal portion of the shaft 792 of the hollow stylet 790 is then withdrawn leaving separable tip 796 and reinforcement member 600 in place as shown in FIG. 27C. The push rod 840 is then advanced into the trocar 780 through lumen 789 until its distal end mechanically engages tip 796 and pinches or traps it relative to the distal end of the shaft 782 of the trocar 780 as shown in FIG. 27D. The proximal end of the push rod 840 and the handle 784 of the trocar are then grasped and pulled proximally while maintaining engagement of the distal end of the push rod 840 against the separable tip 796. As the proximal end of the push rod 840 and the handle 784 of the trocar are pulled proximally, the reinforcement member 600 is not grasped or otherwise restrained such that the reinforcement member 600 is free to be advanced distally and threaded along the path previously defined by hollow stylet 790 as shown in FIG. 27E.

Although not shown, the pledget push rod 740 may be used to push the pledget 750 over the opposite ends of the reinforcement member 600 until the pledget 750 is positioned immediately adjacent the entry and exit points in the annulus 52. A connection (e.g., knot) 610 may be made in the reinforcement member 600 and advanced to the entry points of in the annulus 52 utilizing a conventional knot pusher (not shown). While the knot 610 is being tightened, the reinforcement member 600 applies compressive forces about the annulus 52 thereby closing fractures and fissures 56 and reducing bulge 60. Once the knot 610 has been tightened, the reinforcement member 600 may be cut immediately proximal of the knot 610 (or proximal of pledget 750 if used) as shown in FIG. 27F utilizing a conventional suture cutting device (not shown).

Figure 27H:
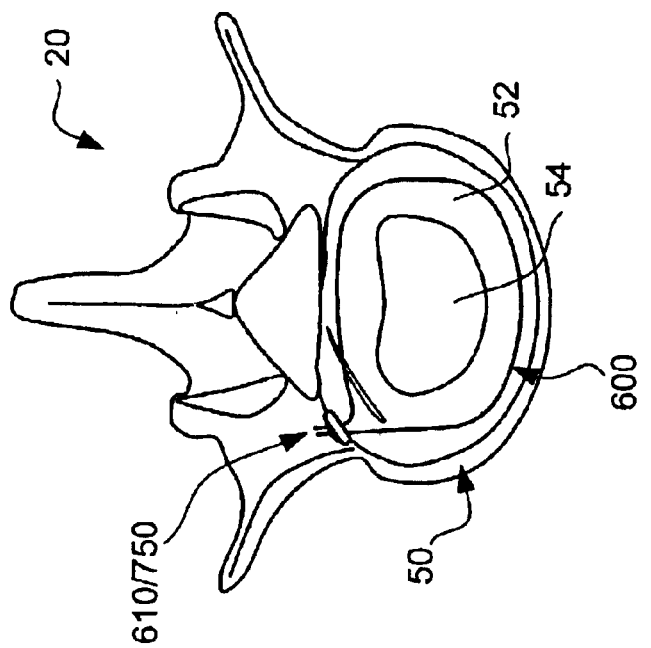
Figure 27G:
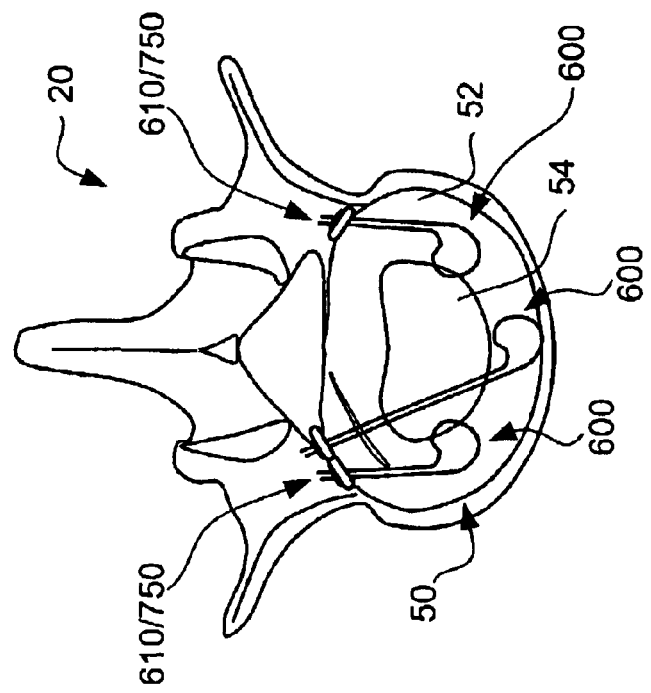

While a single path followed by a single reinforcement member 600 is illustrated in FIGS. 27A–27F, it is also contemplated that multiple reinforcement members 600 may be implanted as shown in FIG. 27G. For example, one reinforcement member 600 could be implanted proximate the lower (inferior) portion of the annulus 52 and one reinforcement member 600 could be implanted in the upper (superior) portion of the annulus 52. Any number of reinforcement members 600 could be implanted in a single disc, either through a single trocar 780 placement, or multiple trocar placements.

The path navigated through the annulus 52 by the foregoing method may be a function of the individual anatomical geometry of the patient and/or the particular portion of the annulus 52 requiring compression. Accordingly, the path defined by the stylet 790 and reinforcement member 600 through the annulus 52 may vary as shown in FIGS. 19A–19F by utilizing different stylet 790 curvatures and a sheath, similar to the method described with reference to FIGS. 18A–18L. By way of example, not limitation, a substantial rectangular path with rounded corners may be employed as illustrated in FIG. 27H.

From the foregoing, those skilled in the art will appreciate that the present invention provides reinforcement devices 100, 200, 300, 600, 510, 520, 530, 540, 570 and 580, which may be used to reinforce a damaged disc, while permitting relative movement of the adjacent vertebrae. The present invention also provides minimally invasive methods of implanting such devices as described above.

All of the implantable devices and delivery tools therefor described above may incorporate heating mechanisms (e.g., resistive wire coils) to allow for heating the surrounding tissue, such as temporarily and directly heating annular tissue. In addition or in the alternative, a separate device may be provided specifically for heating annular tissue, which may be used to accomplish results similar to those described with reference to FIG. 4H. By way of example, not limitation, the following is a description of a device specifically adapted to heat annular tissue, but the methods and principles of operation are equally applicable to all devices disclosed herein that come into contact with annular tissue.

Figure 28A:
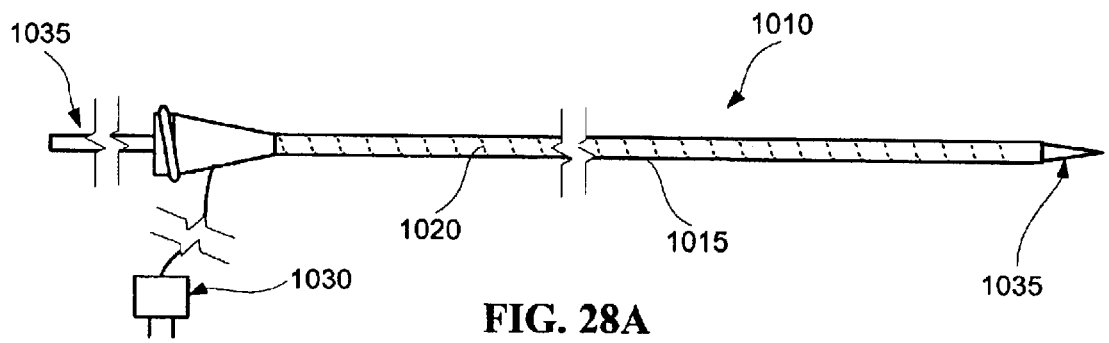
FIGS. 28A–28C illustrate various heating probes of the present invention for temporarily heating annular tissue.

FIG. 28A illustrates an exemplary embodiment of a thermal probe 1010 which may be temporarily positioned within the annulus and heated. The thermal probe 1010 may comprise a hollow shaft 1015, which contains a heating element extending at least a portion of the length of the shaft 1015. The thermal probe 1010 may be advanced through the annulus over one or more stylets in the same fashion as sheath 730 as described with reference to FIGS. 18A through 18F utilizing one or a series of stylets 1035 incorporating curvatures as shown and described with reference to FIGS. 12A through 12E.

Figure 28B:
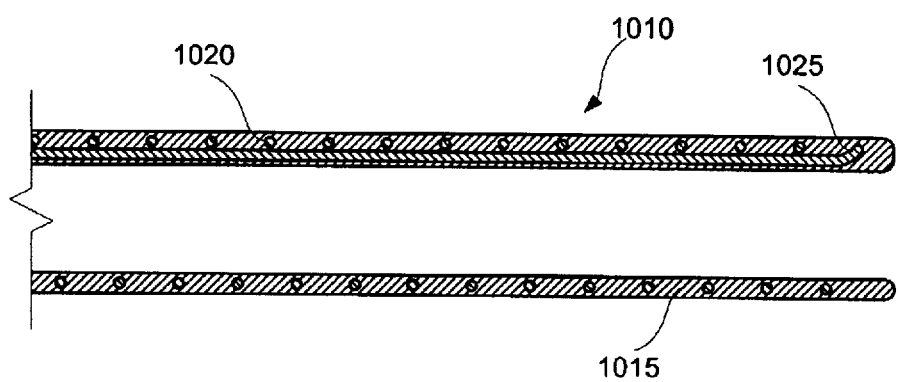

The heating element may comprise, for example, a coil or braid of resistive metallic wire. As seen in FIG. 28B, a detailed view of a distal portion of the probe 1010 is shown, which includes a resistive wire coil 1020 encapsulated by the polymeric material of the shaft 1015. The polymeric shaft material may comprise electrically insulative material and may be selected to tolerate relatively high temperatures, such as PTFE or polyimide. At the distal end of the coil 1020, the resistive wire may extend proximally as a return wire 1025. A plug 1030, connected to the proximal end of the thermal probe 1010 may provide connection to a power source (not shown). Direct or alternating current may be used to electrify the resistive wire coil 1020, causing heating, which in turn heats the annular tissue. Temperature may be controlled by the amount of electric power delivered. One or more thermocouples may be included in the shaft 1015 of the probe 1010 (not shown).

Figure 28C:
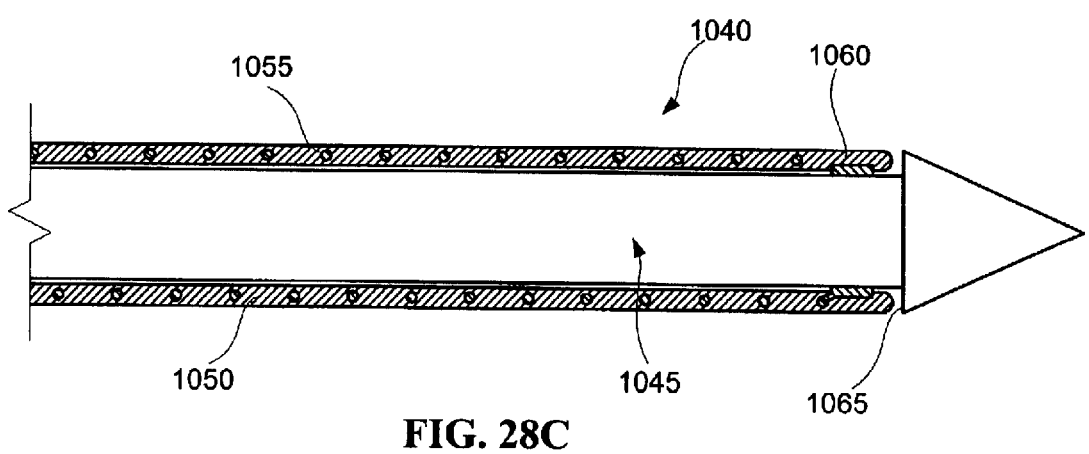

An alternative probe 1040 is illustrated in FIG. 28C. The stylet 1045 used for delivery of thermal probe 1040 could also be used as the return electrode. As shown in FIG. 28C, the shaft 1050 includes a resistive coil 1055, terminating near the distal end at a contact 1060. The contact 1060 provides electrical connection between the stylet 1045 and the resistive wire coil 1055. In this embodiment, the stylet 1045 may be electrically conductive, and is preferably metallic. The stylet 1045 optionally includes a shoulder 1065 which allows for the probe 1040 to be advanced in a "fixed wire" fashion, together with the stylet 1045. This "fixed wire" approach incorporating an optional shoulder 1065 on the stylet 1045 is also applicable to the above described implants and delivery devices, e.g. stylet 710 and sheath 730 illustrated in FIGS. 18A through 18F.

The thermal probe 1010/1040 may be positioned directly within the annulus, in the same manner as described in connection with the positioning of the implant 100 shown in FIGS. 8A through 8K. But rather than implant 100, thermal probe 1010/1040 would be positioned and activated. These figures illustrate positioning in the posterior annulus, but it is within the scope of this invention that the thermal probe 1010/1040 could be positioned anywhere within the annulus or across the disc, including the positions illustrated in FIGS. 19A through 19F. For example, the probe 1010/1040 could be positioned in the lateral annulus, anterior annulus, or multiple regions of the annulus, including circumferentially in the annulus, as illustrated for the sheath 730 illustrated in FIGS. 18A through 18F.

The thermal probe 1010/1040 may also incorporate an anchoring mechanism to facilitate compression of the annular tissue prior to heating. For example, the probe 1010/1040 could include progressive external threads such as described in connection with the implant of FIG. 4A.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method for treating an intervertebral disc in a patient's spine, the disc having an annulus and a nucleus, the method comprising:

providing an implant; and positioning the implant around annular tissue such that the implant substantially encircles at least a portion of the nucleus, wherein the implant compresses at least a portion of the annulus.

2. A method as in claim 1, wherein the implant extends through and around annular tissue.

3. A method as in claim 1, wherein the implant comprises an elongate member and a pledget.

4. A method as in claim 1, wherein the implant comprises a flexible elongate member.

5. A method as in claim 4, wherein the flexible elongate member comprises a suture.

6. A method as in claim 1, wherein the implant resides within the annulus.

7. A method as in claim 1, wherein the implant resides outside the nucleus and the annulus.

8. A method as in claim 1, wherein the implant completely encircles the nucleus.

9. A method using claim 1, wherein the implant comprises an elongate member having a first end and a second end, wherein the ends are connected together.

10. A method as in claim 1, wherein the implant comprises an elongate member having a plurality of anchors residing within the annulus.

11. A method for treating an intervertebral disc in a patient's spine. the disc having an annulus and a nucleus, the method comprising:

providing an implant comprising an elongate member and a pledget;

positioning the implant around annular tissue such that the implant substantially encircles at least a portion of the nucleus.

12. A method for treating an intervertebral disc in a patient's spine, the disc having an annulus and a nucleus, the method comprising:

providing an implant;

positioning the implant around annular tissue such that the implant completely encircles the nucleus.

* * * * *